(12) United States Patent
Seow et al.

(10) Patent No.: US 12,295,577 B2
(45) Date of Patent: May 13, 2025

(54) TISSUE CUSHION ADJUNCTS FOR SURGICAL STAPLER END EFFECTOR

(71) Applicant: Cilag GmbH International, Zug (CH)

(72) Inventors: Christopher Q. Seow, Cincinnati, OH (US); Gregory J. Bakos, Mason, OH (US); Michael J. Vendely, Lebanon, OH (US); Jason L. Harris, Lebanon, OH (US); Mark S. Zeiner, Mason, OH (US); Andréas N. Ward, Cincinnati, OH (US); Adam D. Hensel, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/704,075

(22) Filed: Mar. 25, 2022

(65) Prior Publication Data

US 2023/0301656 A1   Sep. 28, 2023

(51) Int. Cl.
*A61B 17/072* (2006.01)
*A61B 17/068* (2006.01)
*A61B 17/00* (2006.01)

(52) U.S. Cl.
CPC .... *A61B 17/07292* (2013.01); *A61B 17/0686* (2013.01); *A61B 2017/00951* (2013.01);
(Continued)

(58) Field of Classification Search
CPC .......... A61B 17/0686; A61B 17/07292; A61B 2017/00951; A61B 2017/07264; A61B 2017/07271; A61B 2017/07285
See application file for complete search history.

(56) References Cited

U.S. PATENT DOCUMENTS

| 5,810,855 A | 9/1998 | Rayburn et al. |
| 7,380,696 B2 | 6/2008 | Shelton, IV et al. |

(Continued)

FOREIGN PATENT DOCUMENTS

| EP | 2090248 A2 | 8/2009 |
| EP | 3150134 A1 | 4/2017 |

(Continued)

OTHER PUBLICATIONS

International Search Report and Written Opinion dated Aug. 2, 2023, for International Application No. PCT/IB2023/052793, 20 pages.

(Continued)

*Primary Examiner* — Robert F Long
*Assistant Examiner* — Eduardo R Ferrero
(74) *Attorney, Agent, or Firm* — Frost Brown Todd LLC

(57) ABSTRACT

A surgical instrument includes a first and second jaw, a firing assembly, a first buttress assembly, and a second buttress assembly. The first and second jaw actuate relative to each other between an open and closed position to grasp tissue. The second jaw includes a fastening assembly having a deck defining a plurality of openings and a plurality of fasteners housed within the openings. The firing assembly drives the plurality of fasteners out of the plurality of openings against a plurality of fastening forming features of the first jaw. The first buttress assembly and the second buttress assembly are associated with the first and second jaw, respectively. The first buttress assembly includes a first material and a first thickness. The second buttress assembly includes a second material and a second thickness. The first material and the second material differ in rigidity. The first thickness and the second thickness are different.

14 Claims, 36 Drawing Sheets

(52) U.S. Cl.
CPC .............. *A61B 2017/07264* (2013.01); *A61B 2017/07271* (2013.01); *A61B 2017/07285* (2013.01)

(56) References Cited

U.S. PATENT DOCUMENTS

| | | | |
|---|---|---|---|
| 7,845,533 | B2 | 12/2010 | Marczyk et al. |
| 8,034,396 | B2 | 10/2011 | Kapiamba et al. |
| 8,210,411 | B2 | 7/2012 | Yates et al. |
| 8,408,439 | B2 | 4/2013 | Huang et al. |
| 8,453,914 | B2 | 6/2013 | Laurent et al. |
| 9,186,142 | B2 | 11/2015 | Fanelli et al. |
| 9,271,706 | B2 | 3/2016 | Stopek et al. |
| 9,364,233 | B2 | 6/2016 | Alexander, III et al. |
| 9,517,065 | B2 | 12/2016 | Simms et al. |
| 9,622,746 | B2 | 4/2017 | Simms et al. |
| 9,649,110 | B2 | 5/2017 | Parihar et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,839,421 | B2 | 12/2017 | Zerkle et al. |
| 9,907,554 | B2 | 3/2018 | Morgan et al. |
| 10,092,292 | B2 | 10/2018 | Boudreaux et al. |
| 10,166,023 | B2 | 1/2019 | Vendely et al. |
| 10,349,939 | B2 | 7/2019 | Shelton, IV et al. |
| 10,426,481 | B2 | 10/2019 | Aronhalt et al. |
| 10,441,285 | B2 | 10/2019 | Shelton, IV et al. |
| 10,524,788 | B2 | 1/2020 | Vendely et al. |
| 10,568,621 | B2 | 2/2020 | Shelton, IV et al. |
| 10,588,623 | B2 | 3/2020 | Schmid et al. |
| 10,624,861 | B2 | 4/2020 | Widenhouse et al. |
| 10,639,039 | B2 * | 5/2020 | Vendely .................. A61B 50/30 |
| 10,667,808 | B2 | 6/2020 | Baxter, III et al. |
| 10,758,398 | B2 | 9/2020 | Murthy Aravalli et al. |
| 10,945,731 | B2 | 3/2021 | Baxter, III et al. |
| 10,966,722 | B2 | 4/2021 | Shelton, IV et al. |
| 10,987,107 | B2 | 4/2021 | Sgroi, Jr. et al. |
| 11,058,425 | B2 | 7/2021 | Widenhouse et al. |
| 11,382,625 | B2 | 7/2022 | Huitema et al. |
| 11,660,093 | B2 | 5/2023 | Bakos et al. |
| 11,857,190 | B2 | 1/2024 | Strang et al. |
| 2002/0165563 | A1* | 11/2002 | Grant .................... A61B 17/072 606/151 |
| 2004/0004105 | A1* | 1/2004 | Jankowski ........ A61B 17/07207 227/176.1 |
| 2005/0263562 | A1 | 12/2005 | Shelton, IV et al. |
| 2009/0020584 | A1 | 1/2009 | Soltz et al. |
| 2009/0206143 | A1* | 8/2009 | Huitema .......... A61B 17/07292 227/176.1 |
| 2010/0331880 | A1 | 12/2010 | Stopek et al. |
| 2011/0077629 | A1 | 3/2011 | Tanaka et al. |
| 2012/0080336 | A1 | 4/2012 | Shelton, IV et al. |
| 2012/0080337 | A1* | 4/2012 | Shelton, IV ............ A61B 17/29 206/339 |
| 2012/0080498 | A1* | 4/2012 | Shelton, IV .......... A61B 17/072 227/180.1 |
| 2012/0080503 | A1* | 4/2012 | Woodard, Jr. ....... A61B 17/0643 227/181.1 |
| 2012/0083836 | A1* | 4/2012 | Shelton, IV ..... A61B 17/00234 206/339 |
| 2012/0125792 | A1 | 5/2012 | Cassivi |
| 2012/0136345 | A1 | 5/2012 | Takashino |
| 2012/0241492 | A1* | 9/2012 | Shelton, IV ..... A61B 17/07292 227/175.1 |
| 2012/0241503 | A1* | 9/2012 | Baxter, III ............ A61B 17/068 227/176.1 |
| 2012/0241505 | A1 | 9/2012 | Alexander, III et al. |
| 2013/0075448 | A1* | 3/2013 | Schmid ............ A61B 17/07207 227/176.1 |
| 2013/0146641 | A1* | 6/2013 | Shelton, IV ....... A61B 17/0643 227/176.1 |
| 2013/0146643 | A1* | 6/2013 | Schmid ................ A61B 17/072 227/176.1 |
| 2013/0153635 | A1 | 6/2013 | Hodgkinson |
| 2013/0214030 | A1* | 8/2013 | Aronhalt et al. |
| 2013/0221062 | A1* | 8/2013 | Hodgkinson .... A61B 17/07292 227/176.1 |
| 2013/0256375 | A1* | 10/2013 | Shelton, IV ........ A61B 17/0643 227/176.1 |
| 2013/0256376 | A1* | 10/2013 | Barton ................ A61B 17/068 227/176.1 |
| 2014/0131419 | A1 | 5/2014 | Bettuchi |
| 2014/0158741 | A1 | 6/2014 | Woodard, Jr. et al. |
| 2014/0166721 | A1 | 6/2014 | Stevenson et al. |
| 2014/0205637 | A1* | 7/2014 | Widenhouse ............ A61K 9/70 424/400 |
| 2014/0209658 | A1* | 7/2014 | Skalla ................ A61B 17/1155 227/175.1 |
| 2014/0224686 | A1* | 8/2014 | Aronhalt ............ A61B 17/0682 206/339 |
| 2014/0291382 | A1* | 10/2014 | Lloyd .............. A61B 17/07207 227/176.1 |
| 2015/0136831 | A1 | 5/2015 | Baxter, III et al. |
| 2015/0196296 | A1 | 7/2015 | Swayze et al. |
| 2015/0196348 | A1 | 7/2015 | Yates et al. |
| 2015/0282809 | A1 | 10/2015 | Shelton, IV et al. |
| 2015/0297219 | A1* | 10/2015 | Shelton, IV ..... A61B 17/07207 227/176.1 |
| 2016/0106426 | A1* | 4/2016 | Shelton, IV .......... A61B 17/072 227/176.1 |
| 2016/0106427 | A1* | 4/2016 | Shelton, IV .......... A61B 17/072 227/176.1 |
| 2016/0278764 | A1* | 9/2016 | Shelton, IV .......... A61B 17/105 |
| 2016/0278765 | A1 | 9/2016 | Shelton, IV et al. |
| 2016/0278774 | A1 | 9/2016 | Shelton, IV et al. |
| 2017/0055981 | A1* | 3/2017 | Vendely ........... A61B 17/07292 |
| 2017/0055986 | A1* | 3/2017 | Harris ................ A61B 17/1155 |
| 2017/0086838 | A1 | 3/2017 | Harris et al. |
| 2017/0086841 | A1 | 3/2017 | Vendely et al. |
| 2017/0086845 | A1 | 3/2017 | Vendely et al. |
| 2017/0119390 | A1* | 5/2017 | Schellin ........... A61B 17/07207 |
| 2017/0119392 | A1* | 5/2017 | Shelton, IV .......... A61B 17/105 |
| 2018/0103952 | A1* | 4/2018 | Aronhalt .......... A61B 17/07207 |
| 2018/0235624 | A1 | 8/2018 | Shelton, IV et al. |
| 2018/0235626 | A1* | 8/2018 | Shelton, IV ..... A61B 17/07207 |
| 2019/0008518 | A1 | 1/2019 | Sgroi, Jr. et al. |
| 2019/0200978 | A1 | 7/2019 | Shelton, IV et al. |
| 2019/0269402 | A1 | 9/2019 | Murray et al. |
| 2019/0298338 | A1* | 10/2019 | Vendely ........... A61B 17/07207 |
| 2019/0314016 | A1 | 10/2019 | Huitema et al. |
| 2019/0314018 | A1 | 10/2019 | Huitema et al. |
| 2020/0205825 | A1* | 7/2020 | Vendely .......... A61B 17/320092 |
| 2020/0305963 | A1 | 10/2020 | Wagner et al. |
| 2020/0390944 | A1 | 12/2020 | Williams et al. |
| 2021/0128129 | A1 | 5/2021 | George et al. |
| 2022/0061843 | A1 | 3/2022 | Vendely et al. |
| 2022/0160360 | A1 | 5/2022 | Harris et al. |
| 2022/0313247 | A1* | 10/2022 | Shelton, IV ........ A61B 17/0686 |
| 2023/0301657 | A1 | 9/2023 | Zeiner et al. |
| 2023/0301674 | A1 | 9/2023 | Rector et al. |
| 2023/0301675 | A1 | 9/2023 | Seow et al. |
| 2023/0320742 | A1 | 10/2023 | Bakos et al. |

FOREIGN PATENT DOCUMENTS

| | | |
|---|---|---|
| EP | 3150142 A2 | 4/2017 |
| EP | 3162384 A1 | 5/2017 |
| EP | 3363387 A1 | 8/2018 |
| EP | 3424441 A2 | 1/2019 |
| EP | 3530213 A2 | 8/2019 |
| EP | 3791802 A1 | 3/2021 |
| EP | 3791805 A1 | 3/2021 |
| EP | 3791806 A1 | 3/2021 |

OTHER PUBLICATIONS

International Search Report and Written Opinion dated Jul. 31, 2023, for International Application No. PCT/IB2023/052804, 21 pages.

(56) References Cited

OTHER PUBLICATIONS

International Search Report and Written Opinion dated Aug. 7, 2023, for International Application No. PCT/IB2023/052805, 21 pages.
International Search Report and Written Opinion dated Aug. 9, 2023, for International Application No. PCT/IB2023/052809, 20 pages.
International Search Report and Written Opinion dated Jun. 20, 2023, for International Application No. PCT/IB2023/052810, 16 pages.

* cited by examiner

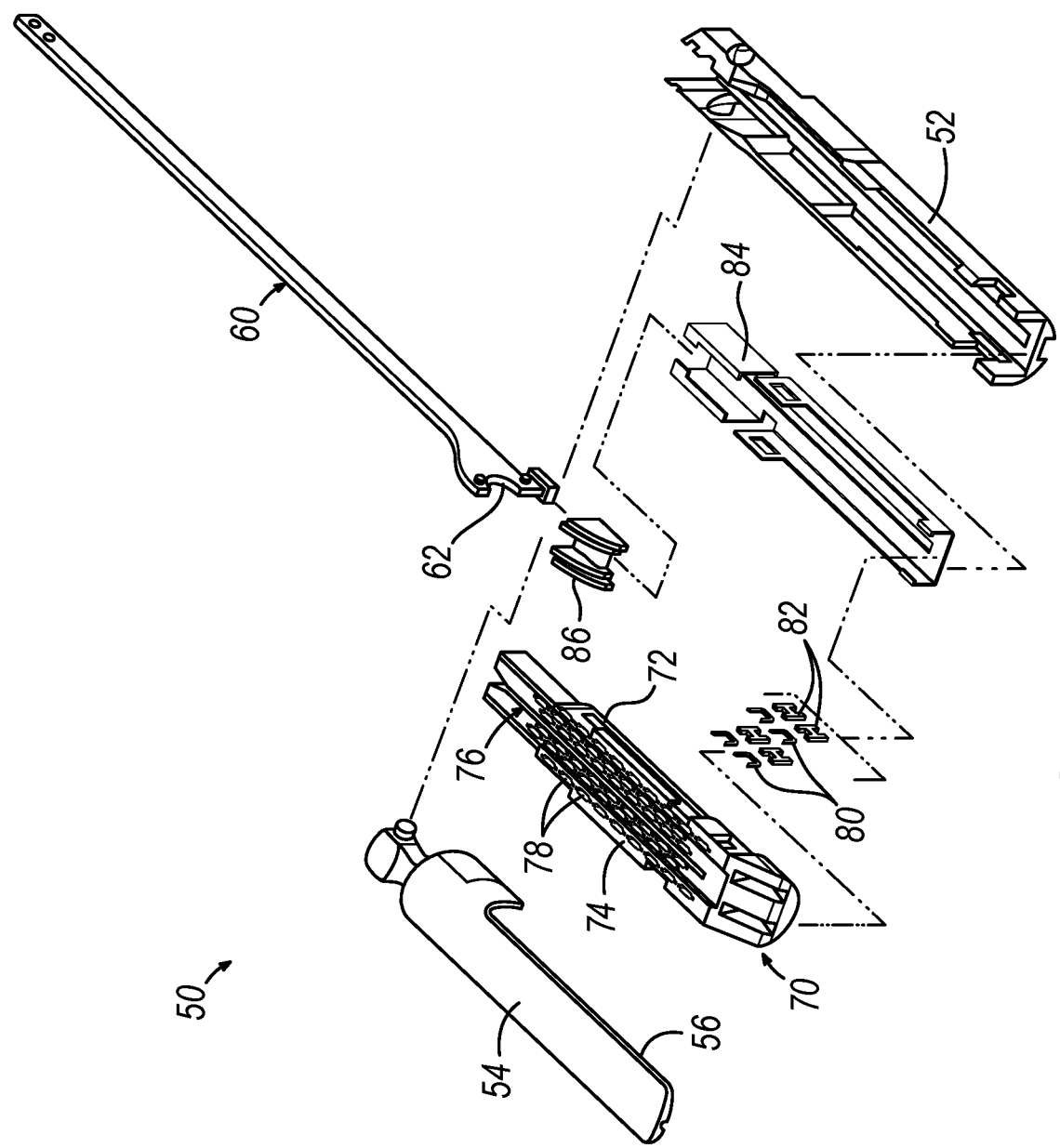

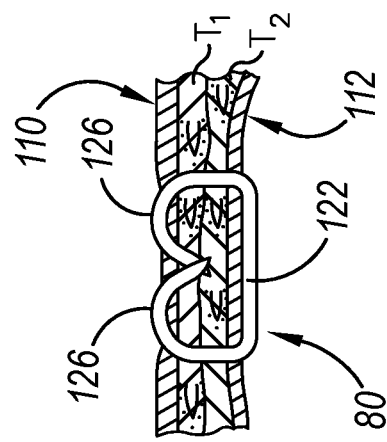
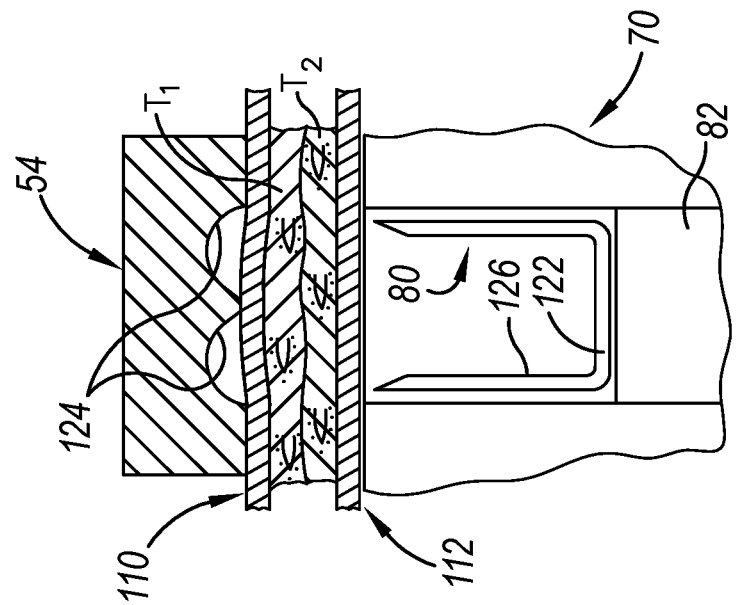
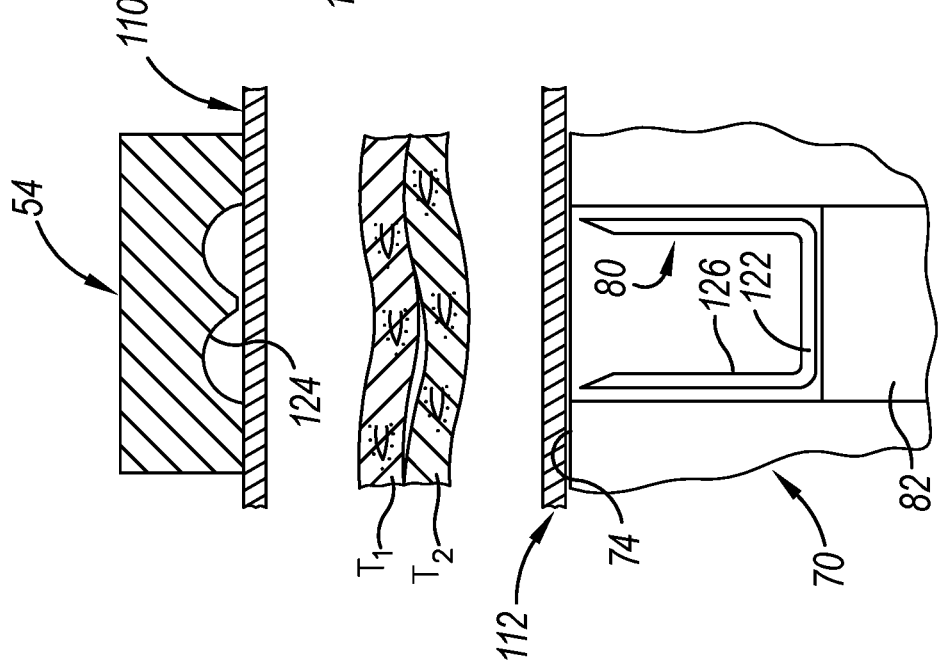

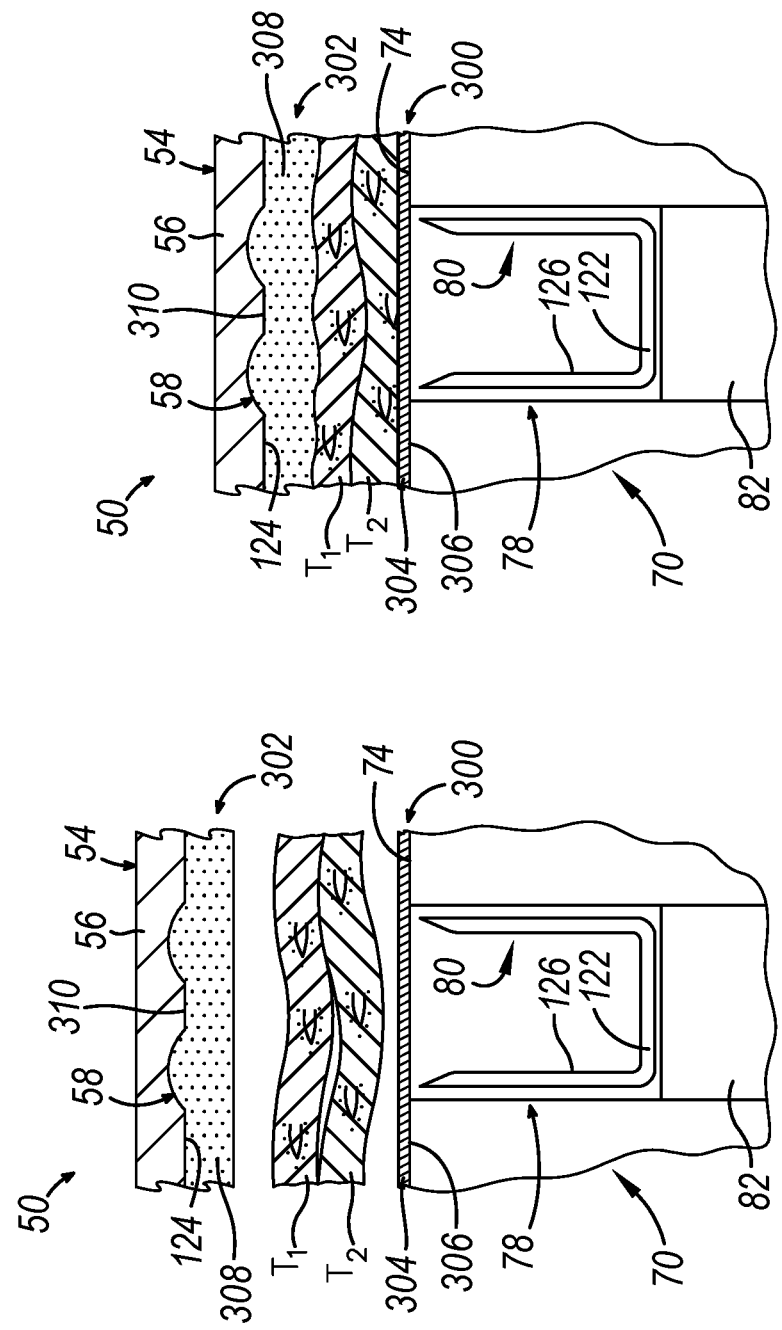

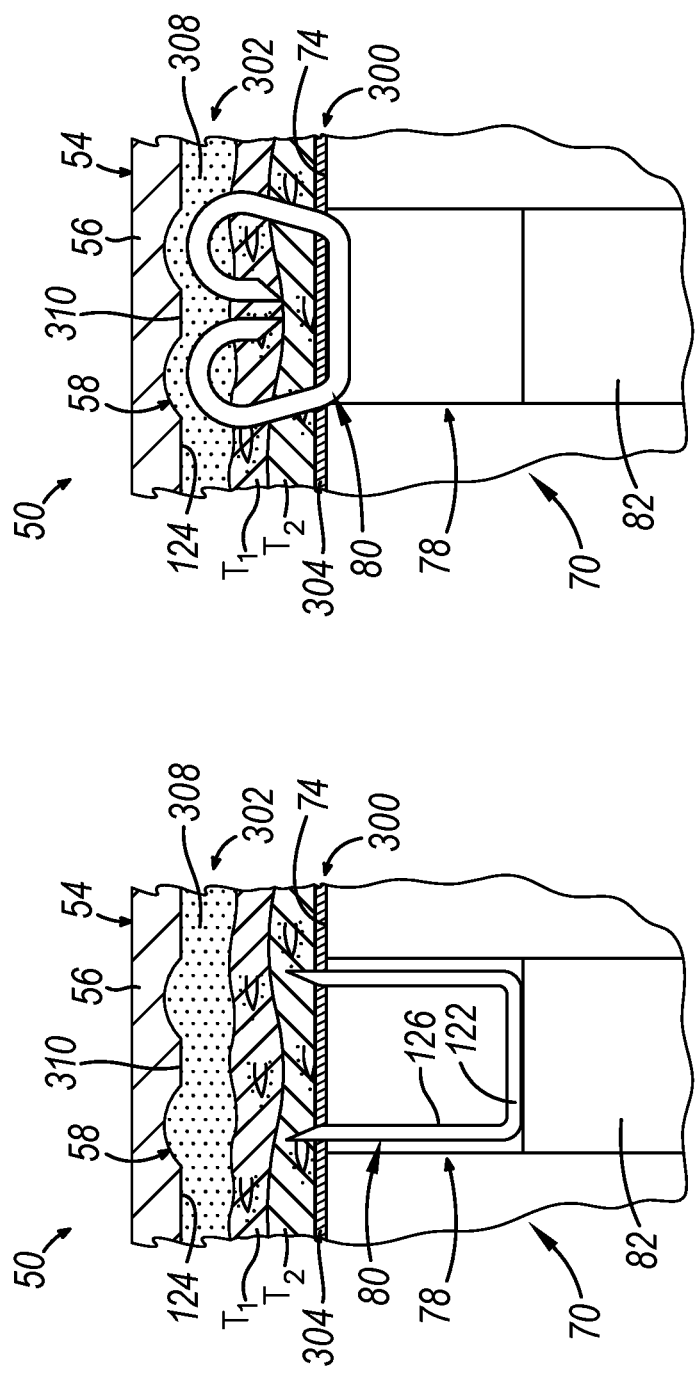

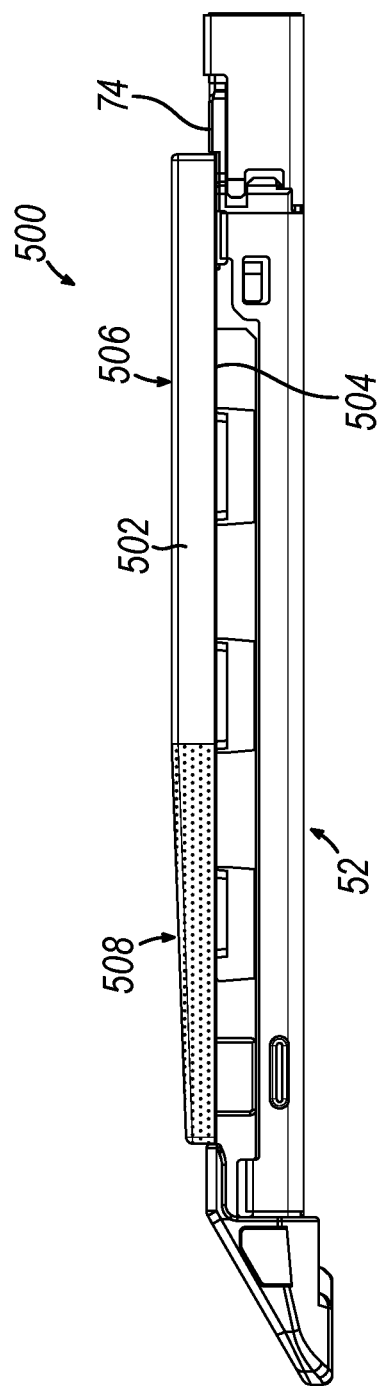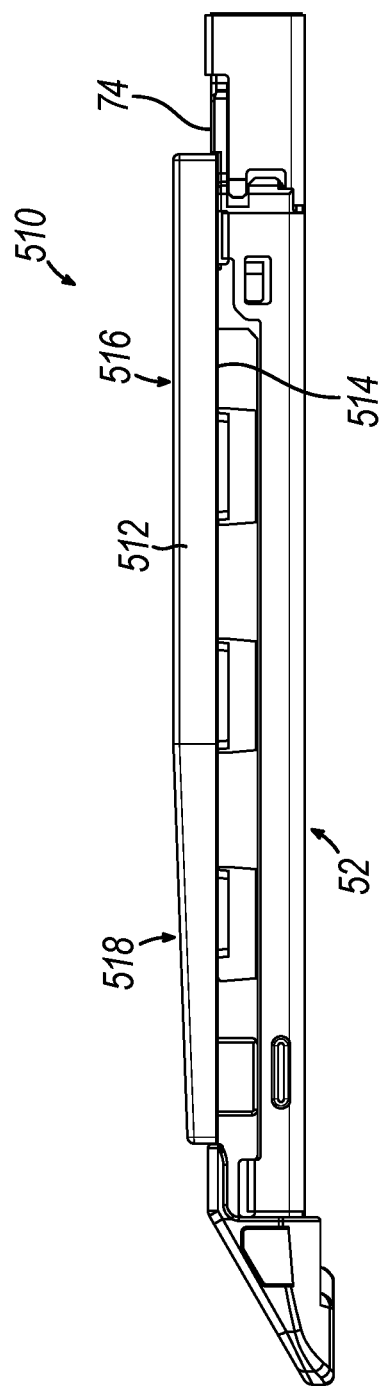

TISSUE CUSHION ADJUNCTS FOR SURGICAL STAPLER END EFFECTOR

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4 depicts an exploded perspective view of the end effector of FIG. 3;

FIG. 8A depicts a cross-sectional end view of a portion of the end effector of FIG. 3 with the buttress assemblies of FIG. 7 applied to the upper and lower jaws of the end effector, showing the end effector jaws in an open state with tissue positioned between the upper and lower jaws;

FIG. 8B depicts a cross-sectional end view of the end effector and buttress assemblies of FIG. 8A, showing the end effector jaws in a closed state on the tissue;

FIG. 8C depicts a cross-sectional view of a formed staple and the buttress assemblies of FIG. 8A after having been secured to the tissue by the end effector of FIG. 3;

FIG. 14A depicts a cross-sectional end view of a portion of the end effector of FIG. 3 with alternative buttress assemblies applied to the upper and lower jaws of the end effector, showing the end effector jaws in an open state with tissue positioned between the upper and lower jaws;

FIG. 14B depicts a cross-sectional end view of the end effector and buttress assemblies of FIG. 14A, showing the end effector jaws in a closed state on the tissue;

FIG. 14C depicts a cross-sectional end view of the end effector and buttress assemblies of FIG. 14A, showing a partially fired staple while the end effector jaws are in a closed state on the tissue;

FIG. 14D depicts a cross-sectional view of a formed staple and the buttress assemblies of FIG. 14A after having been secured to the tissue by the end effector of FIG. 3;

FIG. 41 depicts an elevational side view of an alternative buttress assembly attached to the staple cartridge of the end effector of FIG. 3;

FIG. 42 depicts an elevational side view of an alternative buttress assembly attached to the staple cartridge of the end effector of FIG. 3;

Figure 1:
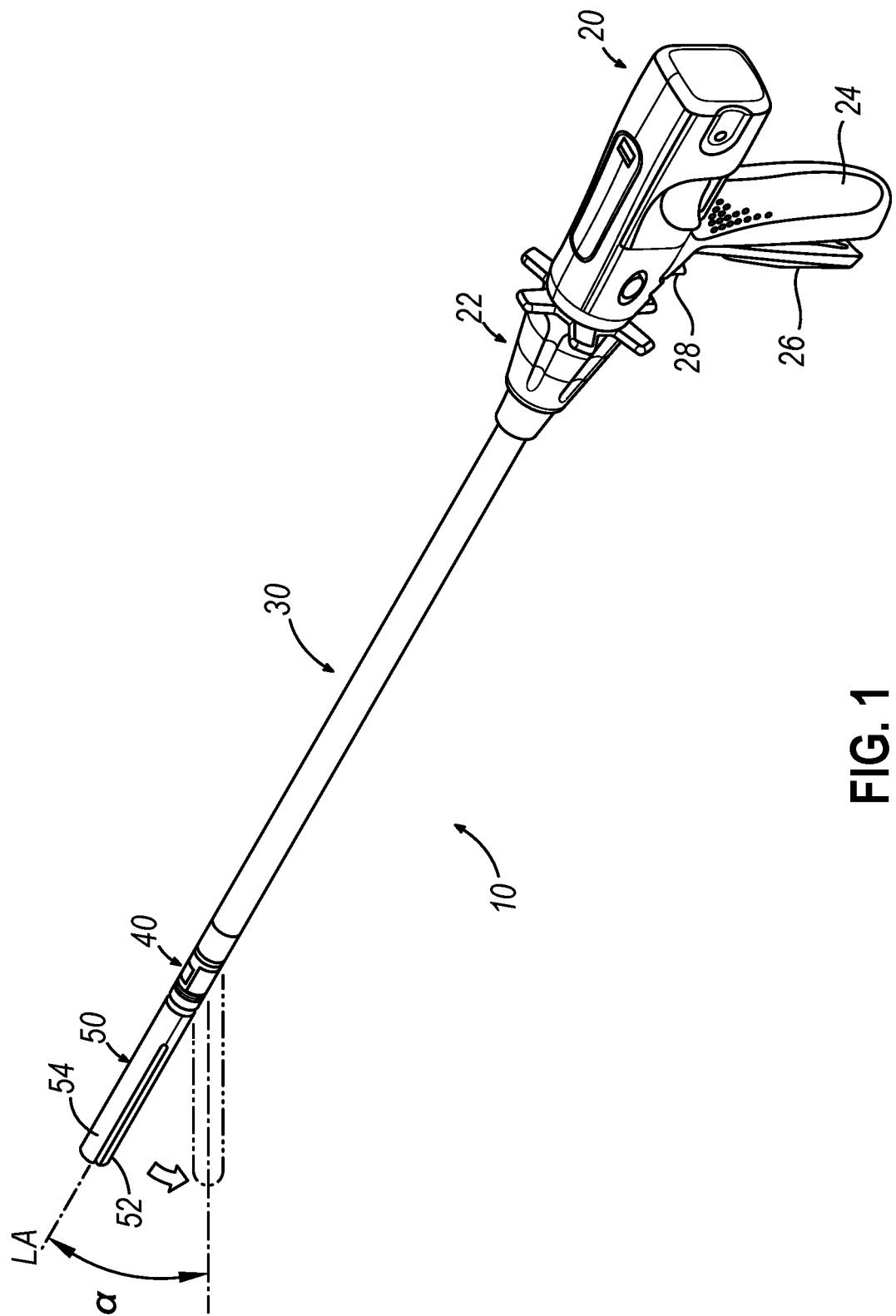
FIG. 1 depicts a perspective view of an exemplary surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. Exemplary Surgical Stapler

Figure 2:
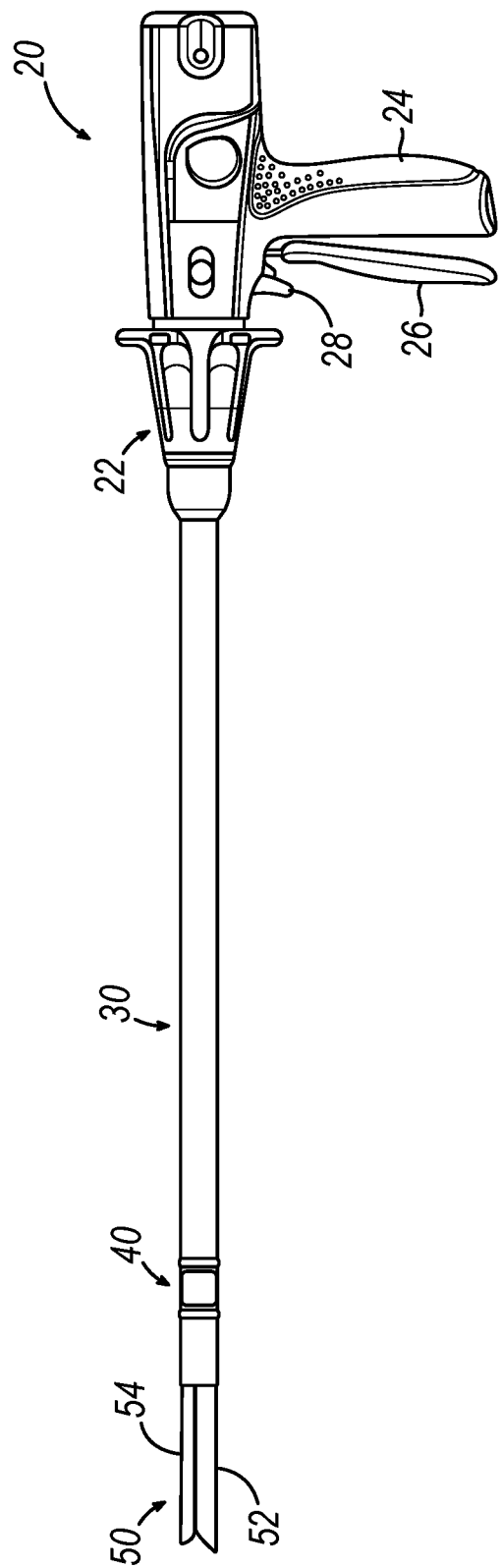
FIG. 2 depicts a side elevational view of the surgical stapler of FIG. 1.

FIGS. 1-6 show an exemplary surgical stapler (10) that is sized for insertion through a trocar cannula or an incision (e.g., thoracotomy, etc.) to a surgical site in a patient for performing a surgical procedure. As shown in FIGS. 1 and 2, surgical stapler (10) of the present example includes a proximal body in the form of a handle assembly (20), a shaft assembly (30) extending distally from handle assembly (20) and terminating at an articulation joint (40), and an end effector (50) coupled with the distal end of shaft assembly (30) via articulation joint (40). Articulation joint (40) is configured to enable lateral deflection, either actively or passively, of end effector (50) relative to a longitudinal axis (LA) of shaft assembly (30) to a desired angle (a) via actuation of an articulation control feature (22) of handle assembly (20).

Figure 3:
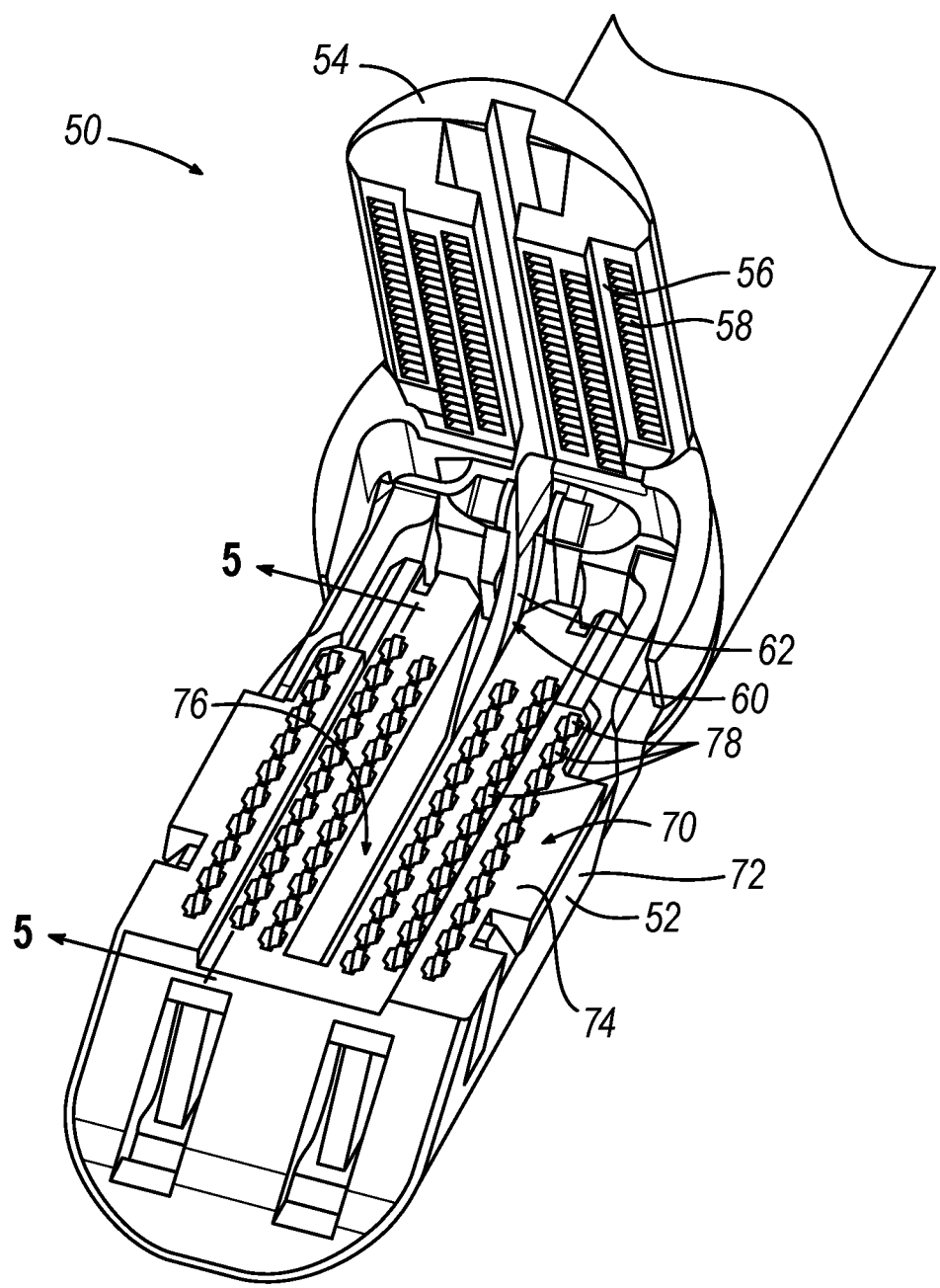
FIG. 3 depicts a perspective view of an end effector of the surgical stapler of FIG. 1 in an open state.

As shown best in FIGS. 3 and 4, end effector (50) includes a lower jaw (52) that supports a stapling assembly in the form of a replaceable staple cartridge (70), and an upper jaw (54) that presents an anvil (56) having a plurality of staple forming pockets (58). Upper jaw (54) is configured to pivot relative to lower jaw (52) to clamp tissue between staple cartridge (70) and anvil (56) and subsequently form staples deployed by staple cartridge (70). End effector (50) further includes an elongate firing member (60) configured to translate distally through end effector (50) to drive staples from staple cartridge (70) toward anvil (56) and simultaneously cut tissue with a distally presented cutting edge (62). Accordingly, end effector (50) is operable to clamp, staple, and cut tissue.

As shown best in FIGS. 1 and 2, handle assembly (20) further includes a pistol grip (24), a closure trigger (26), and a firing trigger (28). Closure trigger (26) is pivotable toward pistol grip (24) to pivotably actuate upper jaw (54) toward lower jaw (52) and thereby close end effector (50) on tissue. Firing trigger (28) is then pivotable toward pistol grip (24) to fire end effector (50) on the clamped tissue. More specifically, actuation of firing trigger (28) causes firing member (60) to translate distally through end effector (50), including staple cartridge (70), to thereby staple and simultaneously cut the clamped tissue.

As shown in FIGS. 3-5B, staple cartridge (70) includes a cartridge body (72) having an upwardly facing deck (74), an elongate slot (76) extending along a central axis of cartridge body (72) and opening upwardly through deck (74), and a plurality of staple openings (78) (also known as apertures) extending through deck (74) on each side of elongate slot (76). Each staple opening (78) slidably houses an unformed staple (80) and a respective staple driver (82) positioned beneath staple (80). A lower tray (84), also known as a pan, encloses an underside of cartridge body (72) and thereby retains staples (80) and staple drivers (82) within cartridge body (72). A wedge sled (86) is slidably disposed within cartridge body (72) and includes upwardly presented cam surfaces configured to engage the undersides of staple drivers (82).

Figure 5A:
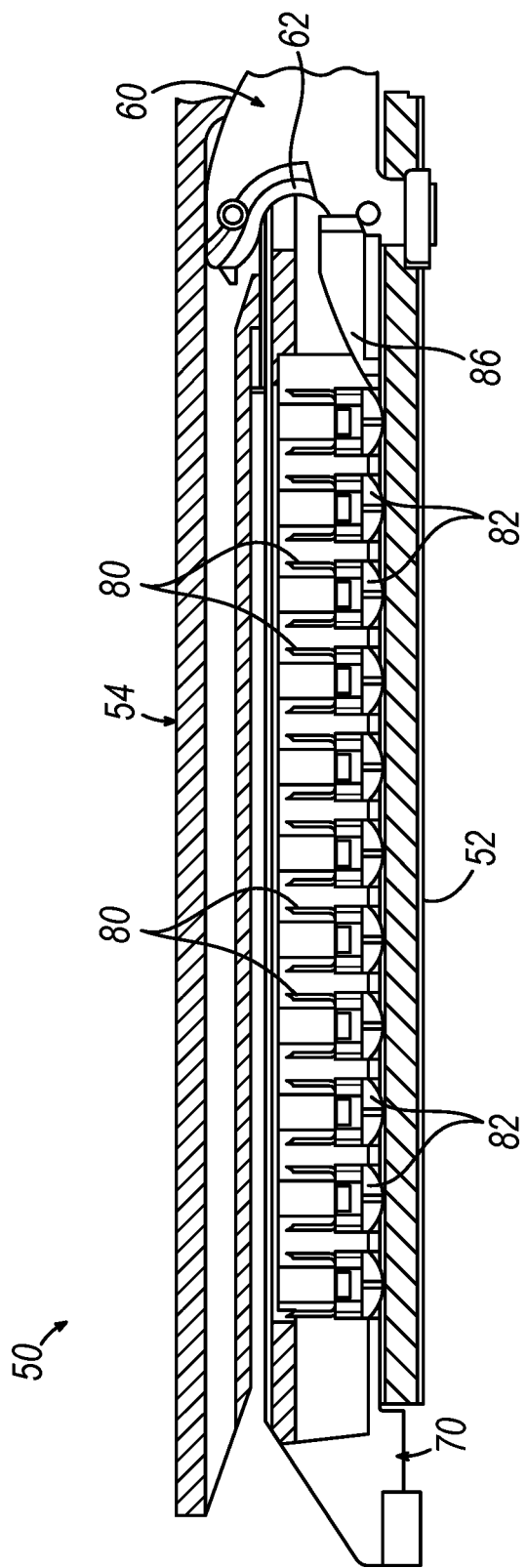
FIG. 5A depicts a side cross-sectional view of the end effector of FIG. 3, taken along line 5-5 of FIG. 3, with a firing member in a proximal position.
Figure 5B:
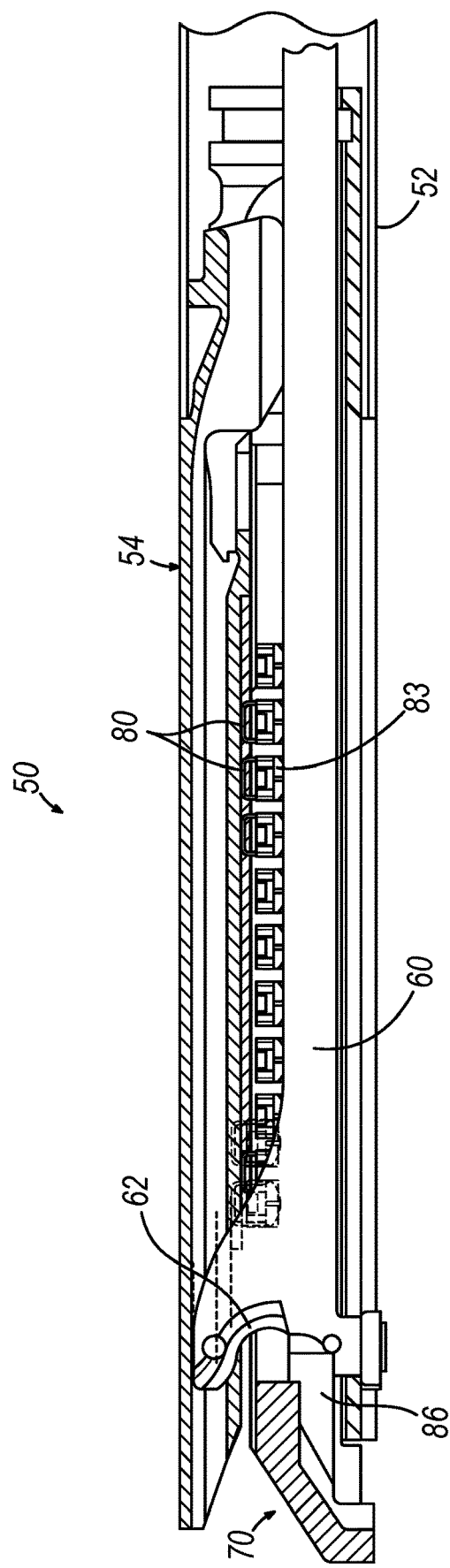
FIG. 5B depicts a side cross-sectional view of the end effector of FIG. 3, taken along line 5-5 of FIG. 3, with the firing member in a distal position.

FIGS. 5A-5B show a firing stroke of surgical stapler (10) during which firing member (60) is actuated distally through end effector (50), including elongate slot (76) of staple cartridge (70). A distal end of firing member (60) drives wedge sled (86) distally to cam staple drivers (82) upwardly and thereby drive the respective staples (80) outwardly from staple openings (78). The legs of staples (80) pass through clamped tissue (not shown) and are then formed by staple forming pockets (58) of anvil (56) (see FIG. 3). Simultaneously, the clamped tissue is severed by cutting edge (62) of firing member (60).

Figure 6:
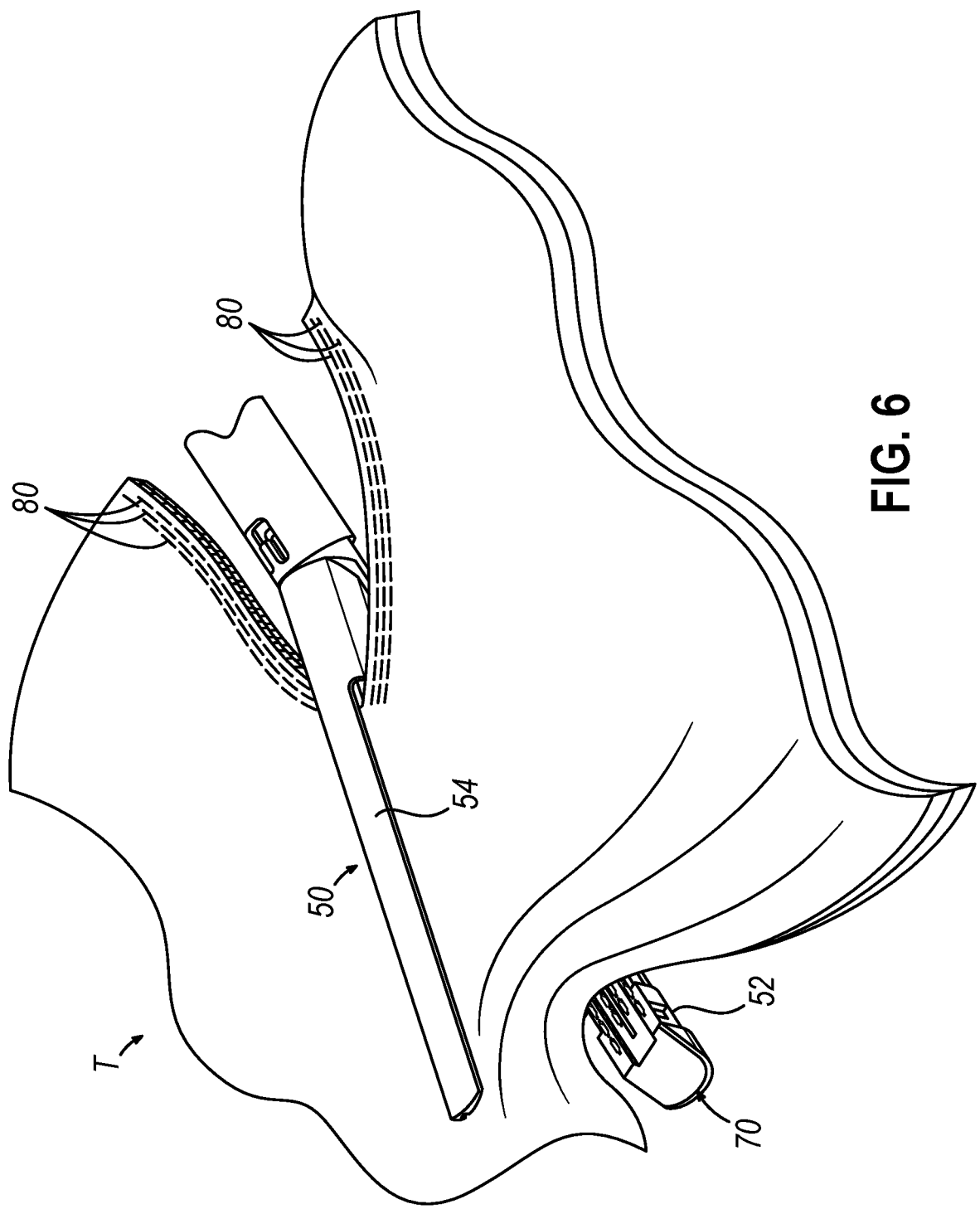
FIG. 6 depicts a perspective view of the end effector of FIG. 3, positioned at tissue and having been fired once in the tissue.

FIG. 6 shows end effector (50) after having been actuated through a single firing stroke through tissue (T). Cutting edge (62) of firing member (60) has cut through tissue (T), and staple drivers (82) have driven three alternating rows of staples (80) through tissue (T) on each side of the cut line produced by cutting edge (62). After the first firing stroke is completed, end effector (50) is withdrawn from the patient, spent staple cartridge (70) is replaced with a new staple cartridge (70), and end effector (50) is then again inserted into the patient to reach the stapling site for further cutting and stapling. This process may be repeated until the desired quantity and pattern of firing strokes across the tissue (T) has been completed.

Surgical stapler (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. Exemplary Buttress Assembly

In some instances, it may be desirable to equip end effector (50) of surgical stapler (10) with an adjunct, also known as a buttress or a tissue thickness compensator, to reinforce the mechanical fastening of tissue provided by staples (80). Such a buttress may prevent the applied staples (80) from pulling through the tissue and may otherwise reduce a risk of tissue tearing at or near the site of applied staples (80). In addition to or as an alternative to providing structural support and integrity to a line of staples (80), a buttress may provide various other kinds of effects such as spacing or gap-filling, administration of therapeutic agents, and/or other effects. In some instances, a buttress may be provided on upper deck (74) of staple cartridge (70). In some other instances, a buttress may be provided on the surface of anvil (56) that faces staple cartridge (70). It should also be understood that a first buttress may be provided on upper deck (74) of staple cartridge (70) while a second buttress is provided on anvil (56) of the same end effector (50).

A. Exemplary Composition of Buttress Assembly

Figure 7:
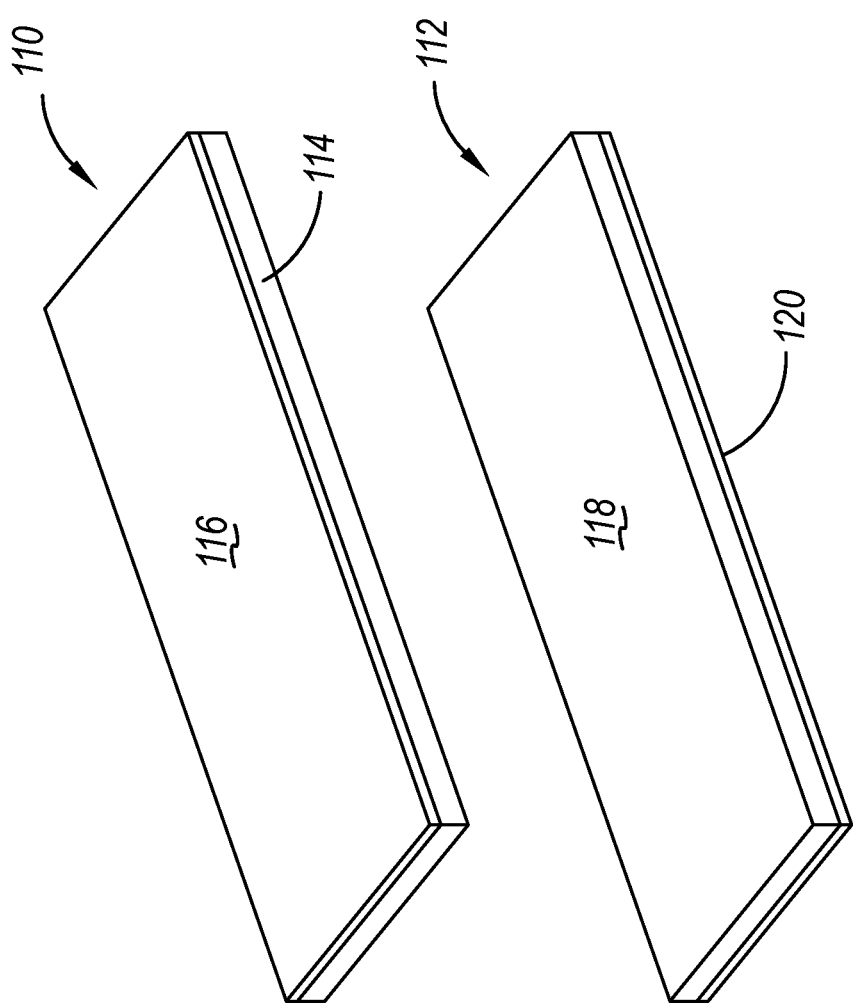
FIG. 7 depicts a perspective view of an exemplary pair of adjuncts in the form of buttress assemblies, each of which may be applied to a jaw of the end effector of FIG. 3.

FIG. 7 shows an exemplary pair of adjuncts in the form of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (80). By way of example only, each buttress body (114, 118) may comprise a mesh of polyglactin 910 material by Ethicon, Inc. of Somerville, New Jersey. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to an underside (124) of anvil (56). Similarly, adhesive layer (120) is provided on buttress body (118) to adhere buttress body (118) to upper deck (74) of staple cartridge (70). Such an adhesive material may provide proper positioning of buttress body (114, 118) before and during actuation of end effector (50); then allow buttress body (114, 118) to separate from end effector (50) after end effector (50) has been actuated, without causing damage to buttress body (114, 118) that is substantial enough to compromise the proper subsequent functioning of buttress body (114, 118).

B. Exemplary Stapling of Tissue with Buttress Assemblies

FIGS. 8A-8C show an exemplary sequence in which surgical stapler end effector (50), which has been loaded with buttress assemblies (110, 112), is actuated to drive staples (80) through two opposed layers of tissue ($T_1$, $T_2$), with buttress assemblies (110, 112) being secured to the same layers of tissue ($T_1$, $T_2$) by staples (80). In particular, FIG. 8A shows layers of tissue ($T_1$, $T_2$) positioned between anvil (56) and staple cartridge (70), with anvil (56) in the open position. Buttress assembly (110) is adhered to underside (124) of anvil (56) via adhesive layer (116); while buttress assembly (112) is adhered to upper deck (74) of staple cartridge (70) via adhesive layer (120). Layers of tissue ($T_1$, $T_2$) are thus interposed between buttress assemblies (110, 112). Next, anvil (56) is closed against staple cartridge (70) such that layers of tissue ($T_1$, $T_2$) are compressed between anvil (56) and staple cartridge (70), with buttress assemblies (110, 112) engaging opposite surfaces of tissue layers ($T_1$, $T_2$). End effector (50) is then fired as described above, driving staple (80) through buttress assemblies (110, 112) and tissue ($T_1$, $T_2$). As shown in FIG. 8C, a crown (122) of driven staple (80) captures and retains buttress assembly (112) against layer of tissue ($T_2$). Deformed legs (126) of staple (80) capture and retain buttress assembly (110) against layer of tissue ($T_1$).

Figure 9:
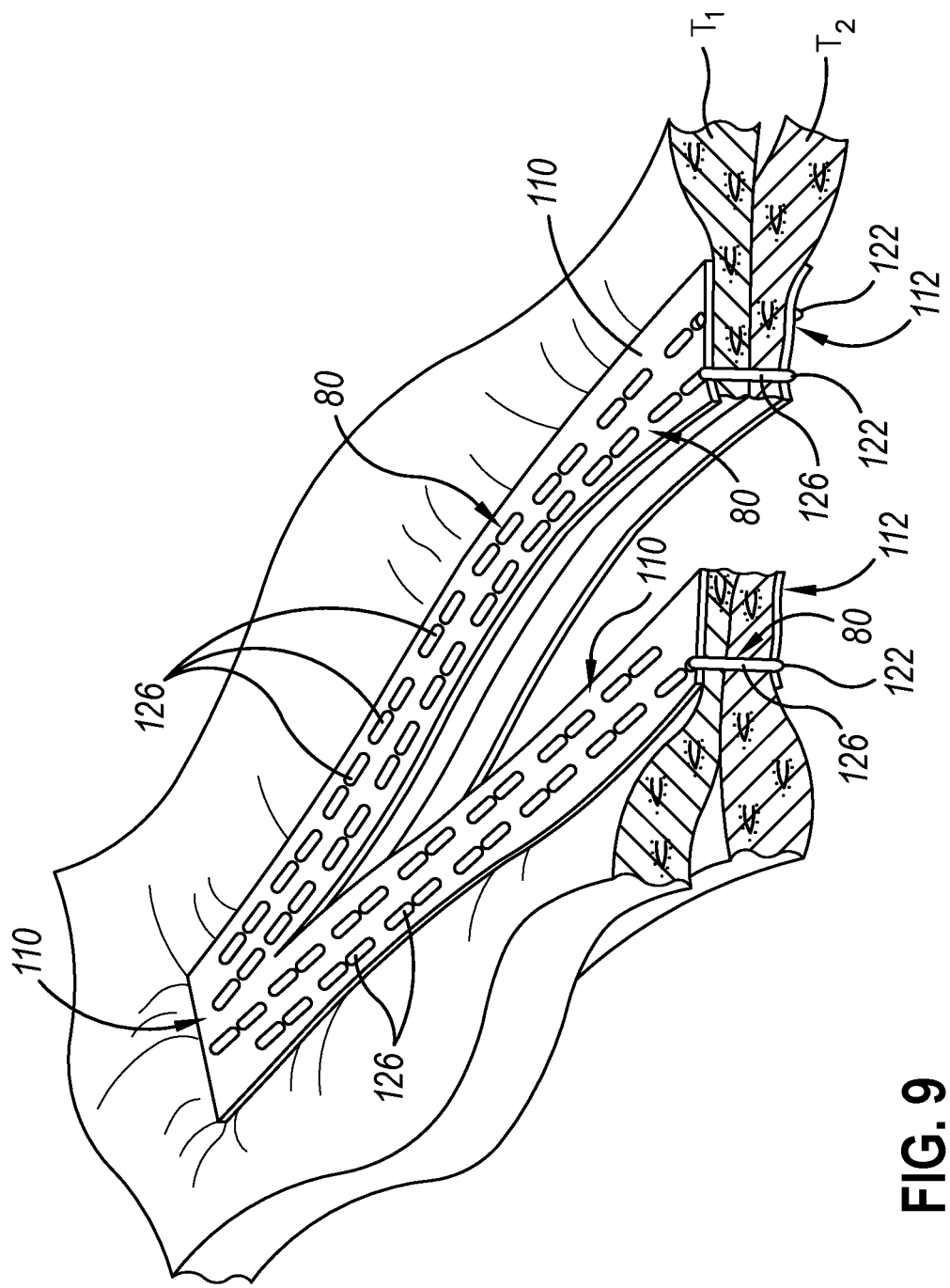
FIG. 9 depicts a perspective view of formed staples and the buttress assemblies of FIG. 8A after having been secured to the tissue by the end effector of FIG. 3.
Figure 10:
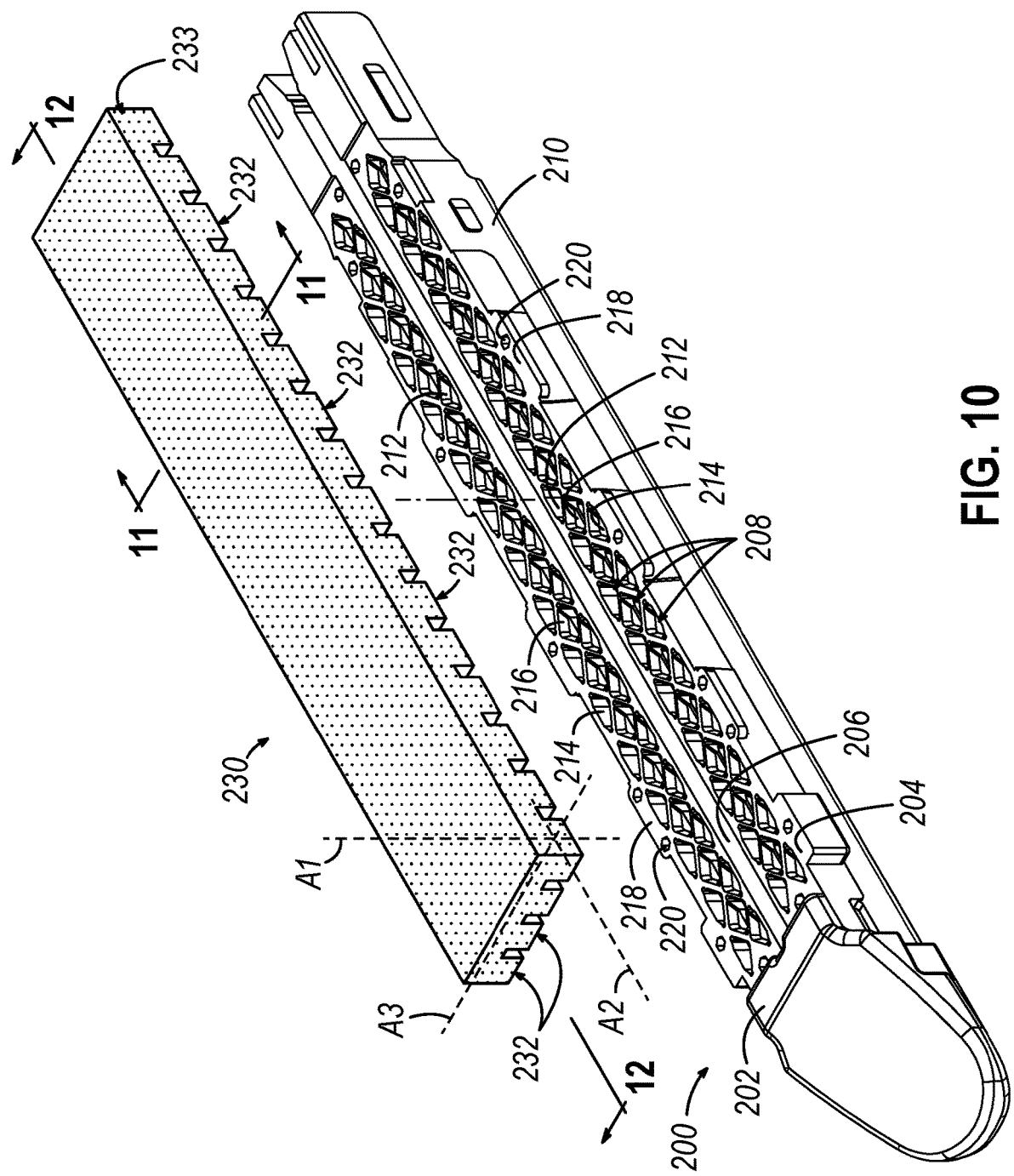
FIG. 10 depicts a perspective view of another exemplary staple cartridge in combination with a first alternative exemplary adjunct.

A series of staples (80) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (50) is pulled away from tissue ($T_1$, $T_2$) after deploying staples (80) and buttress assemblies (110, 112), buttress assemblies (110, 112) disengage end effector such that buttress assemblies (110, 112) remain secured to tissue ($T_1$, $T_2$) with staples (80). Buttress assemblies (110, 112) thus provide structural reinforcement to the lines of staples (80) formed in tissue ($T_1$, $T_2$). As can also be seen in FIG. 9, distally presented cutting edge (62) of firing member (60) also cuts through a centerline of buttress assemblies (110, 112), separating each buttress assembly (110, 112) into a corresponding pair of sections, such that each section remains secured to a respective severed region of tissue ($T_1$, $T_2$).

During use, surgical instrument (10) may be actuated multiple times during a single surgical procedure such that it may be desirable to enable an operator to repeatedly and easily load buttress assemblies (110, 112) onto lower jaw and anvil (16, 18) during that single surgical procedure. Accordingly, it may be desirable to use an adjunct applicator, also referred to as a buttress applier cartridge, to apply buttress assemblies (110, 112) to lower jaw and anvil (16, 18). Exemplary versions of such an applicator are disclosed in U.S. patent application Ser. No. 17/022,520, entitled "Method of Applying Buttress to End Effector of Surgical Stapler," filed Sep. 16, 2020, issued as U.S. Pat. No. 11,660,093 on May 30, 2023, the disclosure of which is incorporated by reference herein.

It will be appreciated that exemplary adjuncts and adjunct applicators may be further configured in accordance with one or more teachings of U.S. Pat. No. 10,166,023, entitled "Method of Applying a Buttress to a Surgical Stapler End Effector," issued Jan. 1, 2019; U.S. Pat. No. 10,349,939, entitled "Method of Applying a Buttress to a Surgical Stapler," issued Jul. 16, 2019; and U.S. Pat. Pub. No. 2012/0080336, entitled "Staple Cartridge Comprising Staples Positioned Within a Compressible Portion Thereof," published Apr. 5, 2012, now abandoned, the disclosures of which are incorporated by reference herein.

III. Exemplary Compressible Adjunct

Figure 11:
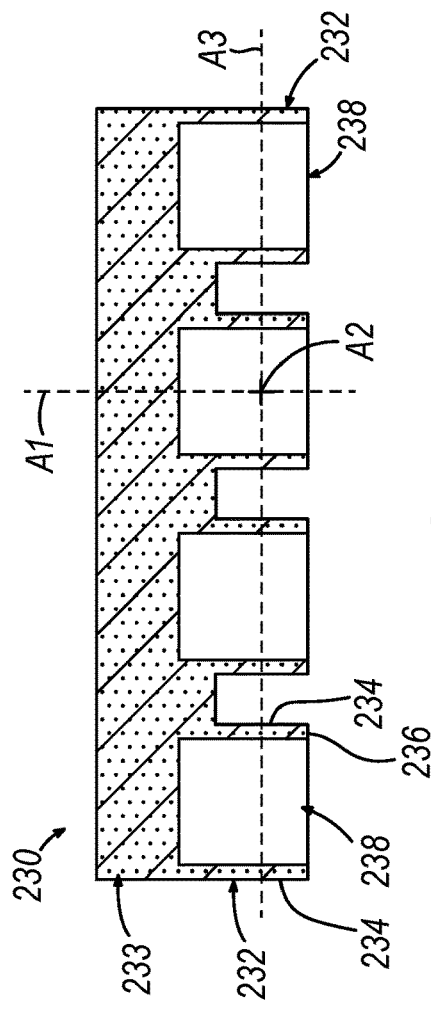
FIG. 11 depicts a cross-sectional view of the adjunct of FIG. 10, taken along line 11-11 of FIG. 10.
Figure 12:
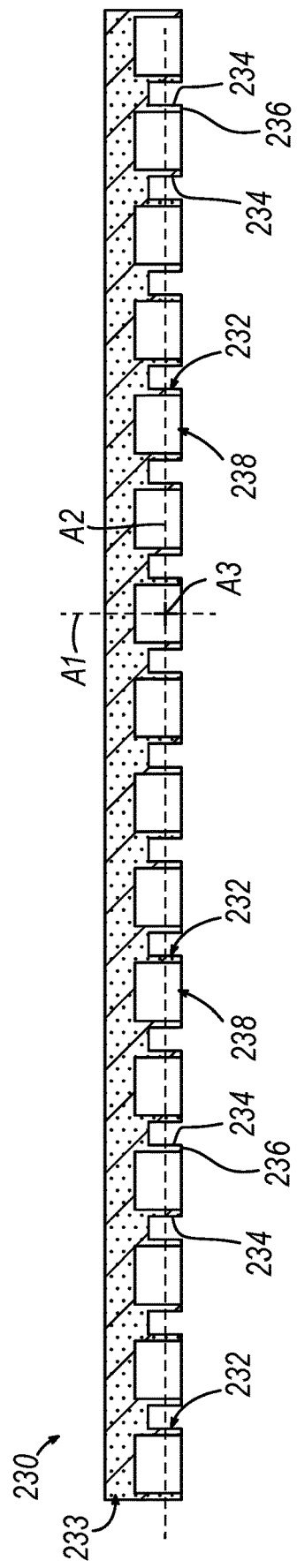
FIG. 12 depicts a cross-sectional view of the adjunct of FIG. 10, taken along line 12-12 of FIG. 10.

In some instances, it may be desirable to employ an adjunct having an enhanced degree of compressibility in a direction orthogonal to the stapling surfaces of end effector (50). Such an adjunct may be configured to apply a compression spring force to stapled tissue consistently along the entire length of the formed staple pattern, thereby ensuring a secure seal of tissue having a thickness that varies along a length of the formed staple pattern and end effector (50). FIGS. 10-12 show an example of such an adjunct (230), also referred to herein as a buttress or cushion, in combination with a staple cartridge (200). Staple cartridge (200) and adjunct (230) are configured for use with end effector (50) and are similar to staple cartridge (70) and buttress assembly (110, 112) described above except as otherwise described below.

It will be appreciated that staple cartridge (200) and/or adjunct (230) may be further configured in accordance with teachings of any one of more the following references, the disclosures of which are incorporated by reference herein: U.S. Pat. No. 10,441,285, entitled "Tissue Thickness Compensator Comprising Tissue Ingrowth Features," issued Oct. 15, 2019; U.S. Pat. No. 10,524,788, entitled "Compressible Adjunct with Attachment Regions," issued Jan. 7, 2020; U.S. Pat. No. 10,568,621, entitled "Surgical Staple Buttress with Integral Adhesive for Releasably Attaching to a Surgical Stapler," issued Feb. 25, 2020; U.S. Pat. No. 10,588,623, entitled "Adhesive Film Laminate," issued Mar. 17, 2020; U.S. Pat. No. 10,624,861, entitled "Tissue Thickness Compensator Configured to Redistribute Compressive Forces," issued Apr. 21, 2020; U.S. Pat. No. 10,667,808, entitled "Staple Cartridge Comprising an Absorbable Adjunct," issued Jun. 2, 2020; U.S. Pat. No. 10,945,731, entitled "Tissue Thickness Compensator Comprising Controlled Release and Expansion," issued Mar. 16, 2021; U.S. Pat. No. 10,966,722, entitled "Adjunct Materials and Methods of Using Same in Surgical Methods for Tissue Sealing," issued Apr. 6, 2021; U.S. Pat. No. 11,058,425, entitled "Implantable Layers for a Surgical Instrument," issued Jul. 13, 2021; and U.S. Pat. Pub. No. 2019/0200978, entitled "Tissue Ingrowth Materials and Method of Using the Same," published Jul. 4, 2019, issued as U.S. Pat. No. 11,219,451 on Jan. 11, 2022.

As shown in FIG. 10, staple cartridge (200) includes a cartridge body (202) having an upwardly facing deck (204), an elongate slot (206) extending along a central axis of cartridge body (202) and opening upwardly through deck (204), and a plurality of staple openings (208) extending through deck (204) on each side of elongate slot (206). Each staple opening (208) slidably houses an unformed staple (not shown), similar to staple (80), and a respective staple driver (not shown), similar to staple driver (82), configured to drive the staple outwardly toward anvil (56) to be formed. A lower tray (210) of staple cartridge (200) retains the staples and staple drivers within cartridge body (202).

Cartridge body (202) of the present example further includes a plurality of upwardly-opening recesses (212, 214, 216) formed in deck (204) and having base surfaces through which staple openings (208) extend. More specifically, on each side of elongate slot (206), deck (204) includes an inner row of triangular recesses (212) each having a medial apex that points transversely away from elongate slot (206); an outer row of triangular recesses (214) each having a medial apex that points transversely toward elongate slot (206); and a middle row of diamond-shaped recesses (216) each having an inner medial apex that points transversely toward elongate slot (206) and an opposed outer medial apex that points transversely away from elongate slot (206). Recesses (212, 214, 216) may cooperate to more securely grip and thereby stabilize clamped tissue during stapling and cutting of the clamped tissue.

Cartridge body (202) of the present example further includes a plurality of elongate tabs (218) projecting laterally outwardly from deck (204) on each lateral side of cartridge body (202). Tabs (218) of the present example are spaced apart from one another in a longitudinal direction, and each tab (218) has a generally rounded rectangular shape. Cartridge body (202) further includes a plurality of attachment openings (220) spaced apart from one longitudinally on each side of elongate slot (206), with each attachment opening (220) being smaller than a staple opening (208) and having a hexagonal shape. In the present version, each tab (218) includes at least one attachment opening (220). Attachment openings (220) may be configured to facilitate releasable attachment of an adjunct, such as adjunct (230), to staple cartridge deck (204).

Adjunct (230) has a plurality of sub-structures in the form of three-dimensional, resiliently compressible (or collapsible) nodules (232) that define a lower portion of adjunct (230) and are integrally connected with one another, via an upper portion (233) of adjunct (230), in a plurality of linear arrays defining a lattice structure having an elongate rectangular shape.

Each nodule (232) of the present example has a generally cuboid shape defining four side surfaces (234), a lower surface (236), and an opening (238) in lower surface (236) that extends along a vertical central axis (A1) of nodule (232) and defines an open, hollow interior of nodule (232). Additionally, each nodule (232) is symmetrical about its centroid along a second axis (A2) of nodule (232) that extends horizontally in a proximal-distal direction parallel to the length of adjunct (230), and along a third axis (A3) of nodule (232) that extends horizontally in a direction traverse to the length of adjunct (230), where each axis (A1, A2, A3) extends through the centroid.

Adjunct (230) may be formed of an elastic, bioabsorbable polymeric material having a suitable degree of elasticity that enables adjunct (230) to compress and resiliently resume its original shape. In the present example, each nodule (232) of adjunct (230) is resiliently compressible in such a manner along at least each of its three axes (A1, A2, A3).

IV. Exemplary Buttress Applier Cartridge with Active Retainer Arms

Figure 13A:
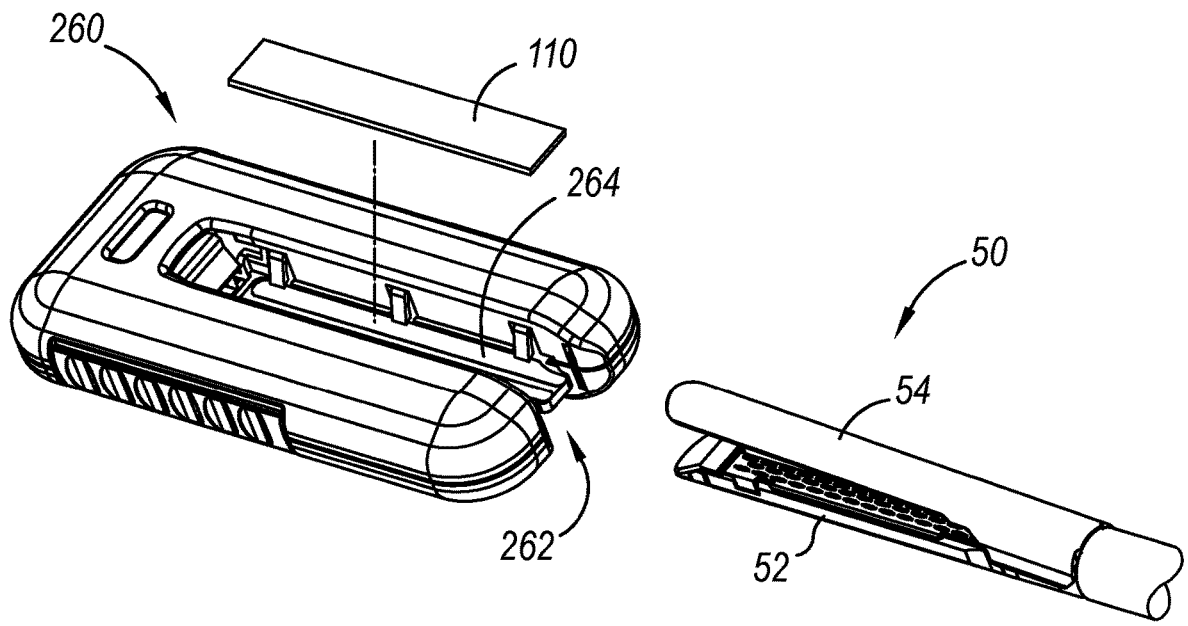
FIG. 13A depicts a perspective view of the end effector of FIG. 3 and an exemplary buttress applier cartridge that may be used to carry and apply the buttress assemblies of FIG. 7, showing the end effector and the buttress applier cartridge being aligned with one another.
Figure 13B:
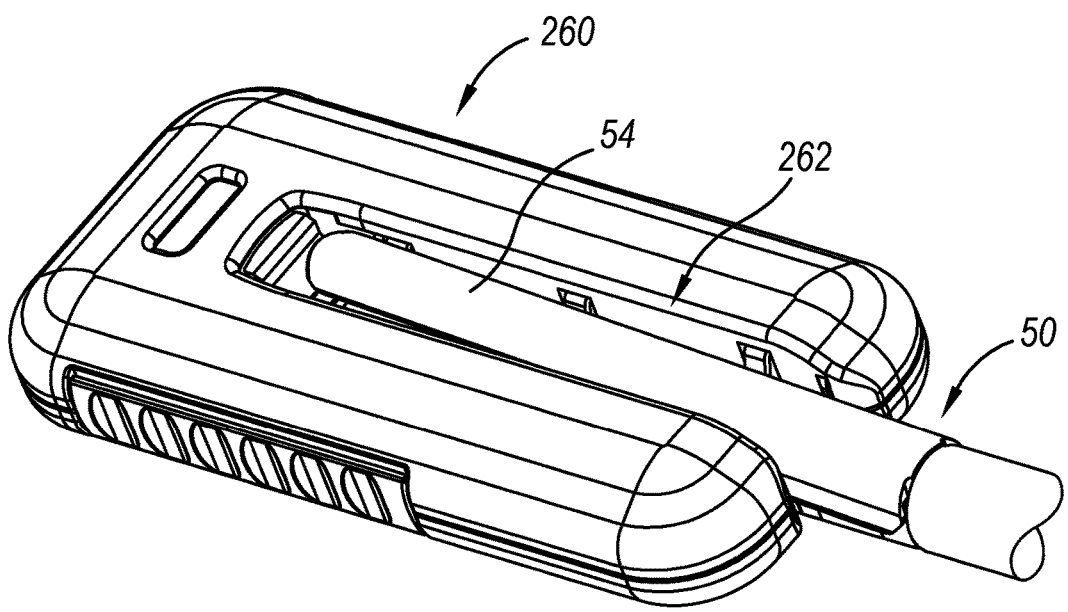
FIG. 13B depicts a perspective view of the end effector of FIG. 3 and the buttress applier cartridge of FIG. 13A, with the end effectors jaws closed on a platform of the buttress applier cartridge.

Because end effector (12) of surgical instrument (10) may be actuated multiple times during a single surgical procedure, it may be desirable to enable an operator to repeatedly and easily load buttress assemblies (110, 112) onto end effector jaws (52, 54) during that single surgical procedure. FIGS. 13A-13B show an exemplary buttress applier cartridge (260) (also referred to as a "buttress applicator") that may be used to support, protect, and apply adjunct material, such as buttress assemblies (110, 112), to end effector (12). Cartridge (260) of this example comprises an open end (212) defining a U-shaped recess configured to receive end effector (12), and a platform (264) located within the U-shaped recess. Platform (264) is configured to temporarily support a buttress (110, 112) on each side such that lower and upper jaws (52, 54) may grasp platform (264), thereby suitably attaching buttresses (110, 112) to respective jaw (52, 54) for use in accordance with the description herein. It will be appreciated that cartridge (260) may be further configured in accordance with the teachings of U.S. patent application Ser. No. 17/462,451, entitled "Surgical Stapler Buttress with Variable Length Feature," filed on Aug. 31, 2021, issued as U.S. Pat. No. 11,857,190 on Jan. 2, 2024, the disclosure of which is incorporated by reference herein.

V. Exemplary Alternative Adjuncts, End Effectors, and Means of Deploying Adjuncts In some instances, it may be desirable to provide an adjunct or a combination of adjuncts configured to guide staples (80) being driven into staple forming pockets (58) while also accommodating tissue having varying thickness along the length of the formed staple pattern. Additionally, or alternatively, it may be desirable to provide an adjunct or combination of adjuncts configured to accommodate tissue having varying thickness along the length of the formed staple pattern, while also inhibiting an undesirable amount of tissue movement relative to anvil (56) and upwardly facing deck (74) in response to jaws (52, 54) grasping tissue. In some instances, it may be desirable to provide an end effector with an adjunct or combination of adjuncts capable of severing and stapling tissue to form a suitable and secure seal of tissue without forming a traditional "B" shaped staple. In some instances, it may be desirable to attach an adjunct to a targeted tissue prior to severing and stapling tissue. In some instances, it may be desirable to have an adjunct that varies in thickness along the length of adjunct. In some instances, it may be desirable to provide an adjunct that resists lateral movement relative to the associated anvil (56) or upwardly facing deck (74) to which the adjunct is initially attached to prior to firing of end effector (50). Further, in some instances, it may be desirable to utilize an adjunct in medical procedures other than severing and stapling tissue, such as for wound care to prevent wound dehiscence.

Exemplary versions of such adjuncts, combinations of adjuncts, and/or end effectors are described in greater detail below. Unless otherwise described, it will be appreciated that such features may be applied to a multi-layer adjunct similar to buttress assemblies (110, 112) described above in connection with FIGS. 7-9, or alternatively to a compressible monolithic adjunct similar to adjunct (230) described above in connection with FIGS. 10-12.

A. Exemplary Adjunct Pairs with Staple Guidance Feature Associated with Staple Deck In some instances, while utilizing a buttress assembly (110, 112) or adjunct (230), the thickness of buttress assembly (110, 112) and/or adjunct (230) may lead to an increase in distance between upwardly facing deck (74) (sometimes referred to as the "staple deck") and anvil (56) while jaws (52, 54) are suitably closed in order to compress tissue ($T_1$, $T_2$) in accordance with the teachings herein. In other words, in order to suitably accommodate for buttress assembly (110, 112), the staple deck (74) may be spaced further away from anvil (56) in a direction orthogonal to the stapling surfaces of end effector (50) while jaws (52, 54) are suitably closed as compared to instances when buttress assemblies (110, 112) and/or adjuncts (230) are not incorporated. The increase in distance between staple deck (74) and anvil (56) may require a fired stapled (80) to travel a further distance between opening (78) and staple forming pocket (58), which may inadvertently affect the quality of "B" formation of the fired staple. Therefore, in some instances, it may be desirable to retain the benefits of buttress assembly (110, 112) and/or adjunct (230), while also suitably guiding staples (80) into staple forming pockets (58) to help ensure a quality "B" formation of a fired staple.

FIGS. 14A-14D show surgical stapler end effector (50) loaded with a cartridge-side buttress assembly (300) and an anvil-side buttress assembly (302). Further, FIGS. 14A-14D show an exemplary sequence in which surgical stapler end effector (50) is actuated to drive staples (80) through two opposed layers of tissue ($T_1$, $T_2$), with buttress assemblies (300, 302) being secured to the same layers of tissue ($T_1$, $T_2$) by staples (80). As will be described in greater detail below, cartridge-side buttress assembly (300) is configured to receive legs (126) during the firing process of staple (80) such that legs (126) penetrate cartridge-side buttress assembly (300), thereby allowing contact between cartridge-side buttress assembly (300) and legs (126) to guide legs (126) into suitable contact with a respective staple forming pocket (58), which in turn may enhance the quality and consistency of the "B" formation of the fired staple (80).

Anvil-side buttress assembly (302) includes a buttress body (308) and an adhesive layer (310). Adhesive layer (310) is provided on buttress body (308) to adhere buttress body (308) to anvil (56). Such an adhesive material may provide proper positioning of buttress body (308) before and during actuation of end effector (50); then allow buttress body (308) to separate from end effector (50) after end effector (50) has been actuated, without causing damage to buttress body (308) that is substantial enough to compromise the proper subsequent functioning of buttress body (308). In some instances, anvil-side buttress assembly (302) is attached to anvil (56) via buttress applier cartridge (260). In other instances, anvil-side buttress assembly (302) may be attached to anvil (56) during manufacturing of end effector (50).

Buttress body (308) of anvil-side buttress assembly (302) may be substantially similar to buttress body (114) and/or adjunct (230) described above. Therefore, anvil-side buttress assembly (302) may be configured to provide structural reinforcement to the lines of staples (80) formed in tissue ($T_1$, $T_2$). Additionally, or alternatively, anvil-side buttress assembly (302) may be configured to apply a compression spring force to stapled tissue consistently along the entire length of the formed staple pattern, thereby ensuring a secure seal of tissue having a thickness that varies along a length of the formed staple pattern and end effector (50). It should be understood that anvil-side buttress assembly (302) may be configured to provide any other suitable benefit as would be apparent to one skilled in the art in view of the teachings herein.

Cartridge-side buttress assembly (300) includes a buttress body (304) and an adhesive layer (306). Adhesive layer (306) is provided on buttress body (304) to adhere buttress body (304) to staple deck (74). Such an adhesive material may provide proper positioning of buttress body (304) before and during actuation of end effector (50); then allow buttress body (304) to separate from end effector (50) after end effector (50) has been actuated, without causing damage to buttress body (304) that is substantial enough to compromise the proper subsequent functioning of buttress body (304).

Buttress body (304) is thinner and much stiffer compared to buttress body (308) of anvil-side buttress assembly (302). Buttress body (304) may offer very little compression in response to grasping tissue ($T_1$, $T_2$) as compared to buttress body (308) described above. The stiffness of buttress body (304) may enable cartridge-side buttress assembly (300) to distribute loads from staple deck (74) onto grasped tissue ($T_1$, $T_2$) during exemplary use of end effector (50) in accordance with the description herein.

Buttress body (304) may be suitably compliable such that staple legs (126) may penetrate buttress body (304) during firing of staples (80), but also suitably rigid such that the penetrated portions of buttress body (304) guide staple legs (126) toward their respective staple forming pocket (58) during the firing process. Therefore, as staple legs (126) are actuated upward via staple driver (82), newly penetrated portions of buttress body (304) may inhibit staple legs (126) from deviating away from their intended firing path during the firing process. Therefore, incorporation of buttress body (304) onto staple deck (74) enhances the quality and consistency of the "B" formation of the fired staple.

Buttress body (304) may comprise a thin piece of plastic or any other suitable material as would be apparent to one skilled in the art in view of the teachings herein. Buttress body (304) is positioned on top staple deck (74) such that buttress body (304) covers staple openings (78), thereby preventing staples (80) housed within staple openings (78) from inadvertently escaping staple openings (78) prior to the firing process.

FIGS. 14A-14C show an exemplary sequence of surgical stapler end effector (50), which has been loaded with buttress assemblies (300, 302), being actuated to drive staples (80) through two opposed layers of tissue ($T_1$, $T_2$) such that buttress assemblies (300, 302) are secured to tissue ($T_1$, $T_2$) by staples (80). In particular, FIG. 14A shows layers of tissue ($T_1$, $T_2$) positioned between anvil (56) and staple cartridge (70), with anvil (56) in the open position. Buttress assembly (302) is adhered to anvil (56) via adhesive layer (310); while buttress assembly (300) is adhered to upper deck (74) of staple cartridge (70) via adhesive layer (306). Layers of tissue ($T_1$, $T_2$) are thus interposed between buttress assemblies (300, 302). Next, as shown in FIG. 14B, anvil (56) is closed against staple cartridge (70) such that layers of tissue ($T_1$, $T_2$) are compressed between anvil (56) and staple cartridge (70), with buttress assemblies (302, 300) engaging opposite surfaces of tissue layers ($T_1$, $T_2$). End effector (50) is then fired as described above. As shown in FIG. 14C, staple driver (82) is driven upward, thereby actuating staple legs (126) to initially penetrate buttress body (304) of cartridge-side buttress assembly (300). After initial penetration of buttress body (304), contact between staple legs (126) and buttress body (304) guides staple legs (126) toward their respective staple forming pocket (58), thereby inhibiting staple legs (126) from missing their intended contact location with staple forming pocket (58). As shown in FIG. 14D, a crown (122) of driven staple (80) captures and retains buttress assembly (300) against layer of tissue ($T_2$). Deformed legs (126) of staple (80) capture and retain buttress assembly (302) against layer of tissue ($T_1$). Therefore, the combination of using anvil-side buttress assembly (302) and cartridge side buttress assembly (300) provides the benefits of buttress assemblies (100, 112) and/or adjunct (230) describe above, while also enhancing the "B" formation of fired staples.

B. Exemplary Adjuncts with Localized Stiffness

In some instances, while closing jaws (52, 54) to compress tissue ($T_1$, $T_2$) in accordance with the teachings herein, tissue ($T_1$, $T_2$) may undesirably move (otherwise known as "tissue flow") away from the surfaces of staple deck (74) and/or anvil (56) intended to engage tissue ($T_1$, $T_2$) during the severing and stapling of tissue ($T_1$, $T_2$) in accordance with the description herein. If the amount of tissue flow away from the surface of staple deck (74) and/or anvil (56) is too great, the structural integrity of stapled tissue ($T_1$, $T_2$) may be inadvertently reduced. Therefore, it may be desirable to have a buttress assembly configured to inhibit an undesirable amount of tissue flow. Additionally, or alternatively, it may be desirable to also suitably guide staples into contact with staple forming pockets (58) to help ensure a quality "B" formation of a fired staple.

Figure 15:
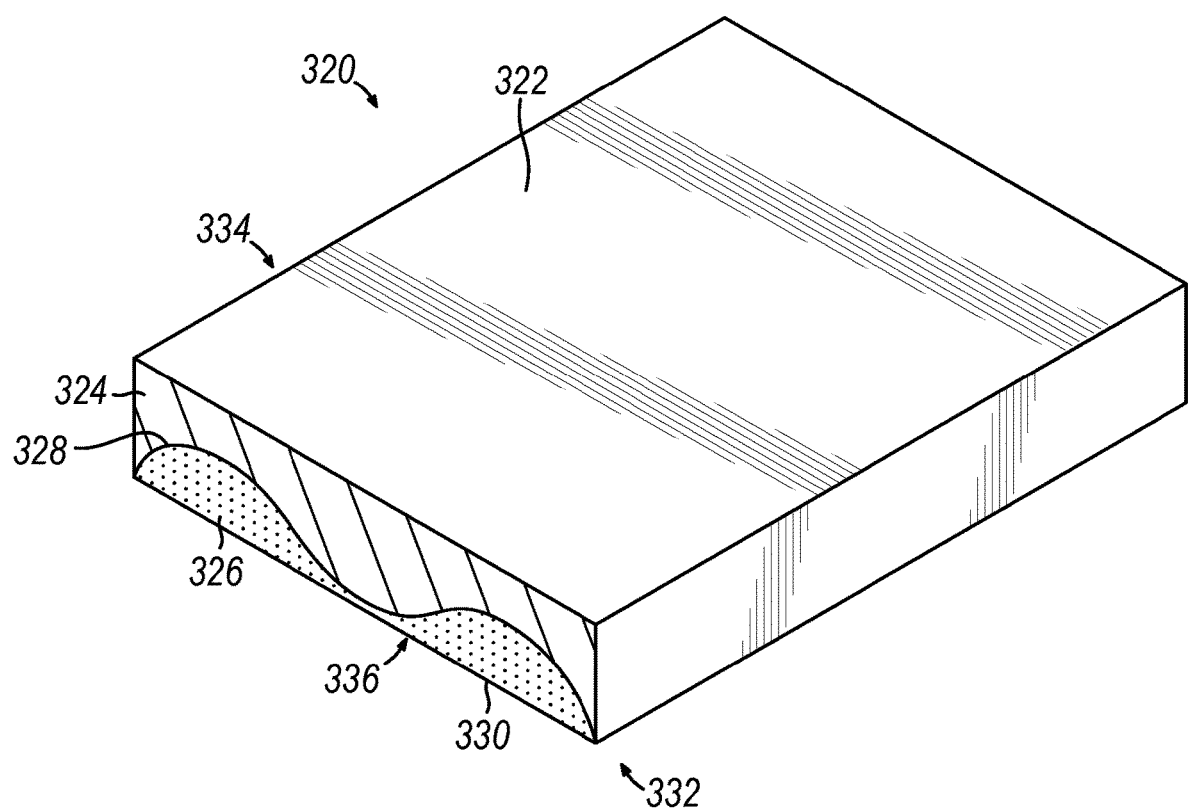
FIG. 15 depicts a perspective view of an alternative buttress assembly.
Figure 16:
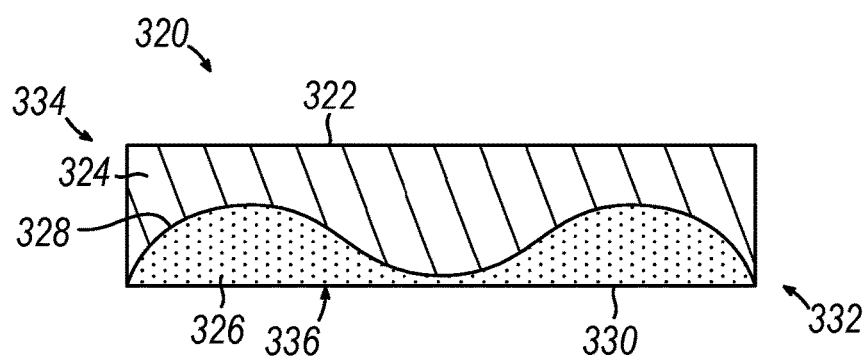
FIG. 16 depicts an elevational front view of the buttress assembly of FIG. 15.
Figure 17:
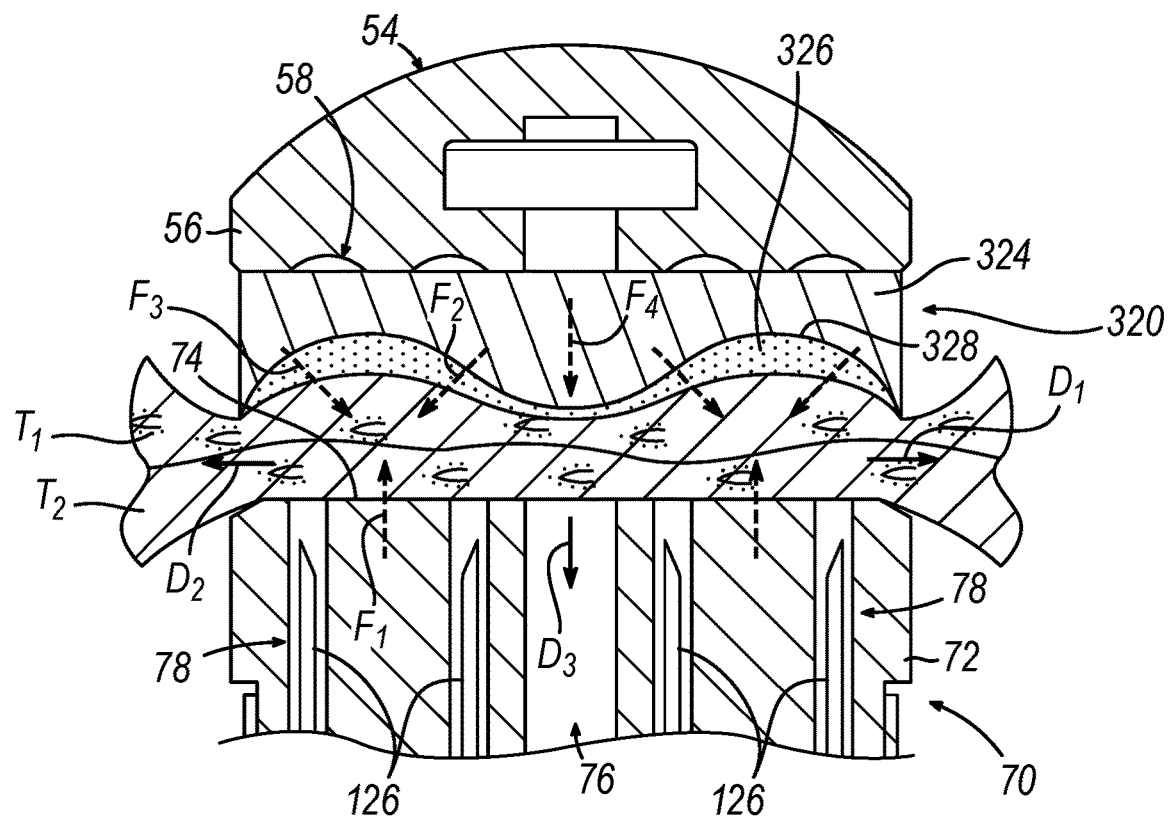
FIG. 17 depicts a cross-sectional end view of a portion of the end effector of FIG. 3 with the buttress assembly of FIG. 15 attached to the anvil of the end effector, showing the end effector jaws in a closed state on tissue.

FIGS. 15-17 show an exemplary buttress assembly (320) that may be loaded onto end effector (50) in replacement of buttress assemblies (110, 112, 300, 302) or adjunct (230) described above. As will be described in greater detail below, buttress assembly (320) is configured to provide the benefits of buttress assembly (110, 112) and/or adjunct (230) described above, and also deform in reaction to end effector (50) grasping tissue ($T_1$, $T_2$) to impart multiple forces (F2, F3) with opposing lateral components on tissue ($T_1$, $T_2$) in order to control excessive tissue flow in multiple directions ($D_1$, $D_2$, $D_3$).

Buttress assembly (320) includes an adhesive layer (322), a top rigid member (324), and a bottom flexible member (326). Adhesive layer (322) is associated with a top portion of rigid member (324). Adhesive layer (322) is provided on rigid member (324) to adhere buttress assembly (320) to anvil (56). Such an adhesive material may provide proper positioning of rigid member (324) and flexible member (326) before and during actuation of end effector (50); then allow rigid member (324) and flexible member (326) to separate from end effector (50) after end effector (50) has been actuated, without causing damage to rigid member (324) and flexible member (326) that is substantial enough to compromise the proper subsequent functioning of buttress assembly (320). In some instances, buttress assembly (320) is attached to anvil (56) via buttress applier cartridge (260). In other instances, buttress assembly (320) may be attached to anvil (56) during manufacturing of end effector (50). It should be understood that in the current example, buttress assembly (320) is attached to anvil (56), this is merely optional, as buttress assembly (320) may be attached to staple deck (74).

Flexible member (326) includes a tissue engagement surface (330) configured to directly engage tissue ($T_1$, $T_2$) is response to jaws (52, 54) grasping tissue ($T_1$, $T_2$) in accordance. Flexible member (326) may be made from the same material as buttress bodies (114, 118) or adjunct (230) described above. Therefore, flexible member (326) is configured to suitably deform in response to jaws (52, 54) grasping tissue ($T_1$, $T_2$) in accordance with the description herein. However, rigid member (324) is suitably stiff such that rigid member (324) retains its intended shape in response to jaws (52, 54) grasping tissue ($T_1$, $T_2$). While rigid member (324) is suitably rigid to retain its intended shape in response to jaws (52, 54) grasping tissue ($T_1$, $T_2$), rigid member (324) is also configured to be penetrated by staples (80) such that legs (126) of staples may suitably engage staple forming pockets (58) to attach tissue ($T_1$, $T_2$) and buttress assembly (320) together in response to suitably firing end effector (50) in accordance with the teachings herein.

Top rigid member (324) and bottom flexible member (326) are coupled to each other at a complementary contoured surfaced (328). Complementary contour surface (328) extends laterally between first lateral section (332) and second lateral section (334), with a central portion (336) interposed between lateral sections (332, 334). As best shown in FIG. 17, central portion (336) is directly adjacent to elongate slot (76) of staple cartridge (70); while first lateral section (332) is directly adjacent to a first half of staple deck (74) and second lateral section (334) is directly adjacent to a second half of staple deck (74). The portions of rigid member (324) forming complementary contour surface (328) at lateral sections (332, 334) have a concave profile, while the portion of rigid member (324) forming complementary contour surface (328) at central portion (336) has a convex profile.

The concave portions of rigid member (324) forming complementary contour surface (328) are configured to inhibit an undesirable amount of tissue flow in multiple directions ($D_1$, $D_2$, $D_3$). Therefore, flexible member (326) deforms in response to staple deck (74) and tissue engagement surface (330) of flexible member (326) grasping tissue ($T_1$, $T_2$). In particular, the upward force (F1) acting on tissue ($T_1$, $T_2$) causes flexible member (326) to suitably deform, which may therefore provide similar benefits compared to buttress assemblies (110, 112) and/or adjunct (230) described above. Since rigid member (324) does not suitably deform, portions of rigid member (324) forming lateral contoured surface (328) impart downward and lateral forces (F2, F3) on tissue ($T_1$, $T_2$). Downward-lateral forces (F2, F3) include lateral components facing in opposite directions of one another. The opposite lateral components of forces (F2, F3) inhibit an undesirable amount of grasped tissue ($T_1$, $T_2$) from moving off of staple deck (74) in directions ($D_1$, $D_2$, $D_3$) shown above. Central portion (336) imparts a downward force (F4) such that some grasped tissue ($T_1$, $T_2$) is driven into elongate slot (76). Therefore, flexible member (326) of buttress assembly (320) is configured to provide the above-described benefits of buttress assembly (110, 112) and/or adjunct (230); while rigid member (324) and the geometry of complementary contoured surface (328) are configured to inhibit an undesirable amount of tissue flow in directions ($D_1$, $D_2$, $D_3$).

Figure 18:
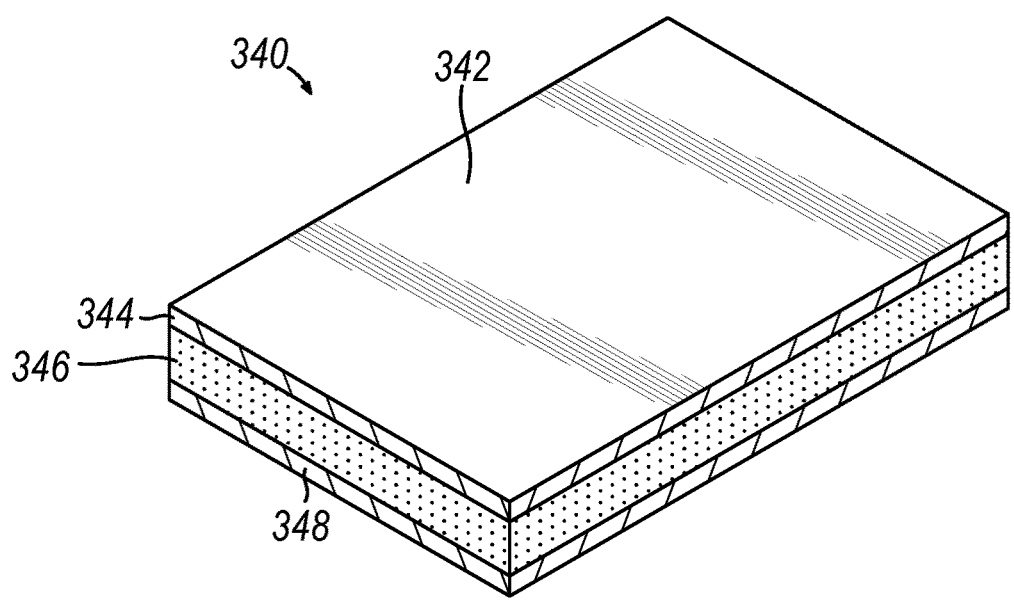
FIG. 18 depicts a perspective view of an alternative buttress assembly.
Figure 19:
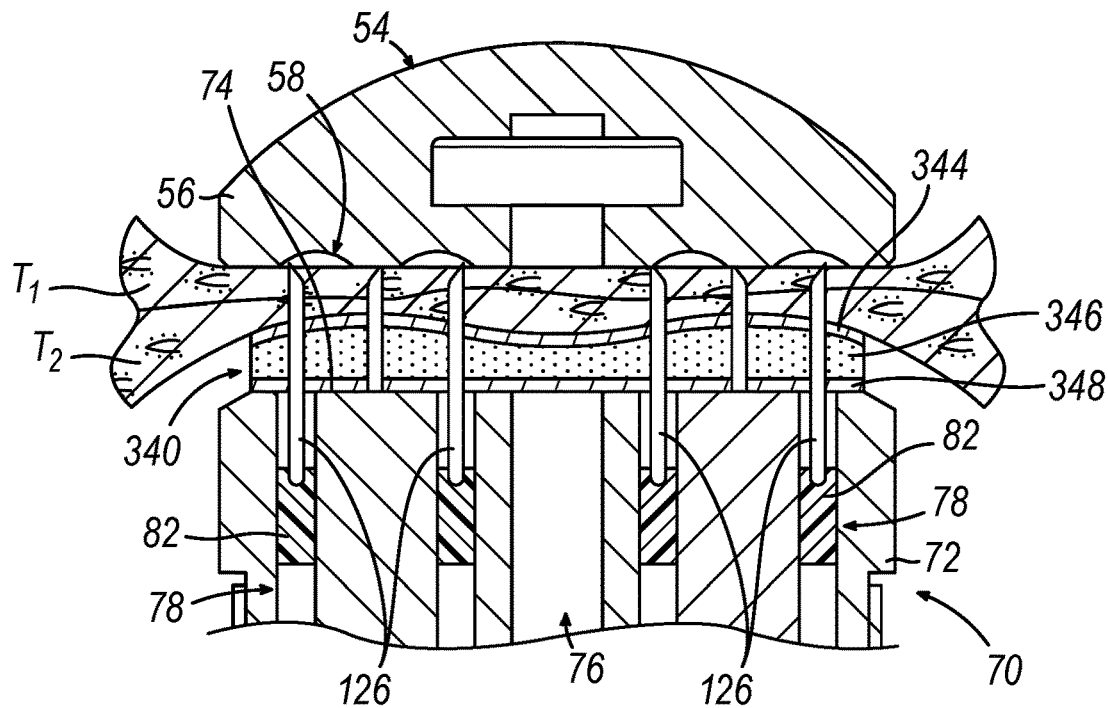
FIG. 19 depicts a cross-sectional end view of a portion of the end effector of FIG. 3 with the buttress assembly of FIG. 18 attached to the staple cartridge of the end effector, showing partially fired staples while the end effector jaws are in a closed state on the tissue.
Figure 21:
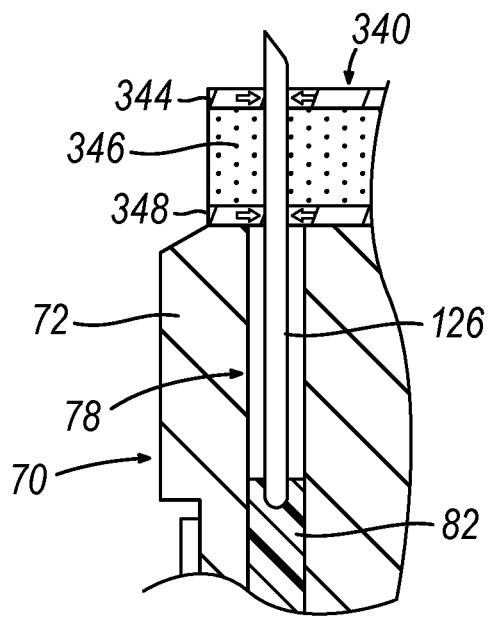
FIG. 21 depicts an enlarged cross-sectional end view of a staple being partially fired through the buttress assembly of FIG. 18.

FIGS. 18-19 and 21 show an exemplary buttress assembly (340) that may be loaded onto end effector (50) in replacement of buttress assemblies (110, 112, 300, 302, 320) or adjunct (230) described above. As will be described in greater detail below, buttress assembly (320) is configured to provide the benefits of buttress assembly (110, 112) and/or adjunct (230) described above, while also suitably guiding staples (80) into staple forming pockets (58) to help ensure a quality "B" formation of a fired staple.

Buttress assembly (340) includes an adhesive layer (342), a lower rigid member (344), a middle flexible member (346), and an upper rigid member (348). Adhesive layer (342) is associated with a top portion of lower rigid member (344). Adhesive layer (342) is provided on rigid member (344) to adhere buttress assembly (340) to staple deck (74). Such an adhesive material may provide proper positioning of rigid members (344, 348) and flexible member (346) before and during actuation of end effector (50); then allow rigid members (344, 348) and flexible member (346) to separate from end effector (50) after end effector (50) has been actuated, without causing damage to rigid members (344, 348) and flexible member (346) that is substantial enough to compromise the proper subsequent functioning of buttress assembly (340). In some instances, buttress assembly (340) is attached to staple deck (74) via buttress applier cartridge (260). In other instances, buttress assembly (320) may be attached to staple deck (74) during manufacturing of end effector (50). It should be understood that in the current example, buttress assembly (340) is attached to staple deck (74), this is merely optional, as buttress assembly (340) may be attached to anvil (56).

Flexible member (346) is interposed between rigid members (344, 348). Flexible member (326) may be made from the same material as buttress bodies (114, 118) or adjunct (230) described above. Therefore, flexible member (326) is configured to suitably deform in response to jaws (52, 54) grasping tissue ($T_1$, $T_2$) in accordance with the description herein. As shown in FIG. 19, upper rigid member (348) may also be configured to flex in response to jaws (52, 54) grasping tissue ($T_1$, $T_2$) in accordance with the description herein.

Figure 20:
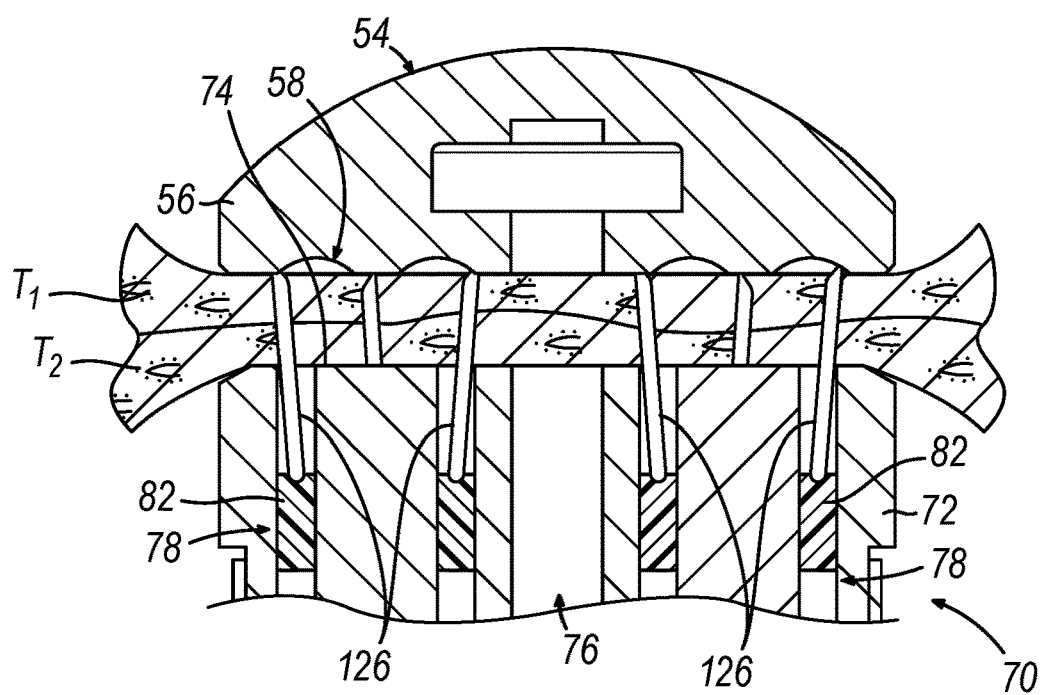
FIG. 20 depicts a cross-sectional end view of a portion of the end effector of FIG. 3 with the buttress assembly attached to the staple cartridge, showing partially fired staples while the end effector jaws are in a closed state on the tissue.

However, as shown in FIGS. 19 and 21, rigid members (344, 348) rigid are suitably rigid in order to help guide staple legs (126) into suitable contact with staple forming pockets (58) in similar fashion to buttress body (304) of buttress assembly (300) described above. FIG. 20 shows an exemplary firing of staples (80) without the use of a buttress assembly (340); such that staple legs (126) deviate from their intended firing path and fail to suitably contact staple forming pockets (58) to form a suitable "B" shaped staple.

Since buttress assembly (340) incorporated both rigid members (344, 348) and a flexible member (346) layered on top of each other in a substantially linear arrangement, buttress assembly (340) is configured to provide the advantages of both anvil-side buttress body (308) and cartridge-side buttress body (304), while associating with just staple deck (74), rather than both staple deck (74) and anvil (56). Rigid members (344, 348) may be formed of the same material, or different material as would be apparent to one skilled in the art in view of the teachings herein. For example, rigid member (344) may be more rigid than rigid member (348) such that upper rigid member (348) may more easily deform in response to jaws (52, 54) grasping tissue ($T_1$, $T_2$) in accordance with the description herein.

Figure 22:
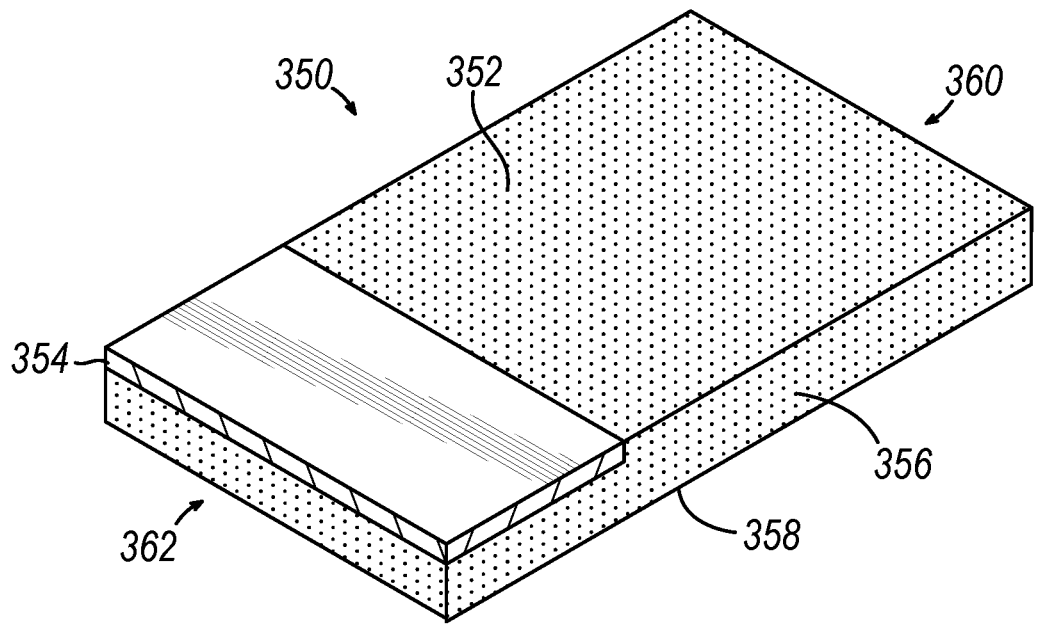
FIG. 22 depicts a perspective view of an alternative buttress assembly.

In some instances, it may not be required to guide every staple (80) into contact with staple forming pockets (58). For example, while jaws (52, 54) grasp tissue ($T_1$, $T_2$) in accordance with the description herein, a proximal portions of jaws (52, 54) may be suitably aligned with each other in the lateral direction while a distal portion of jaws (52, 54) may laterally deviate relative to each other. Therefore, it may be more desirable to guide staples (80) located at a distal end of jaws (52, 54) as compared to a proximal end. FIG. 22 shows an exemplary buttress assembly (350) that may be loaded onto end effector (50) in replacement of buttress assemblies (110, 112, 300, 302, 320, 340) or adjunct (230) described above.

Buttress assembly (350) extends between a proximal end (360) and a distal end (362). Buttress assembly (350) is substantially similar to buttress assembly (340) described above, with differences elaborated below. Buttress assembly (350) includes an adhesive layer (352) that is substantially similar to adhesive layer (342) described above. Buttress assembly (350) also includes a flexible member (356) that is substantially similar to flexible member (346) described above. However, a proximal portion of flexible member (356) is configured to be placed adjacent to staple deck (74). Rather than having two rigid members (344, 348) that extend along the length of buttress assembly (350), buttress assembly (350) only includes a single rigid member (354) placed adjacent to staple deck (74). Further, rigid member (354) is located only at a distal end (362) such that rigid member (354) only guide staples (80) located at a distal end of replaceable staple cartridge (70). Therefore, if distal ends of jaws (52, 54) literally deviate relative to each other in response to end effector (50) grasping tissue ($T_1$, $T_2$), rigid member (354) may help guide distal staples (80) such that staple legs (126) to not further deviate away from the intended staple forming pocket (58) during firing.

It should be understood that buttress assembly (350) may include two distal rigid members (354) that covered adjacent portions of flexible member (356) such that flexible member (356) is interposed between rigid members.

Figure 23:
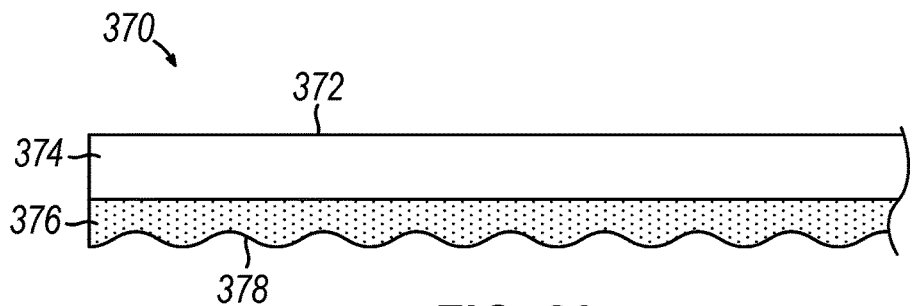
FIG. 23 depicts an elevational side view of an alternative buttress assembly.
Figure 24:
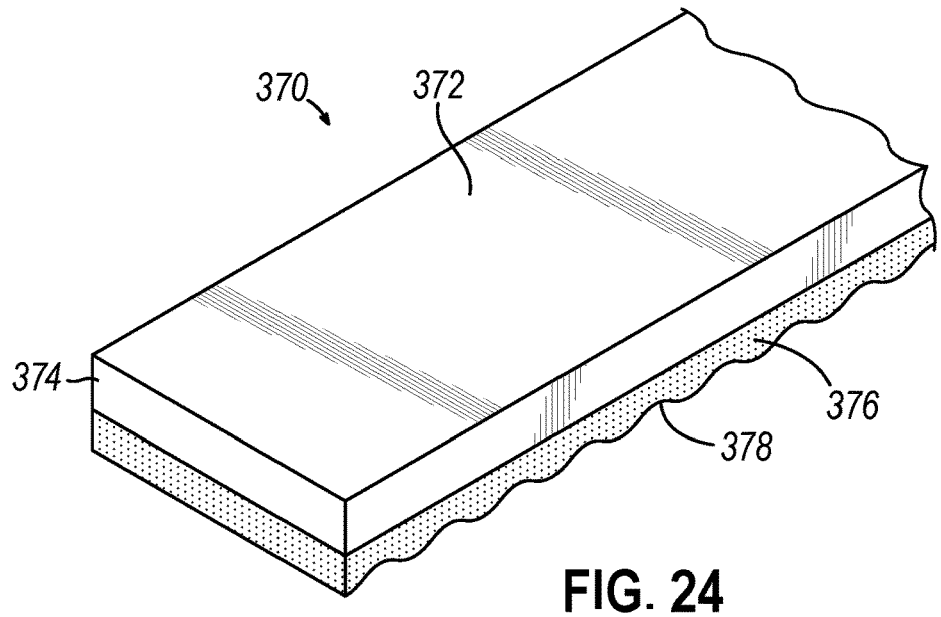
FIG. 24 depicts a perspective view of the buttress assembly of FIG. 23.
Figure 25:
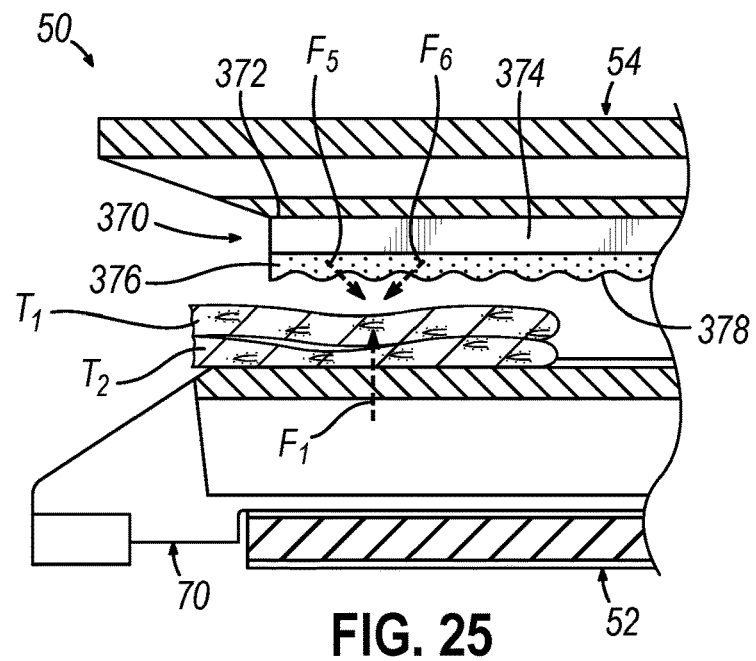
FIG. 25 depicts a cross-sectional side view of a portion of the end effector of FIG. 3 with the buttress assembly of FIG. 23 attached to the anvil of the end effector, showing the end effector jaws in a partially closed state with tissue positioned between the upper and lower jaws.

While buttress assembly (320) described above is designed to inhibit tissue flow in lateral directions of end effector (50), in some instances, it may be desirable to additionally, or alternatively, inhibit tissue flow in the longitudinal directions. FIGS. 23-25 show an alternative buttress assembly (370) that may be loaded onto end effector (50) in replacement of buttress assemblies (110, 112, 300, 302, 320) or adjunct (230) described above. As will be described in greater detail below, buttress assembly (370) is configured to provide the benefits of buttress assembly (110, 112) and/or adjunct (230) described above, while also inhibiting an undesirable amount of tissue flow in the longitudinal directions.

Buttress assembly (370) includes an adhesive layer (372), a top rigid member (374), and a bottom flexible member (376). Adhesive layer (372) is associated with a top portion of rigid member (374). Adhesive layer (372) is provided on rigid member (374) to adhere buttress assembly (370) to anvil (56). Such an adhesive material may provide proper positioning of rigid member (374) and flexible member (376) before and during actuation of end effector (50); then allow rigid member (374) and flexible member (376) to separate from end effector (50) after end effector (50) has been actuated, without causing damage to rigid member (374) and flexible member (376) that is substantial enough to compromise the proper subsequent functioning of buttress assembly (370). In some instances, buttress assembly (370) is attached to anvil (56) via buttress applier cartridge (260). In other instances, buttress assembly (370) may be attached to anvil (56) during manufacturing of end effector (50). It should be understood that in the current example, buttress assembly (370) is attached to anvil (56), this is merely optional, as buttress assembly (370) may be attached to staple deck (74).

Flexible member (376) includes a longitudinally extending, undulating, tissue engagement surface (378) configured to directly engage tissue ($T_1$, $T_2$) is response to jaws (52, 54) grasping tissue ($T_1$, $T_2$) in accordance. Flexible member (376) may be made from the same material as buttress bodies (114, 118) or adjunct (230) described above. Therefore, flexible member (376) is configured to suitably deform in response to jaws (52, 54) grasping tissue ($T_1$, $T_2$) in accordance with the description herein. However, rigid member (374) is suitably stiff such that rigid member (374) retains its intended shape in response to jaws (52, 54) grasping tissue ($T_1$, $T_2$). While rigid member (374) is suitably rigid to retain its intended shape in response to jaws (52, 54) grasping tissue ($T_1$, $T_2$), rigid member (374) is also configured to be penetrated by staples (80) such that legs (126) of staples may suitably engage staple forming pockets (58) to attach tissue ($T_1$, $T_2$) and buttress assembly (370) together in response to suitably firing end effector (50) in accordance with the teachings herein.

As best shown in FIG. 25, concave portions of undulating surface (378) are configured to inhibit an undesirable amount of tissue flow in the longitudinal directions. Flexible member (376) deforms in response to staple deck (74) and tissue engagement surface (378) of flexible member (376) begin to engage tissue grasping tissue ($T_1$, $T_2$). In particular, the upward force (F1) acting on tissue ($T_1$, $T_2$) causes flexible member (376) to suitably deform, which may therefore provide similar benefits compared to buttress assemblies (110, 112) and/or adjunct (230) described above. The geometry of undulating surface (378) imparts downward and longitudinal forces (F5, F6) on tissue ($T_1$, $T_2$). Downward-longitudinal forces (F5, F6) include longitudinal components facing in opposite directions of one another. The opposite longitudinal components of forces (F5, F6) inhibit an undesirable amount of grasped tissue ($T_1$, $T_2$) from moving off of staple deck (74) in longitudinal shown above.

While tissue engagement surface (378) is shown having the undulating surface in the current example, this is merely optional. Rigid member (374) and flexible member (376) may have complementary contours surfaces where rigid member (374) and flexible member (376) engage with each other, similar to buttress assembly (320) described above.

C. Exemplary Adjuncts to Reinforce Staple Line

As mentioned above, in some instances, it may be desirable to provide an end effector with an adjunct or combination of adjuncts capable of severing and stapling tissue to form a suitable and secure seal of tissue without forming a traditional "B" shaped staple. For example, in some instances, utilizing buttress assembly (110, 112) and/or adjunct (230) in accordance with the description herein may be impart sufficient pressure on tissue ($T_1$, $T_2$) such that buttress assembly (110, 112) and/or adjunct (230) substantially seals recently severed tissue ($T_1$, $T_2$). Therefore, in some instances, the compressive forces provided by fired staples may not be required for purposes of primarily sealing severed tissue ($T_1$, $T_2$), but may be needed to ensure tissue ($T_1$, $T_2$) remains stapled and buttress assembly (110, 112) and/or adjunct (230) remains in suitable contact with severed tissue ($T_1$, $T_2$).

Figure 26:
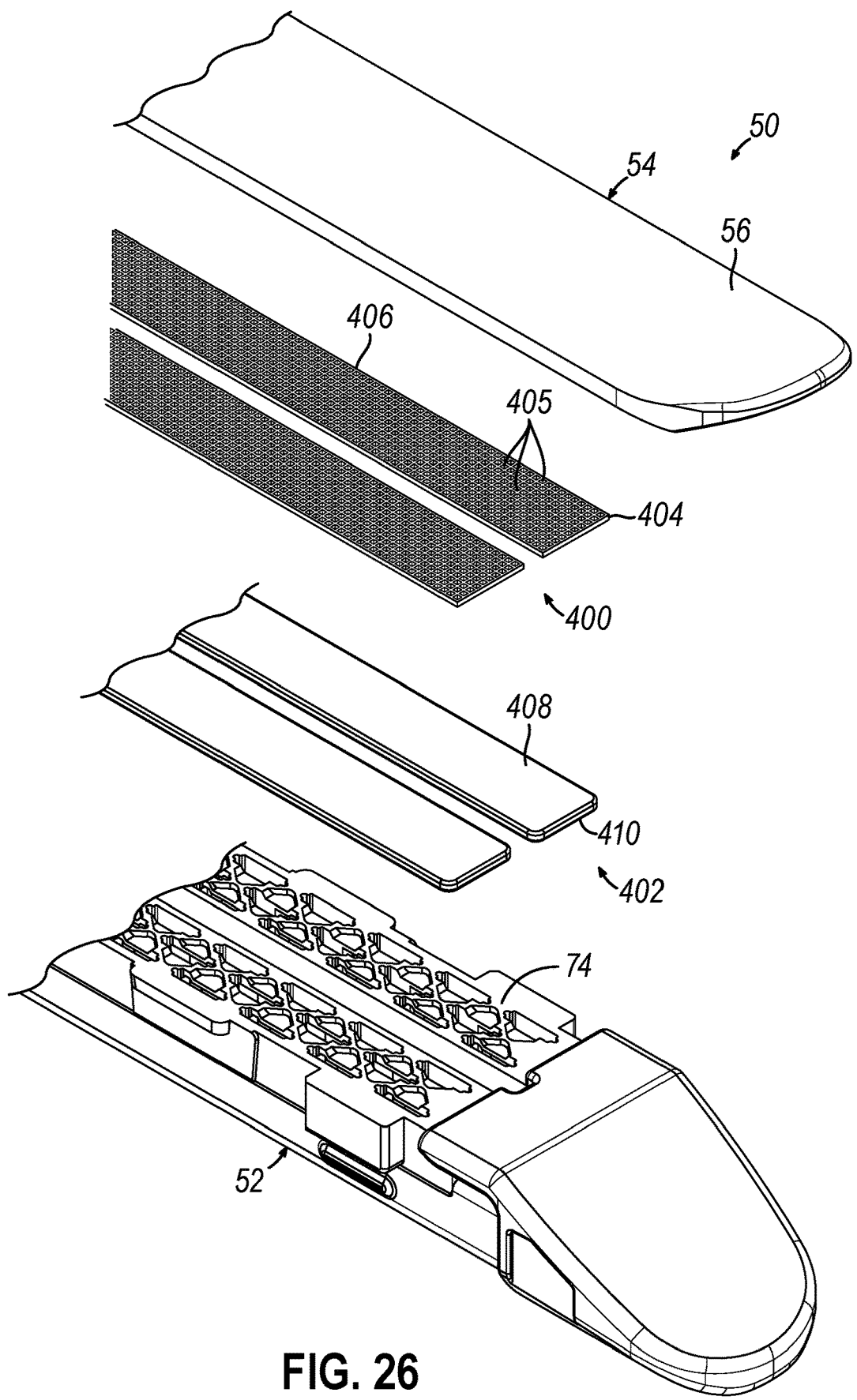
FIG. 26 depicts an exploded perceptive view of the end effector for FIG. 3 and alternative buttress assemblies.
Figure 27:
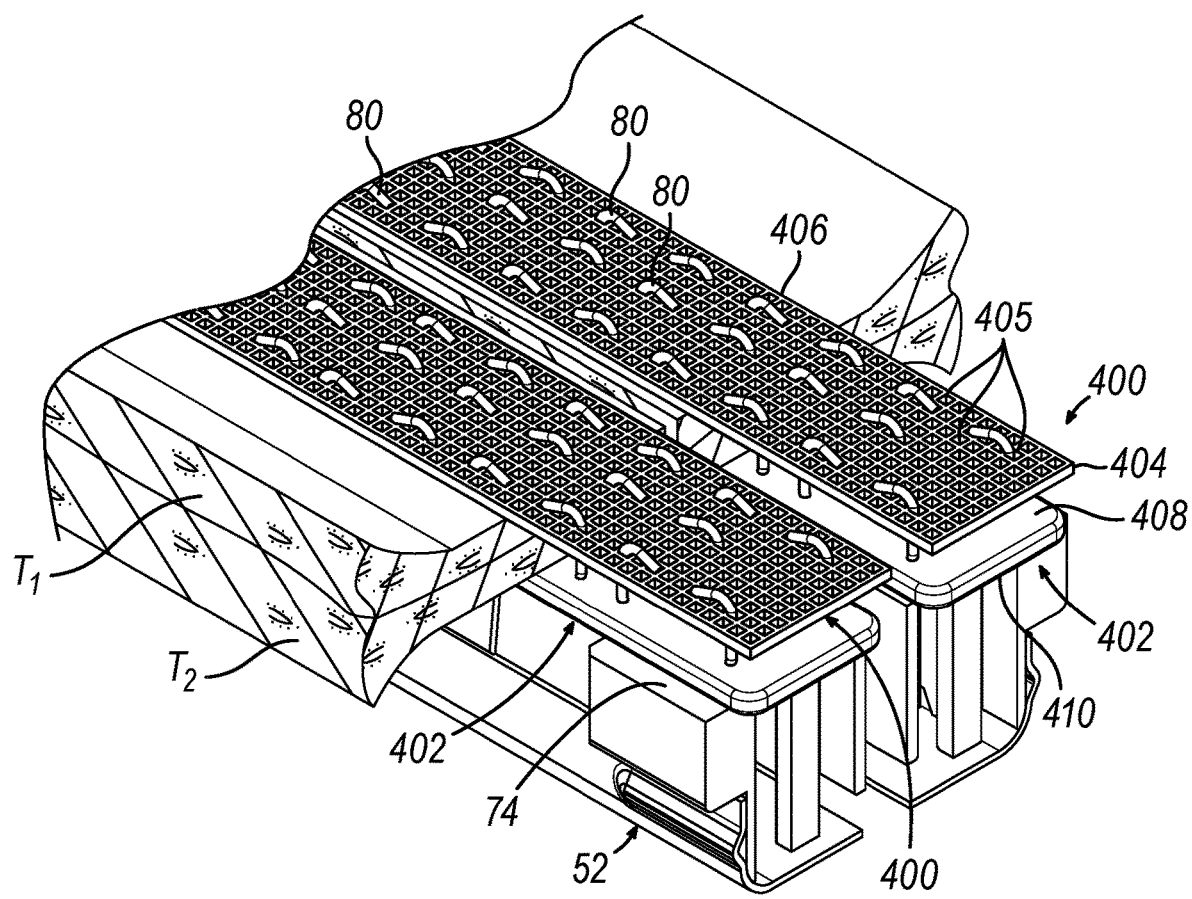
FIG. 27 depicts a perspective view of the end effector of FIG. 3 and the buttress assemblies of FIG. 26; showing fired staples while the end effector jaws are in a closed state on the tissue, with selected components omitted for purposes of clarity.
Figure 28:
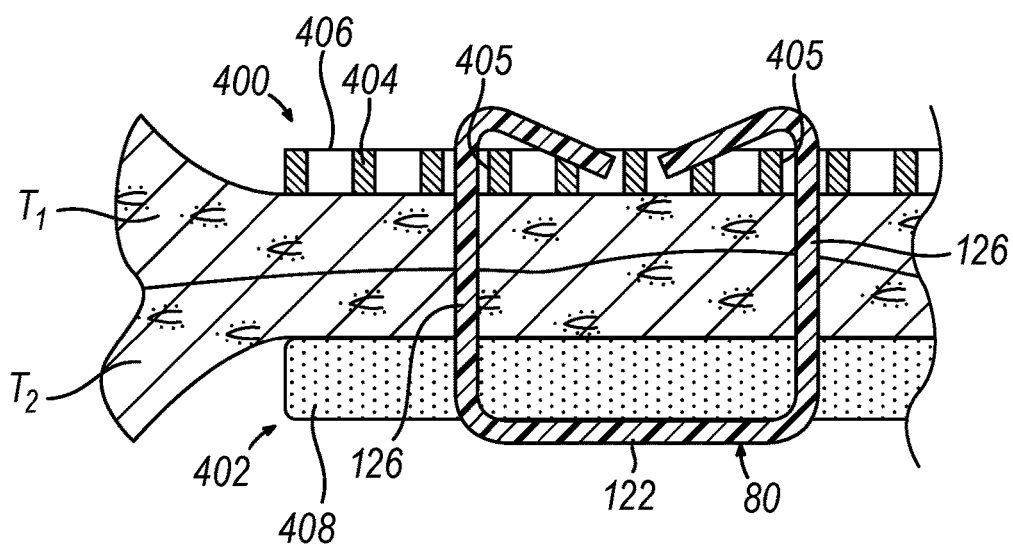
FIG. 28 depicts a cross-sectional view of a formed staple and the buttress assemblies of FIG. 26 after having been secured to the tissue by the end effector of FIG. 3.

FIGS. 26-28 show exemplary anvil-side buttress assembly (400) and an exemplary cartridge-side buttress assembly (402) that may be readily incorporated into end effector (50). Anvil-side buttress assembly (400) includes a mesh buttress body (404) that may receive legs (126) of recently fired staples (80) in order to enforce recently formed staple lines, even when recently fired staples (80) fail to form a traditional "B" shaped staple. As will be described in greater detail below, mesh buttress body (404) is configured to inhibit bent staples legs (126) from re-straightening, which could possibly allow fired staples (80) to disassociate with buttress assemblies (400, 402) and recently severed tissue ($T_1$, $T_2$).

Cartridge-side buttress assembly (402) is initially attached to staple deck (74). Cartridge-side buttress assembly (402) may be substantially similar to buttress assembly (110, 112) and/or adjunct described above. Therefore, cartridge-side buttress assembly (402) includes a buttress body (408) and an adhesive layer (410). Cartridge-side buttress assembly (402) may be configured to provide structural reinforcement to the lines of staples (80) formed in tissue ($T_1$, $T_2$). Additionally, or alternatively, cartridge-side buttress assembly (402) may be configured to apply a compression spring force to stapled tissue consistently along the entire length of the formed staple pattern, thereby ensuring a secure seal of tissue having a thickness that varies along a length of the formed staple pattern and end effector (50). It should be understood that cartridge-side buttress assembly (402) may be configured to provide any other suitable benefit as would be apparent to one skilled in the art in view of the teachings herein.

Anvil-side buttress assembly (400) includes mesh buttress body (404) and an adhesive layer (406). Adhesive layer (406) is provided on buttress body (404) to adhere buttress body (404) to anvil (56). Such an adhesive material may provide proper positioning of buttress body (404) before and during actuation of end effector (50); then allow buttress body (404) to separate from end effector (50) after end effector (50) has been actuated, without causing damage to buttress body (404) that is substantial enough to compromise the proper subsequent functioning of buttress body (404). In some instances, anvil-side buttress assembly (400) is attached to anvil (56) via buttress applier cartridge (260). In other instances, anvil-side buttress assembly (400) may be attached to anvil (56) during manufacturing of end effector (50).

Mesh buttress body (404) is configured to receive fired staples (80) such that mesh buttress body (404) attaches to tissue ($T_1$, $T_2$) in similar fashion as buttress body (114, 118) described above. However, mesh buttress body (404) defines a grid-like array of openings (405). As best shown in FIGS. 27-28, openings (405) are dimensioned to receive staples legs (126) of staples (80). In particular, one opening (405) may receive a straight portion of leg (126), while a separate opening (405) may receive the terminating end of the same staple leg (126). Portions of mesh buttress body (404) defining openings (405) that receive the same staple leg (126) may cooperatively reinforce the bent section of a recently fired staples (80), thereby inhibiting the bent portion of the staple leg (126) from bending back toward a pre-fired position. Therefore, if a recently fired staple (80) fails to form a traditional "B" shape, as shown in FIGS. 27-28, mesh buttress body (404) may reinforce the newly formed staple line.

Mesh buttress body (404) may be formed of any suitable material as would be apparent to one skilled in the art in view of the teachings herein. Additionally, while in the current example, openings (405) defining by mesh buttress body (404) are substantially square-shaped, openings (405) may have any suitable geometry as would be apparent to one skilled in the art in view of the teachings herein. For example, openings (405) may be rectangular, circular, oval, triangular, etc. Additionally, while openings (405) are substantially uniform in size and geometry in the current example, this is merely optional. For instance, openings (405) may become smaller at a distal end of buttress body (404) compared to a proximal end of buttress body (404), or vice versa.

Figure 29:
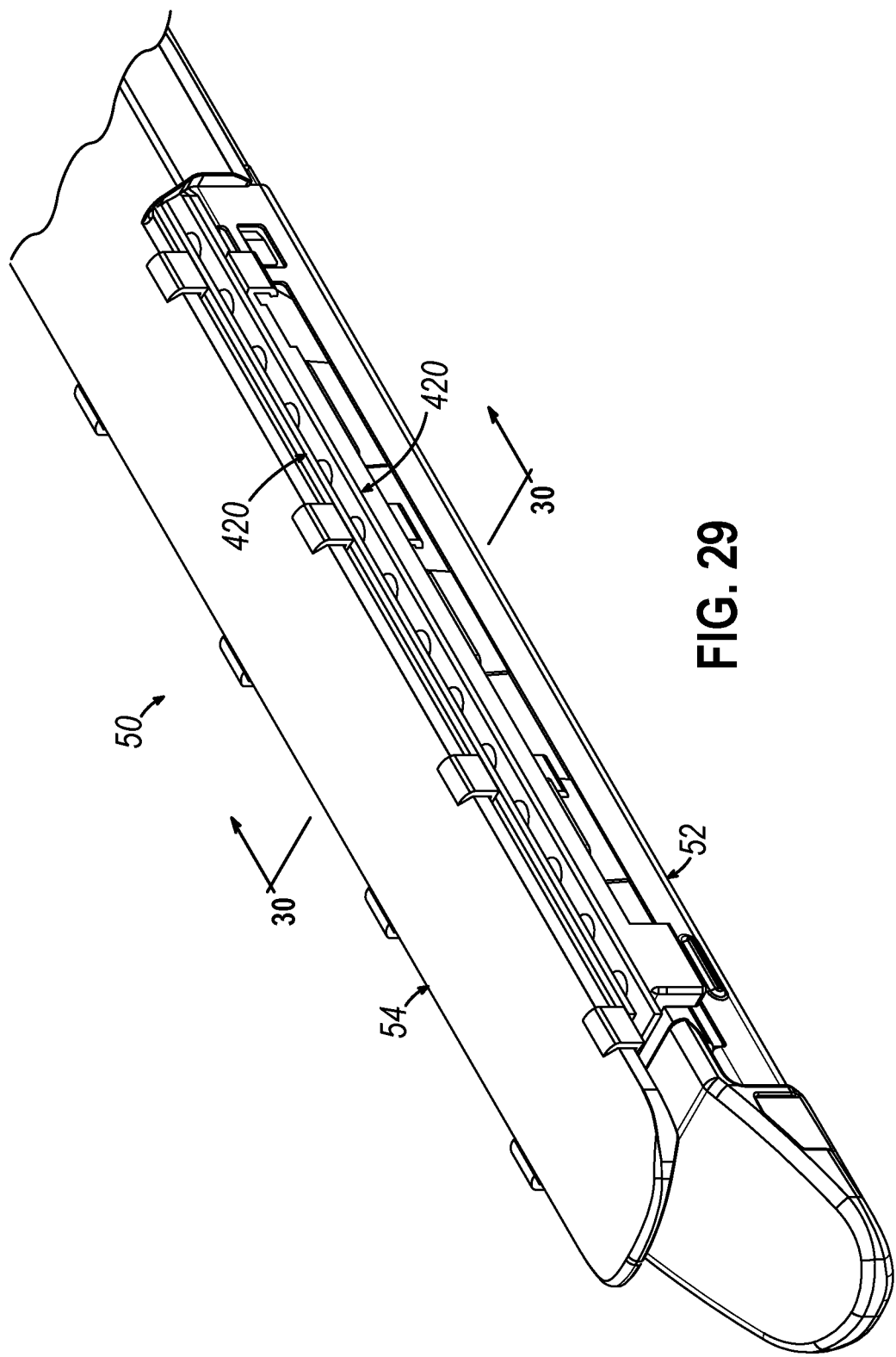
FIG. 29 depicts a perspective view of the end effector of FIG. 3 with a pair of alternative buttress assemblies applied to the upper and lower jaws of the end effector.
Figure 30:
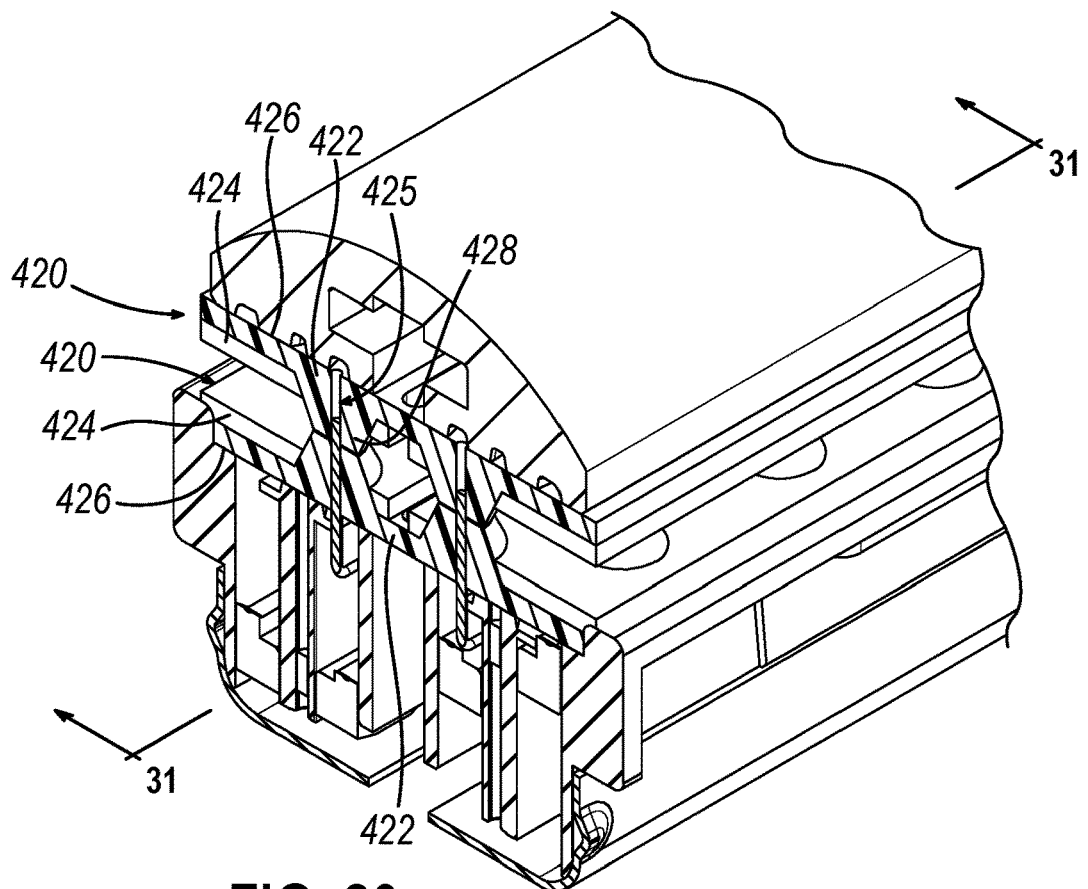
FIG. 30 depicts a sectional perspective view of the end effector of FIG. 3 and the buttress assemblies of FIG. 29, taken along line 30-30 of FIG. 29.
Figure 31:
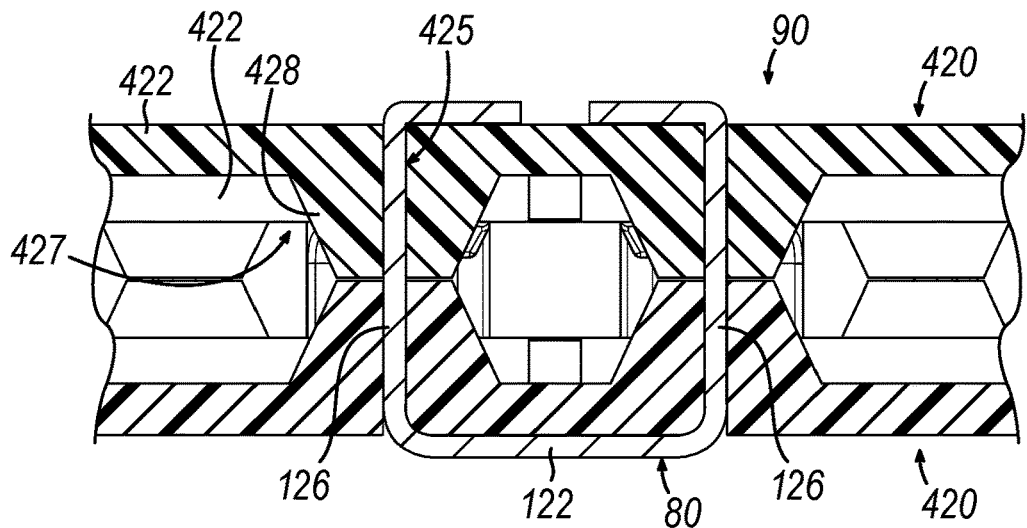
FIG. 31 depicts a cross-sectional view of the end effector of FIG. 3 and the buttress assemblies of FIG. 29, taken along line 31-31 of FIG. 30.

FIGS. 29-31 show an exemplary pair of buttress assemblies (420) that may be readily incorporated into end effector (50). One buttress assembly (420) may associate with staple deck (74), while the buttress assembly (420) associates with anvil (56). Each buttress assembly (420) includes a bioabsorbable structural component (422) and a bioabsorbable compressible component (424). As will be described in greater detail below, structural component (422) defines a plurality of pathways (425) dimensioned to align with a respective pathway (425) of the opposing assembly (420) while end effector (50) is in the closed position; while pathways (425) are dimensioned to receive a leg (126) of a fired staple (80). Additionally, bent portions of leg (126) may engage outer surface of a first structural components (422) associated with anvil (56), while crown (122) may engage the outer surface of the second structural component (422) associated with staple deck (74) to keep buttress assemblies (420) and tissue ($T_1$, $T_2$) suitably attached.

Buttress assembly (420) may attach to respective staple deck (74) or anvil (56) via an adhesive layer that may be substantially similar to adhesive layers (116, 120) described above. Therefore, buttress assembly (420) is configured to selectively detach from end effector (50) after firing of end effector (50) in accordance with the description herein.

Structural component (422) comprises a plurality of protrusions (428), each defining pin pathway (425). Protrusion (428) associated with anvil (56) are configured to face toward protrusions (428) associated with staple deck (74) such that opposing protrusions (428) may face toward each other while end effector (50) is in the closed configuration, similar to that shown in FIG. 31. Protrusions (428) extend through a respective opening (427) defining by compressible component (424) such that structural component (422) and compressible component (424) are attached to each other. Structural component (422) and compressible component (424) may be attached to each other via any suitable means as would be apparent to one skilled in the art in view of the teachings herein.

Compressible component (424) may be substantially similar to buttress body (114, 118) and/or adjunct (230). Therefore, compressible component (424) may be configured to provide structural reinforcement to the lines of staples (80) formed in tissue ($T_1$, $T_2$). Additionally, or alternatively, compressible component (424) may be configured to apply a compression spring force to stapled tissue consistently along the entire length of the formed staple pattern, thereby ensuring a secure seal of tissue having a thickness that varies along a length of the formed staple pattern and end effector (50). It should be understood that compressible component (424) may be configured to provide any other suitable benefit as would be apparent to one skilled in the art in view of the teachings herein.

As mentioned above, structural component (422) defines a plurality of pathways (425) that are configured to align with a respective pathway (425) of the opposing structural component (422). When end effector (50) is suitably closed, staples (80) may be fired such that legs (126) travel through pathways (425) (or a portion of protrusion (428) adjacent to pathway (425)) and contact anvil (56) to form bent legs (126). However, as shown in FIG. 31, staples (80) are not configured to form a traditional "B" shaped staple, but legs (126) bend to form a right angle with crown (122).

As best shown in FIG. 31, an outer surface of structural component (422) is configured to engage a fired staple (80) such that bent legs (126) have a suitable surface to engage after firing. In some instances, bent legs (126) may penetrate outer surface of structural components (422). Structural component (422) is sufficiently rigid such that engagement between legs (126)/crown (122) and the outer surfaces of structural component (422) allows the assembly shown in FIG. 31 to provide compression equivalent to a conventional staple line with "B" formed staples until tissue is fully healed. Structural component (422) may therefore inhibit bends in staple (80) from unbending and disassociating with buttress assemblies (420). Since all components of buttress assembly (420) are biodegradable, buttress assembly (420) is eventually absorbed after tissue if fully healed. While staple (80) with two legs (126) is shown in FIG. 31, buttress assemblies (420) may be configured to work in conjunction with a pin like staple having only one leg, such that crown (122) and leg (126) form a "C" shape when fired.

Structural component (422) may be injection molded from a bioabsorbable material, such as a copolymer made from 90% glycolide and 10% L-lactide. Of course, structural component (422) may be formed of any suitable material as would be apparent to one skilled in the art in view of the teachings herein.

FIGS. 32-35 show an exemplary staple clip (430) configured to form a "C" shape after being suitable fired. Staple clip (430) may be readily incorporated with buttress assemblies (420) described above. Alternatively, as shown in FIGS. 36A-36E, staple clip (430) may be used in conjunction with an anvil-side buttress assembly (440) and a cartridge-side buttress assembly (442). As will be described in further detail below, staple clip (430) and buttress assemblies (440, 442) are configured to suitably attach to and seal tissue ($T_1$, $T_2$) recently severed by end effector (50) without forming a traditional "B" shaped staple.

Staple clip (430) is housed within staple openings (78) of cartridge assembly (70) in replacement of staples (80) described above. Therefore, staple clips (430) are configured to be fired against staple forming pockets (58) of anvil (56) in response to firing of end effector (50) in accordance with the description herein. Staple clip (430) includes a staple leg (436), a crown (438) connected to staple leg (436) at a juncture (434), and an integrated offset ramp (432). Integrated offset ramp (432) is laterally offset from staple leg (436) and crown (438). In some instances, integrated offset ramp (432) may abut against staple driver (82) in the pre-fired position such that engagement between staple driver (82) and offset ramp (432) drives staple clip (430) out of staple openings (78) when end effector (50) is fired; and/or such that engagement between staple driver (82) and offset ramp (432) stabilizes clip (430) while end effector (50) is fired. In some instances, direct contact between integrated offset ramp (432) and wedge sled (86) may drive staple clips (430) out of staple openings (78) when end effector (50) is fired such that use of staple drivers (82) is optional. In some instances, offset tamp (432) is entirely omitted such that engagement between crown (438) and staple driver (82) drives staple clip (430) out of staple openings (78) when end effector (50) is fired.

Figure 32:
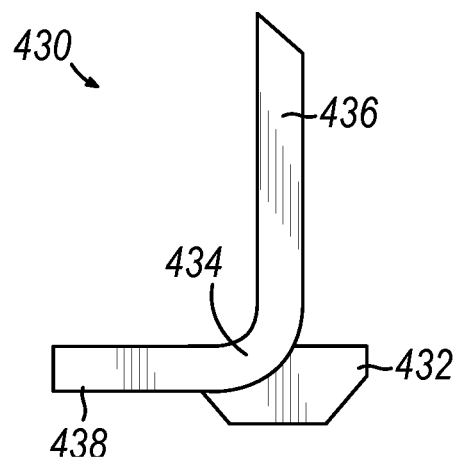
FIG. 32 depicts an elevational side view of an exemplary staple clip in a pre-fired configuration.
Figure 33:
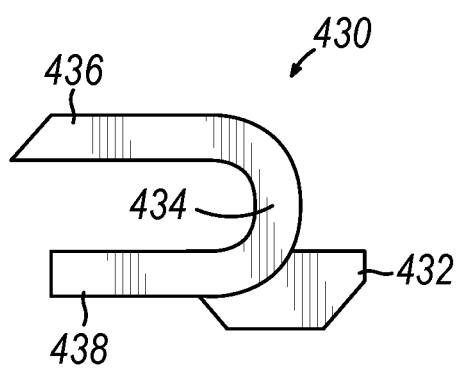
FIG. 33 depicts an elevational side view of the staple clip of FIG. 32 in a post-fired configuration.
Figure 34:
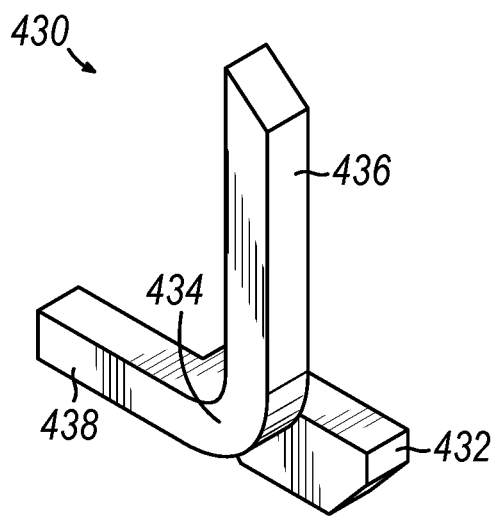
FIG. 34 depicts a perspective view of the staple clip of FIG. 32 in the pre-fired configuration.
Figure 35:
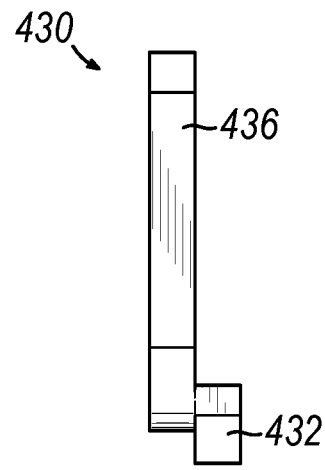
FIG. 35 depicts an elevational front view of the staple clip of FIG. 32 in the pre-fired configuration.

As shown between FIGS. 32-33, leg (436) of clip (430) is configured to bend relative to crown (438) from the pre-fired position into the fired position such that leg (436) and clip transition between an "L" shape and a "C" shape. As will be described in greater detail below, leg (436) is configured to penetrate tissue ($T_1$, $T_2$) and buttress assemblies (440, 442) while clips (430) are fired by end effector (50). Additionally, contact with staple forming pocket (58) may be configured to drive leg (436) from the pre-fired "L" shape into the post-fired "C" shape in order to suitably couple buttress assemblies (440, 442) with recently severed tissue ($T_1$, $T_2$), thereby suitably coupling and sealing severed tissue ($T_1$, $T_2$). As will also be described in great detail below, an extended feature (452) configured to travel with either wedge sled (86) and/or elongate firing member (60) may be configured to further drive leg (436) into the post-fired "C" shape.

Anvil-side buttress assembly (440) and cartridge-side buttress assembly (442) may be substantially similar to anvil-side buttress assembly (400) and cartridge-side buttress assembly (402) described above, with differences elaborated below. Therefore, anvil-side buttress assembly (440) includes a mesh buttress body (444) and an adhesive layer (446) that are substantially similar to mesh buttress body (404) and adhesive layer (406) described above, respectively; while cartridge-side buttress assembly (442) includes a buttress body (448) and an adhesive layer (450) that are substantially similar to buttress body (408) and adhesive layer (410) described above, respectively.

Figure 36A:
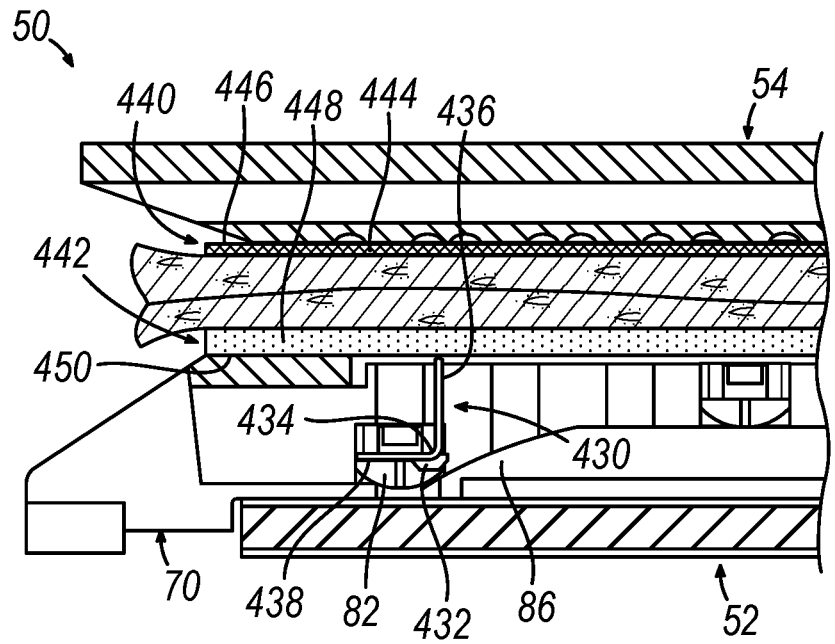
FIG. 36A depicts a cross-sectional side view of the end effector of FIG. 3 with a pair of alternative buttress assemblies applied to the upper and lower jaws of the end effector and the staple clip of FIG. 29 loaded into the replaceable cartridge assembly of the end effector, showing the end effector jaws in the closed state with tissue captured between the upper and lower jaws.
Figure 36B:
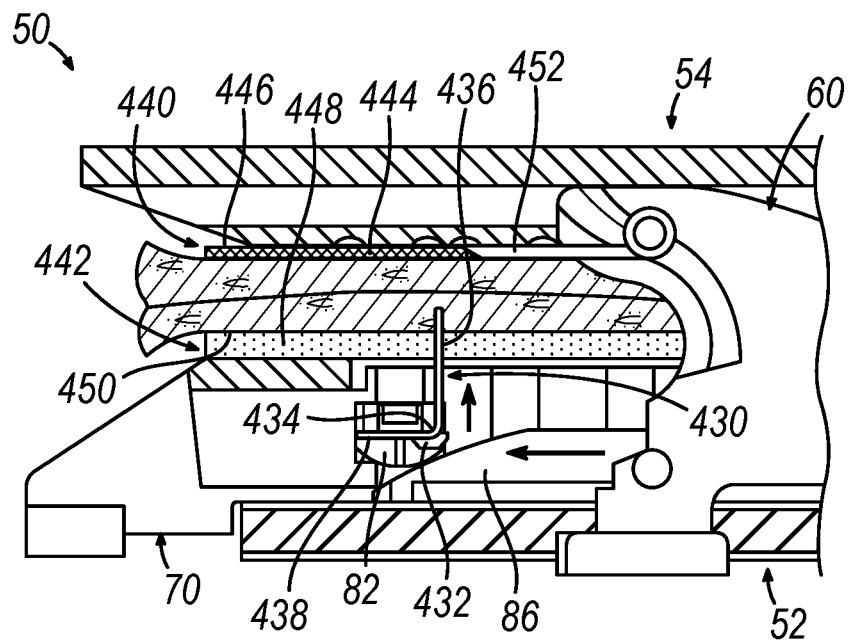
FIG. 36B depicts a cross-sectional side view of the end effector of FIG. 3 with the pair of alternative buttress assemblies of FIG. 36A applied to the upper and lower jaws of the end effector and the staple clip of FIG. 29 loaded into the replaceable cartridge assembly of the end effector, showing the staple clip partially fired into the captured tissue.

FIGS. 36A-36E show an exemplary firing of end effector (50) incorporating staple clips (430). First, as shown in FIG. 36A, jaws (52, 54) and buttress assemblies (440, 442) may suitably grasp tissue ($T_1$, $T_2$). Once tissue ($T_1$, $T_2$) is grasped and ready to be severed and stapled, end effector (50) may be fired in accordance with the description herein. As shown between FIGS. 36A-36B, elongate firing member (60) may actuate wedge sled (86) distally such that wedge sled (86) drives staple drivers (82) and corresponding staple clips (430) upward. While engagement between wedge sled (86) and staple drivers (82) actuates staple clips (430) upward in the current example, any of the other means discussed herein may be utilized to fire staple clips (430) upward as would be apparent to one skilled in the art in view of the teaching herein. As also shown in FIG. 36B, actuation of staple clips (430) upwards drives staple legs (436) to penetrate cartridges side buttress assembly (442) and tissue ($T_1$, $T_2$).

Figure 36C:
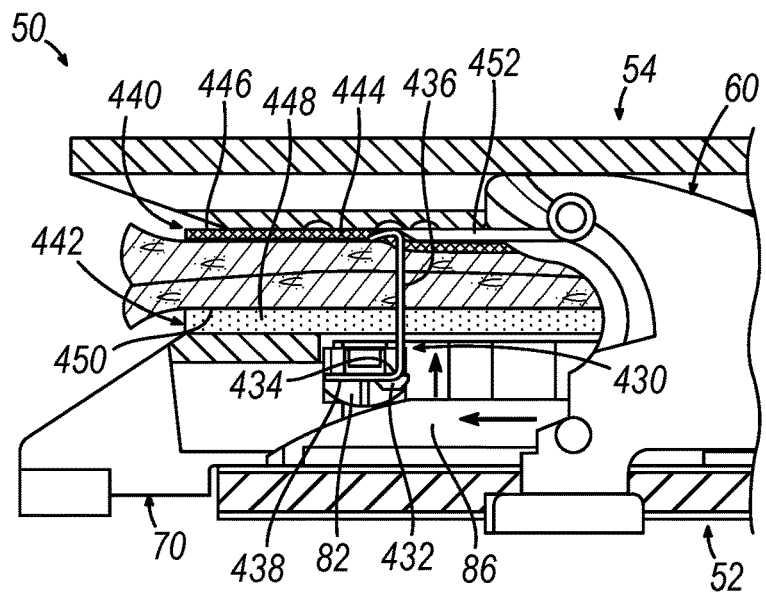
FIG. 36C depicts a cross-sectional side view of the end effector of FIG. 3 with the pair of alternative buttress assemblies of FIG. 36A applied to the upper and lower jaws of the end effector and the staple clip of FIG. 29, showing the staple clip partially fired into the captured tissue and against the anvil of the upper jaw.
Figure 36D:
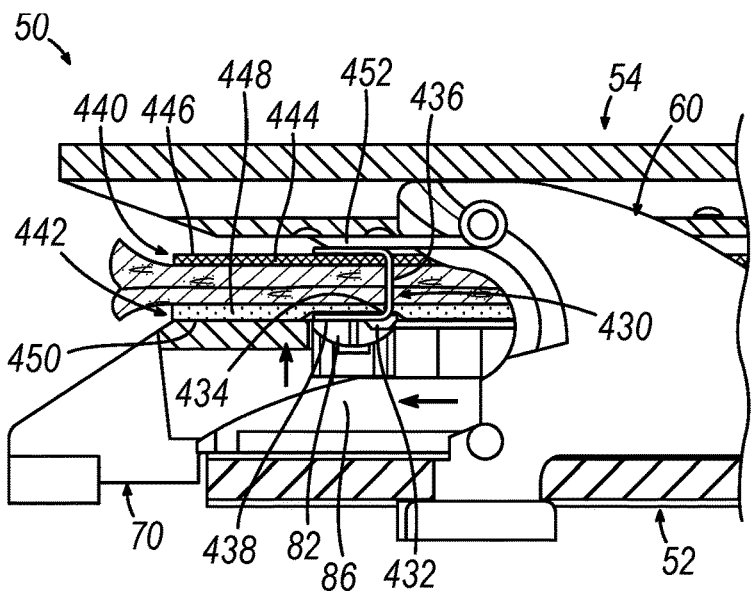
FIG. 36D depicts a cross-sectional side view of the end effector of FIG. 3 with the pair of alternative buttress assemblies of FIG. 36A applied to the upper and lower jaws of the end effector and the staple clip of FIG. 29, showing the staple clip fired thereby capturing the buttress assemblies and the tissue together.
Figure 36E:
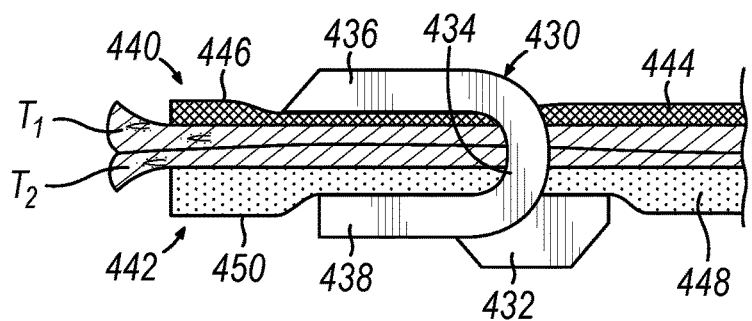
FIG. 36E depicts a cross-sectional side view of a formed staple and the buttress assemblies of FIG. 36A after having been secured to the tissue by the end effector of FIG. 3.

As shown in FIG. 36C, further actuation of staple clips (430) drives staple legs (436) to drive through anvil-side buttress assembly (440) and engage staple forming pocket (58) to initially bend leg (436) toward the "C" shape configuration. Next, as shown between FIGS. 36C and 36D, extended feature (452), which may be associated with any suitable component actuating to fire end effector (50), rides along the surface of anvil (56), further driving legs (436) of staple clips (430) into the "C" shape configuration, thereby attaching recently severed tissue ($T_1$, $T_2$) with buttress assemblies (440, 442). With end effector (50) fired, jaws (52, 54) may release tissue ($T_1$, $T_2$), leaving staple clips (430) and buttress assemblies (440, 442) suitably coupling and sealing recently severed tissue ($T_1$, $T_2$) as shown in FIG. 36E.

After end effector (50) is fired, anvil-side buttress assembly (440) helps distribute pressure from legs (436) to tissue ($T_1$, $T_2$) in such a manner that inhibits legs (436) from tearing through adjacent tissue buttress assembly (440) and also helps distribute pressure from legs (436) to tissue ($T_1$, $T_2$). Therefore, anvil-side buttress assembly (440) allows leg (436) of clips (430) to initially puncture/extend through mesh buttress body (404), but prevents bent legs (436) from pulling through recently severed tissue ($T_1$, $T_2$) after end effector (50) is fired and removed as shown in FIG. 36E. In some instances, buttress body (444) of anvil-side buttress assembly (440) is not a mesh structure, but a thinner and/or more rigid buttress-like layer as compared to cartridge-side buttress body (448).

Cartridge-side buttress assembly (442) may be configured to provide structural reinforcement to the lines of staple clips (430) formed in tissue ($T_1$, $T_2$). Additionally, or alternatively, cartridge-side buttress assembly (442) may be configured to apply a compression spring force to stapled tissue consistently along the entire length of the formed staple pattern, thereby ensuring a secure seal of tissue having a thickness that varies along a length of the formed staple pattern and end effector (50). It should be understood that cartridge-side buttress assembly (442) may be configured to provide any other suitable benefit as would be apparent to one skilled in the art in view of the teachings herein.

D. Exemplary Adjunct Deployment Mechanisms

Figure 37:
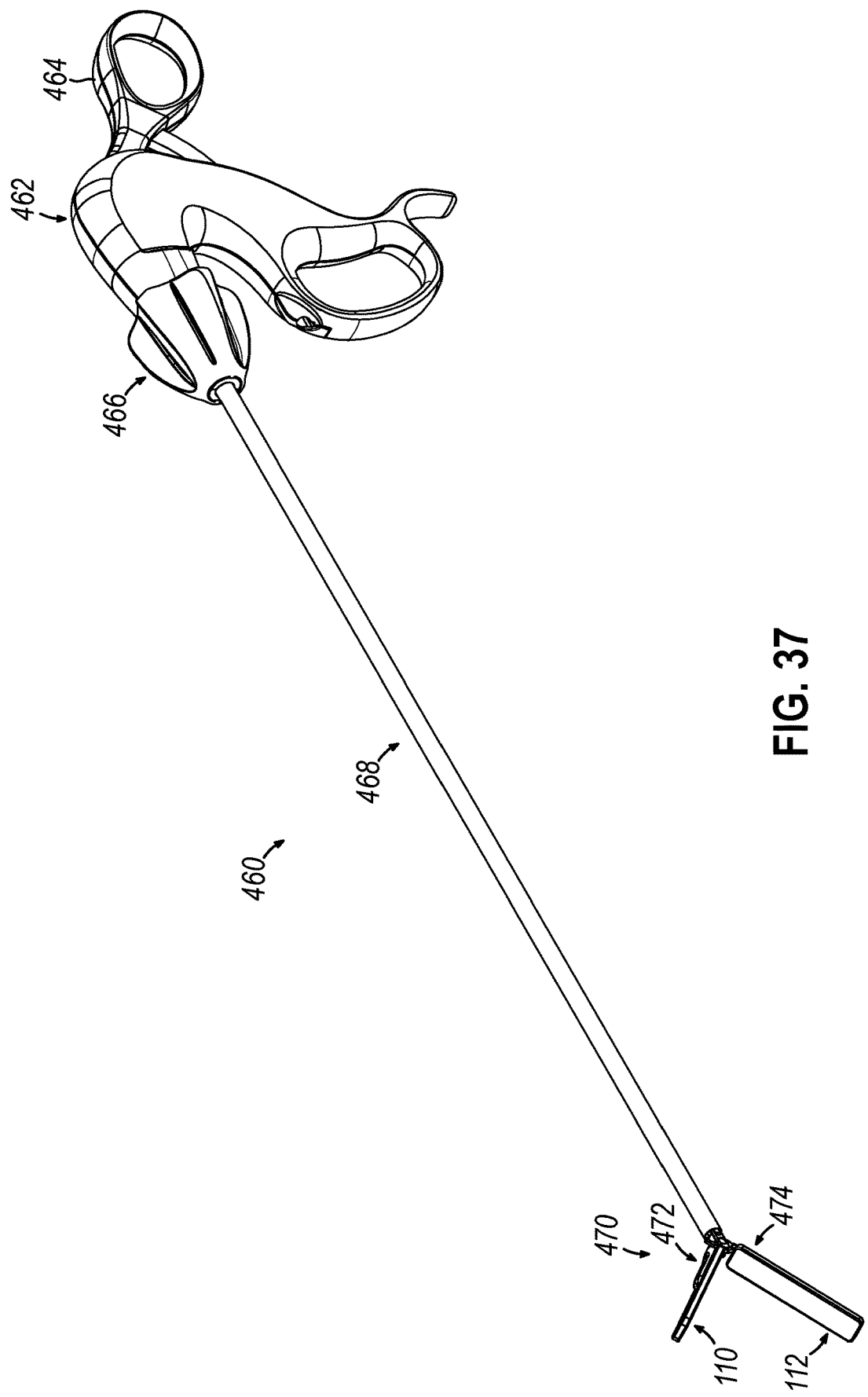
FIG. 37 depicts a perspective view of an exemplary surgical buttress applicator.

As mentioned above, in some instances, it may be desirable to attach an adjunct to an area of tissue targeted for stapling and severing prior to grasping tissue with end effector (50). FIG. 37 shows an exemplary surgical buttress applicator (460) in the form of a surgical grasping instrument configured to be used endoscopically in order to apply buttress assemblies (110, 112) to tissue ($T_1$, $T_2$) prior to introducing end effector (50) for grasping, stapling, and severing tissue ($T_1$, $T_2$) in accordance with the description herein.

Surgical buttress applicator (460) includes a handle assembly (462), a jaw closure trigger (464), a rotation knob (466), a shaft assembly (468) and an end effector (470). Shaft assembly (468) and end effect (470) are dimensioned to be used endoscopically. Rotation knob (466) is configured to rotate shaft assembly (468) and end effector (470) relative to handle assembly (462) about the long axis of shaft assembly (468), thereby allowing a user to selectively orient end effector (470) relative to tissue ($T_1$, $T_2$) in order to suitably grasp tissue ($T_1$, $T_2$). While not shown, surgical buttress applicator (460) may include an articulation assembly configured to deflect end effector (470) relative to the long axis of shaft assembly (468) into various angular positions, thereby providing a greater degree of control during exemplary use in accordance with the description herein.

End effector (470) includes a pair of jaws (472, 474) configured to pivot relative to each other between an open position and a closed position in response to closure trigger (464) actuating relative to handle assembly (462). Jaws (472, 474) are configured to selectively couple with buttress assemblies (110, 112) such that buttress assembly (110, 112) may pivot with jaws (472, 474) between the open and closed positions. Buttress assemblies (110, 112) may be attached to jaws (472, 474) such that end effector (470) may control the placement of buttress assemblies (110, 112) in order to deploy buttress assemblies (110, 112) on tissue ($T_1$, $T_2$) in accordance with the description herein.

Figure 38A:
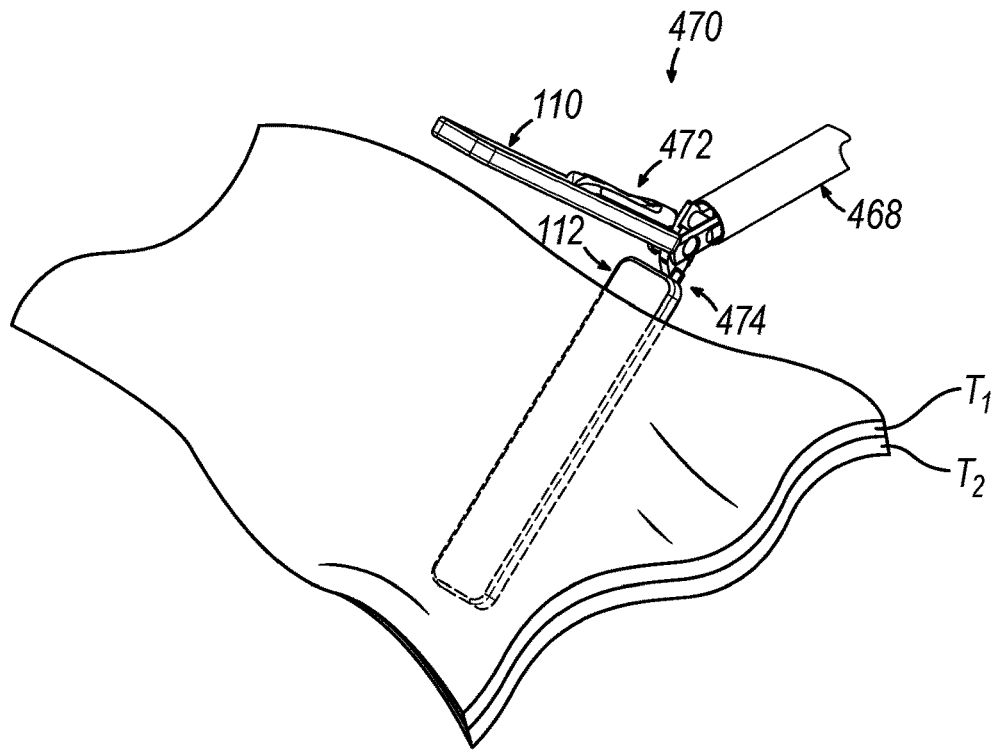
FIG. 38A depicts a perspective view of the end effector of the surgical buttress applicator of FIG. 37 in an open state with tissue positioned between the upper and lower jaws of the surgical buttress applicator.
Figure 38B:
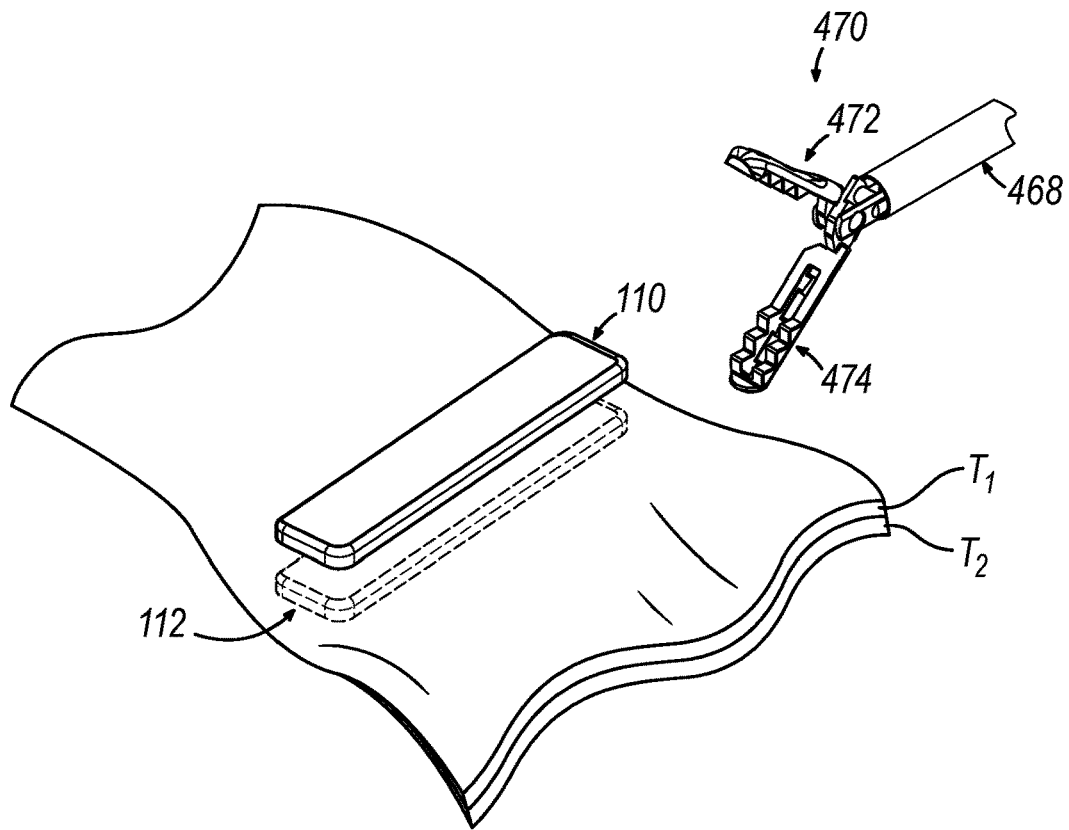
FIG. 38B depicts a perspective view of the end effector of the surgical buttress applicator of FIG. 37 being withdrawn from the surgical site after applying the buttress assemblies of FIG. 7 to recently grasped tissue.
Figure 38C:
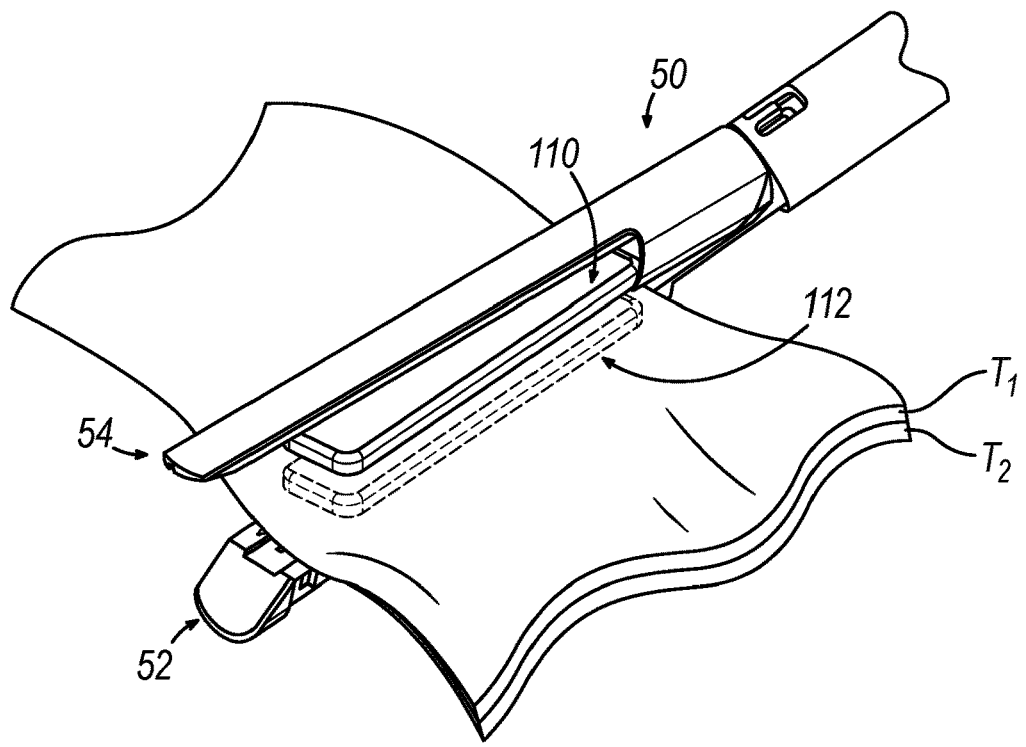
FIG. 38C depicts a perspective view of the end effector of FIG. 3 being introduced to the surgical site and grasping tissue at the surgical site via the recently applied buttress assemblies of FIG. 7.
Figure 38D:
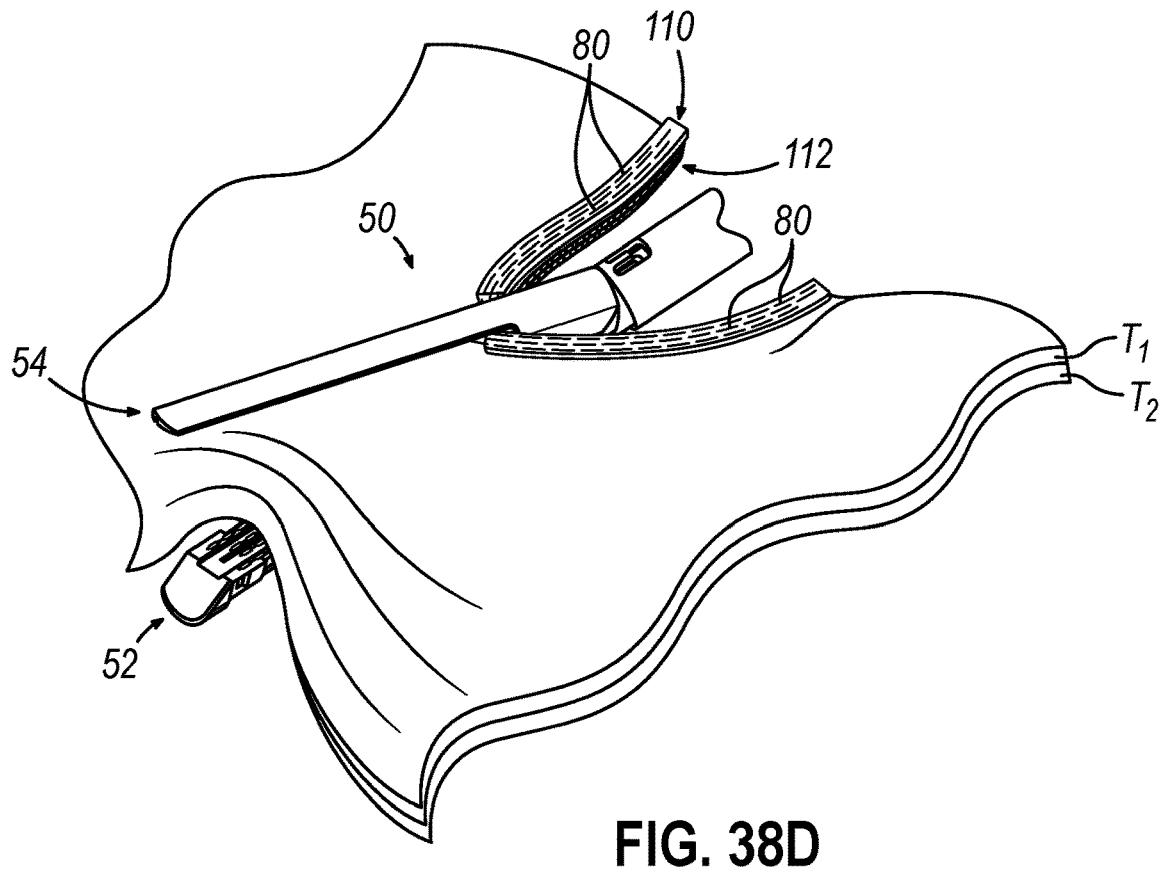
FIG. 38D depicts a perspective view of the end effector of FIG. 3, positioned at tissue and having been fired once in the tissue.

Therefore, as shown in FIG. 38A, a surgeon may utilize applicator (460) to place jaws (472, 474) and buttress assemblies (110, 112) adjacent to a targeted tissue ($T_1$, $T_2$), With jaws (472, 474) in the open position, a surgeon may move end effector (470) such that tissue ($T_1$, $T_2$) is between open jaws (472, 474). Next, a user may utilize jaw closure trigger (464) in order to close jaws (472, 474) such that buttress assemblies (110, 112) engage tissue ($T_1$, $T_2$). The moisture of tissue may provide a sufficient attraction between buttress assemblies (110, 112) and tissue ($T_1$, $T_2$) such that buttress assemblies (110, 112) disassociate with jaws (472, 474) and remain engaged with tissue (($T_1$, $T_2$), as shown in FIG. 38B. Next, a user may remove applicator (460) from the surgical site and introduce end effector (50) to grasp buttress assembly (110, 112), as shown in FIG. 38C. The surgeon may then proceed to fire end effector (50), thereby stapling and severing tissue ($T_1$, $T_2$) and buttress assemblies (110, 112) as shown in FIG. 38D. The surgeon may remove end effector (50) and repeat the steps described above until the desired staple line is formed. In some instances, end effect (470) may be configured to only deploy a single buttress assembly (110, 112), rather than both buttress assemblies (110, 112).

Figure 39:
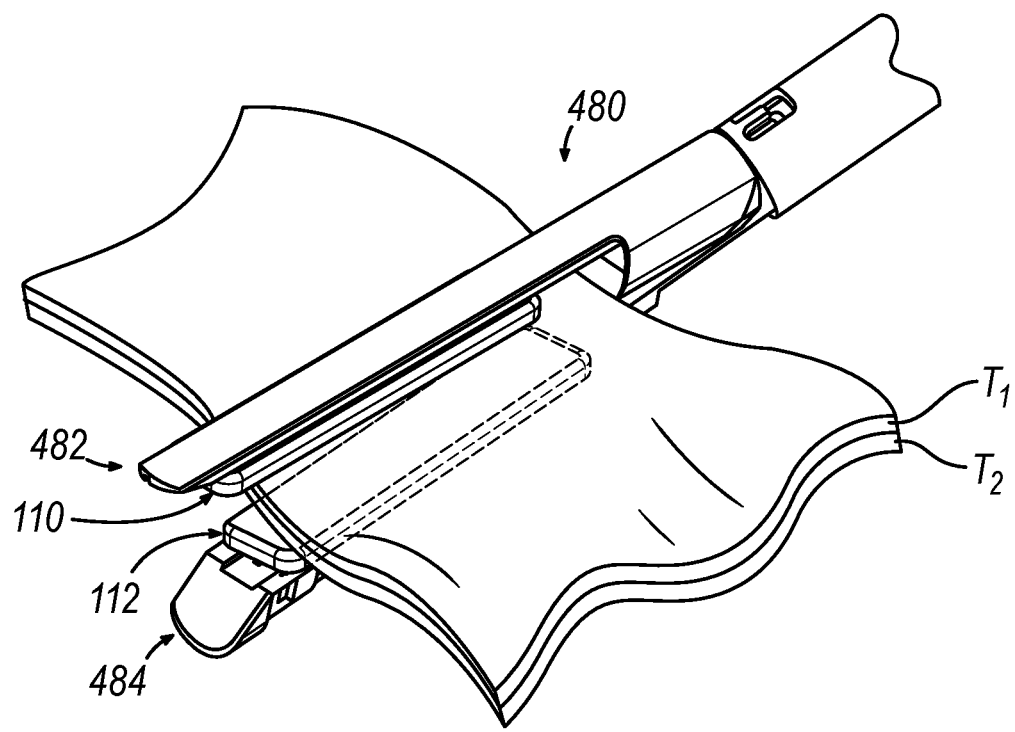
FIG. 39 depicts a perspective view of an alternative exemplary end effector that may be readily incorporated into the surgical buttress applicator of FIG. 37; where the end effector is grasping tissue in preparation of applying the buttress assemblies of FIG. 7 to the grasped tissue.
Figure 40:
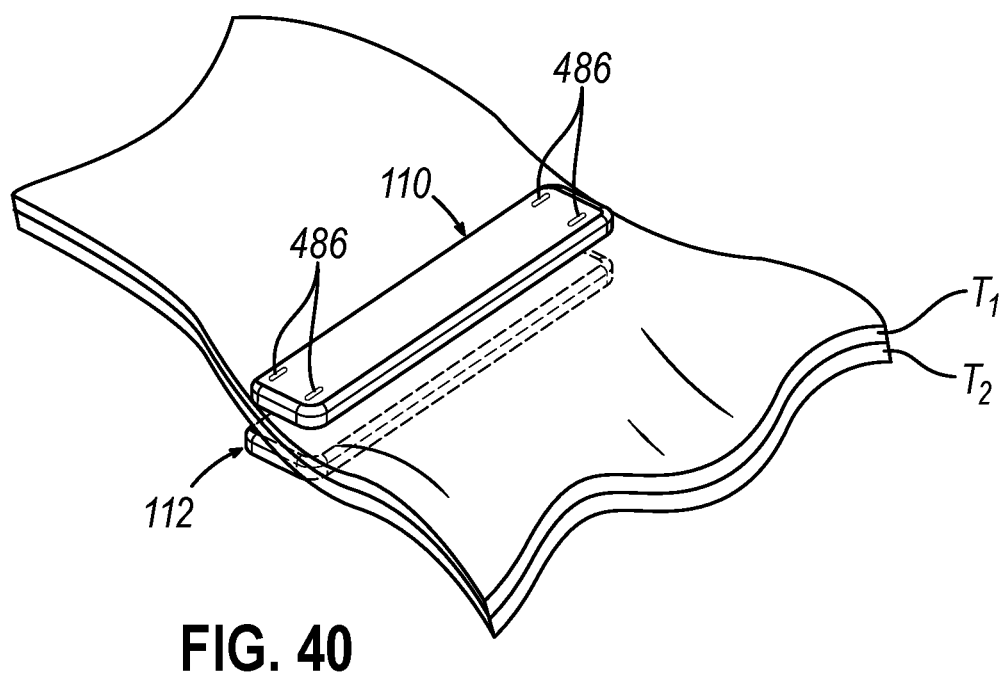
FIG. 40 depicts a perspective view of the buttress assemblies of FIG. 7 attached to tissue via the end effector of FIG. 39.

While the moister in tissue ($T_1$, $T_2$) may be sufficient to remove buttress assemblies (110, 112) off jaws (472, 474), in some instances it may be desirable to ensure the buttress assembly (110, 112) does not move relative to tissue ($T_1$, $T_2$) after being applied. FIGS. 39 to 40 show an alternative buttress applicator end effector (480) that may be readily incorporated into surgical buttress applicator (460) in replacement of end effector (470) described above. End effector (480) is substantially similar to end effector (470) described above, with differences elaborated below. Therefore, end effector (480) includes a pair of jaws (482, 484) that are substantially similar to jaws (472, 474) described above. However, as best shown in between FIGS. 39-40, jaws (482, 484) of end effector (480) are configured to apply temporary fastening elements (486) to both buttress assemblies (110, 112) and respective layers of tissue ($T_1$, $T_2$) such that buttress assemblies (110, 112) are inhibited from undesirable moving relative to tissue ($T_1$, $T_2$) after being applied. Any suitable mechanisms may be used to apply temporary fastening elements (486) as would be apparent to one skilled in the art in view of the teachings herein.

E. Example Adjunct with Varying Thickness

As mentioned above, in some instances, it may be desirable to have an adjunct that varies in thickness along the length of adjunct. For example, when staples (80) are fired in accordance with the description herein, staple formation (in consistency and quality) may tend to be worst near the distal of end effector (50), especially in instances where thicker than normal tissue ($T_1$, $T_2$) is being severed and stapled. Therefore, a buttress assembly having a thinner section of buttress body at the distal end may minimize forces acting on tissue, which may provide for better staple formation while still providing consistent compression. FIG. 41 shows a first exemplary buttress assembly (500) having a variation in thickness along the length of buttress assembly (500); while FIG. 42 shows a second exemplary buttress assembly (4510) having a variation in thickness along the length of buttress assembly (510).

Buttress assembly (500) includes a buttress body (502) and an adhesive layer (504); which are substantially similar to buttress body (114, 118) and adhesive layer (116, 120) described above, with differences elaborated below. In particular, buttress body (502) includes a proximal portion (506) and a distal tapered potion (508). Proximal portion (506) includes a substantially uniform thickness and is formed of the same material as buttress bodies (114, 118). Distal tapered portion (508) is formed of a material that is slightly stiffer and also tapered into a thinner thickness toward the distal end of buttress body (502). The slightly stiff material of distal taper portion (508) may allow distal portion to provide substantially consistent compression of tissue ($T_1$, $T_2$) being grasped in accordance with the description herein. Additionally, the thinner cushion material of distal portion (508) may reduce the amount of closure force required for end effector (50) to reach the fully closed position in instances where thicker tissue is being grasped. Reducing the closure force required for end effector (50) to suitably grasp tissue may lead to better staple formation.

Buttress assembly (510) is substantially similar to buttress assembly (500) described above, with differences elaborated below. Therefore, buttress assembly (510) includes a buttress body (512) having a proximal portion (516) and a distal portion (518), and an adhesive layer (514); which may be substantially similar to buttress body (502), proximal portion (506), distal portion (508), and adhesive layer (504) described above. However, proximal portion (516) and a distal portion (518) in the current example are formed of the same material, rather than different material.

Figure 46:
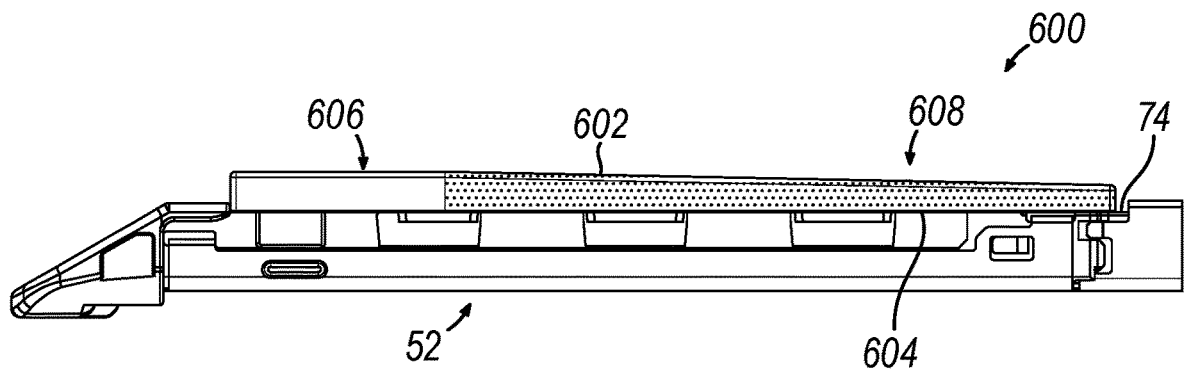
FIG. 46 depicts an elevational side view of an alternative buttress assembly attached to the staple cartridge of the end effector of FIG. 3.

While in the current example, the thickness of buttress body (502, 512) becomes thinner at distal portion (508, 518), this is merely optional. In some instances, buttress body (502, 512) becomes thinner at proximal portion (506, 516). FIG. 46 shows another exemplary buttress assembly (600) having variation in thickness along the length of buttress assembly (600). Buttress assembly (600) includes a buttress body (502) and an adhesive layer (604); which are substantially similar to buttress body (114, 118) and adhesive layer (116, 120) described above, with differences elaborated below. In particular, buttress body (602) includes a distal portion (506) and a proximal tapered potion (608). Distal portion (606) includes a substantially uniform thickness and is formed of the same material as buttress bodies (114, 118). Proximal tapered portion (608) is formed of a material that is slightly stiffer and also tapered into a thinner thickness toward the proximal end of buttress body (502). In some instance, proximal tapered portion (608) may be formed of the same material as buttress bodies (114, 118). In some instances, distal portion (606) may be formed from a material that is stiffer than the material used to from buttress bodies (114, 118).

Figure 47:
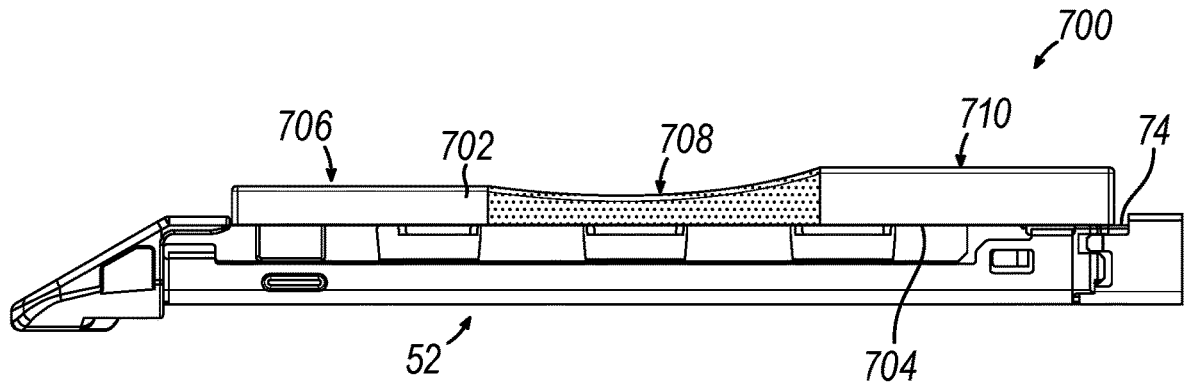
FIG. 47 depicts an elevational side view of an alternative buttress assembly attached to the staple cartridge of the end effector of FIG. 3.

FIG. 47 shows another exemplary buttress assembly (700) having variation in thickness along the length of buttress assembly (700). Buttress assembly (700) includes a buttress body (702) and an adhesive layer (704); which are substantially similar to buttress body (114, 118) and adhesive layer (116, 120) described above, with difference elaborated below. In particular, buttress body (702) includes a distal portion (706), an intermediate portion (708), and a proximal portion (710). Proximal portion (710) includes a substantially uniform first thickness and may be formed of the same material as buttress bodies (114, 118) or a slightly more rigid material. Distal portion (706) includes substantially uniform second thickness and is formed of the same material as buttress bodies (114, 118) or a slightly more rigid material. In the current aspect of the disclosure, second thickness is thinner than first thickness. However, second thickness may be thicker than first thickness in some aspects. Intermediate portion (708) is connected to both distal and proximal portion (706, 710) and includes a concave profile such that the central area of intermediate portion (708) is thinner than both first thickness and second thickness. However, in some aspects of the disclosure, intermediate portion (708) may include a convex profile such that the central area of intermediate portion (708) is thicker than both first thickness and second thickness.

Figure 48:
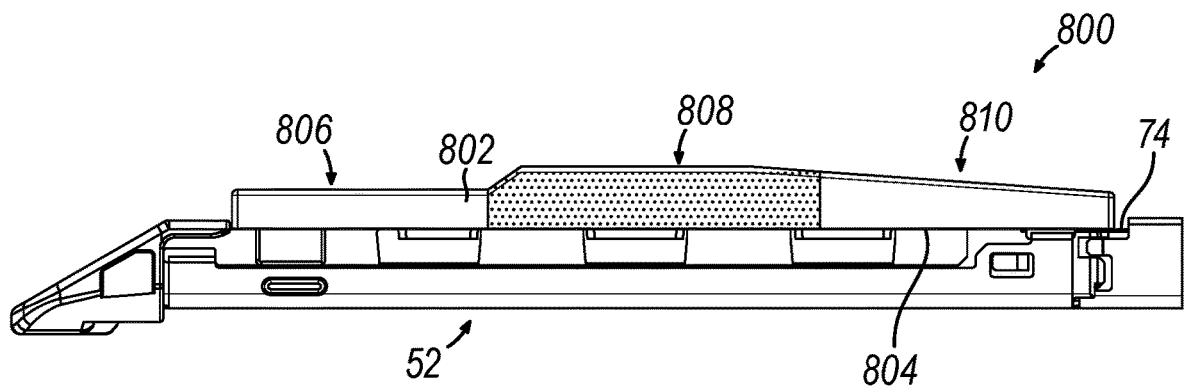
FIG. 48 depicts an elevational side view of an alternative buttress assembly attached to the staple cartridge of the end effector of FIG. 3.

FIG. 48 shows another exemplary buttress assembly (800) having variation in thickness along the length of buttress assembly (800). Buttress assembly (800) includes a buttress body (802) and an adhesive layer (804); which are substantially similar to buttress body (114, 118) and adhesive layer (116, 120) described above, with differences elaborated below. In particular, buttress body (8020 includes a proximal portion (806), a distal tapered portion (810), and an intermediate portion (808). Distal portion (806) includes a substantially uniform thickness and is formed of the same material as buttress bodies (114, 118). Proximal tapered portion (810) is formed of a material that is slightly stiffer and also tapered into a thinner thickness toward the proximal end of buttress body (802). In some instance, proximal tapered portion (810) may be formed of the same material as buttress bodies (114, 118). In some instances, distal portion (806) may be formed from a material that is stiffer than the material used to from buttress bodies (114, 118). Intermediate portion (808) includes various changes in thickness and is thicker than both proximal portion (810) and distal portion (806).

F. Exemplary Adjunct with Alternative Jaw Coupling

Figure 43A:
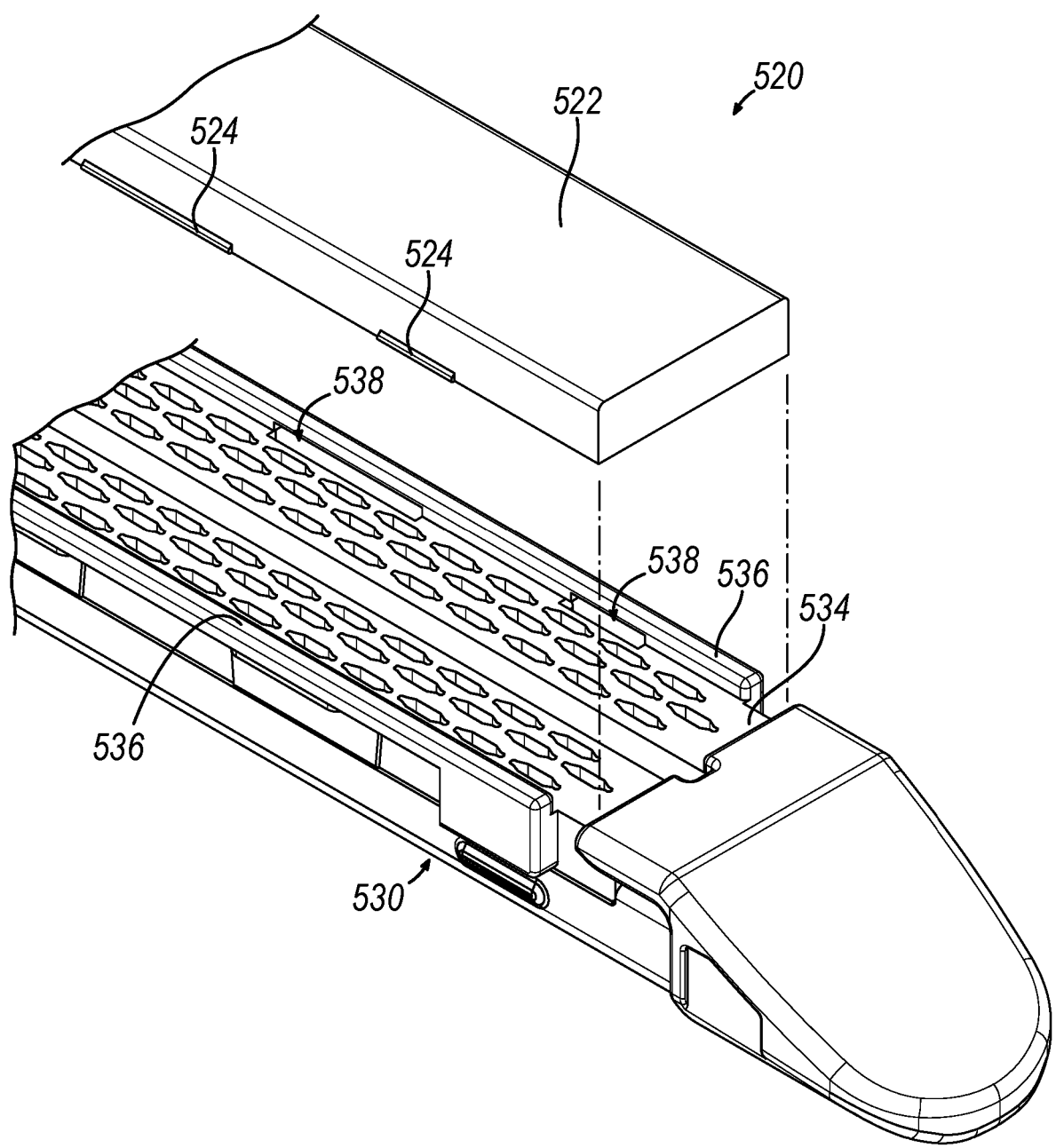
FIG. 43A depicts a perspective view of an alternative buttress assembly detached from an alternative cartridge that may be readily incorporated into the end effector of FIG. 3.
Figure 43B:
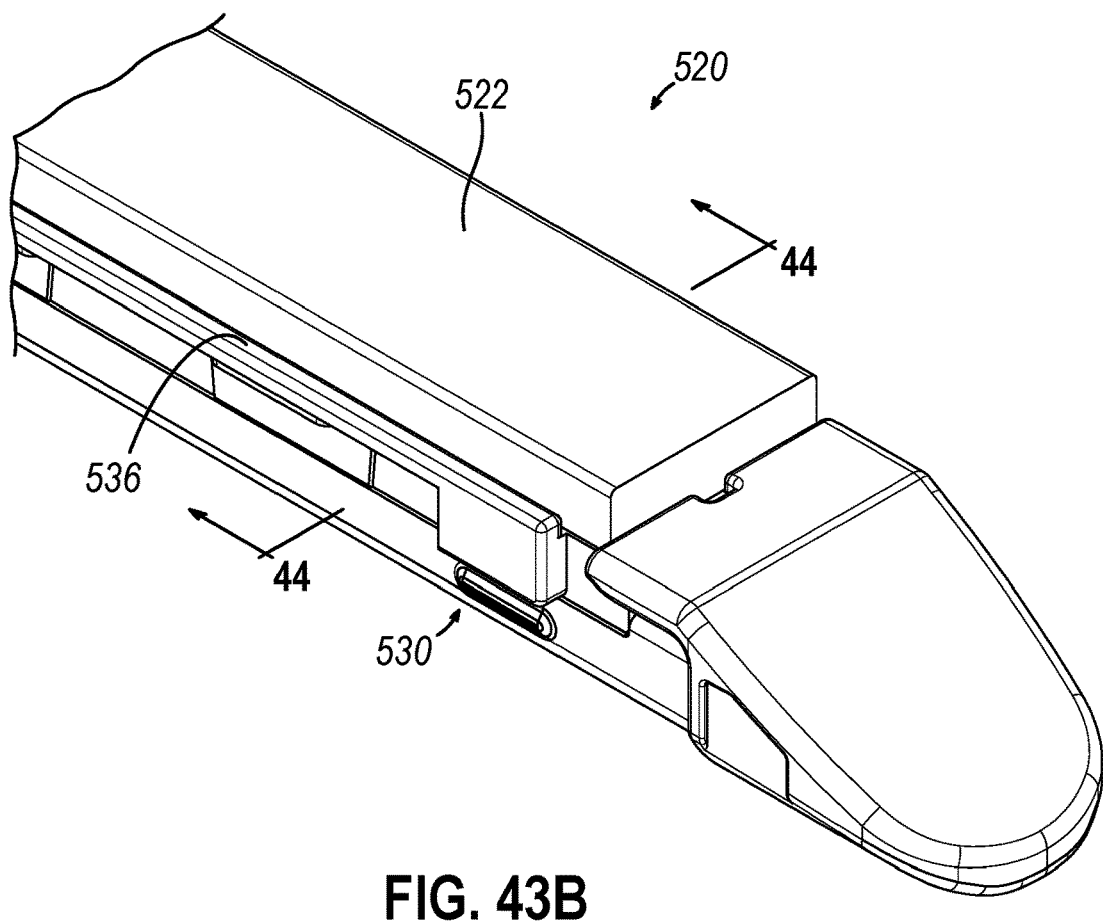
FIG. 43B depicts a perspective view of the buttress assembly of FIG. 43A attached to the alternative cartridge of FIG. 43A.
Figure 44:
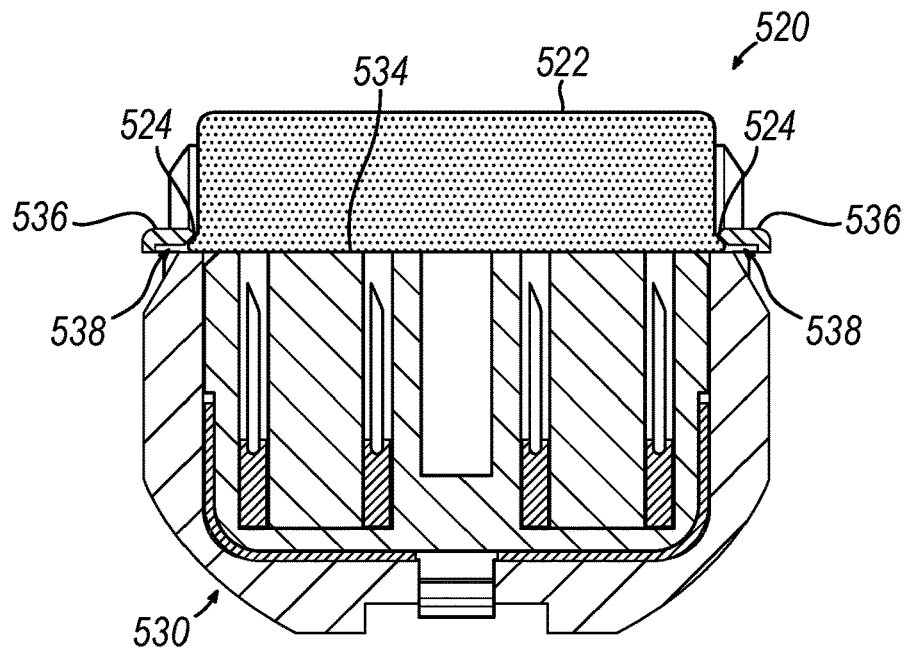
FIG. 44 depicts a cross-sectional view of the buttress assembly and the cartridge of FIG. 43A, taken along line 44-44 of FIG. 43B.

As mentioned above, in some instances, it may be desirable to provide an adjunct that resists lateral movement relative to the associated anvil (56) or upwardly facing deck (74) to which the adjunct is initially attached to prior to firing of end effector (50). FIGS. 43A-44 show an exemplary buttress assembly (520) and replaceable cartridge assembly (530). As will be described in greater detail below, buttress assembly (520) is configured to selectively attach to a replaceable cartridge (530) in such a manner as to inhibit lateral movement of buttress assembly (520) relative to staple deck (534) during exemplary use in accordance with the description herein.

Replaceable cartridge (530) may be readily incorporated into lower jaw (52) in replacement of replaceable cartridge (70) described above. Therefore, replaceable cartridge (530) is substantially similar to replaceable cartridge (70) described above, with differences elaborated below. In particular, replaceable cartridge (530) includes a pair of longitudinally extending rails (536) defining a plurality of openings (538). Rails (536) are located on lateral ends of staple deck (534) such that rails (536) and staple deck (534) define a recess area dimensioned to receive a portion of buttress assembly (520), as shown in FIG. 44.

Buttress assembly (520) includes a buttress body (522) that is substantially similar to buttress body (114, 118) described above, with differences described above. Rather than strictly having an adhesive layer utilized to couple buttress assembly (520) with staple deck (534), buttress body (522) includes a plurality of laterally extending protrusions (524). As best shown in FIG. 44, protrusion (524) are located on body (522) in order to fit within openings (538) defines by side rails (536). Protrusions (524) are sufficiently flexible in order to deform after end effector (50) has been fired in accordance with the description herein such that buttress body (522) may suitably detach from staple deck (534). Interaction between buttress body (522) and side rails (536) may inhibit buttress assembly (520) from laterally moving on staple deck (534) during use of end effect (50), especially when buttress assembly (520) encounters lateral forces during exemplary use. Therefore, if a surgeon is attempting to grasp tissue ($T_1$, $T_2$) with end effector (50) incorporating cartridge assembly (530) and buttress assembly (520), laterally forces imparted on buttress assembly (520) may not move buttress assembly (520) out of suitable alignment with staple deck (534).

In some instances, buttress assembly (520) may also include an adhesive layer configured to couple buttress assembly (520) with staple deck (534).

G. Exemplary Adjunct for Wound Care and Preventing Wound Dehiscence

Figure 45A:
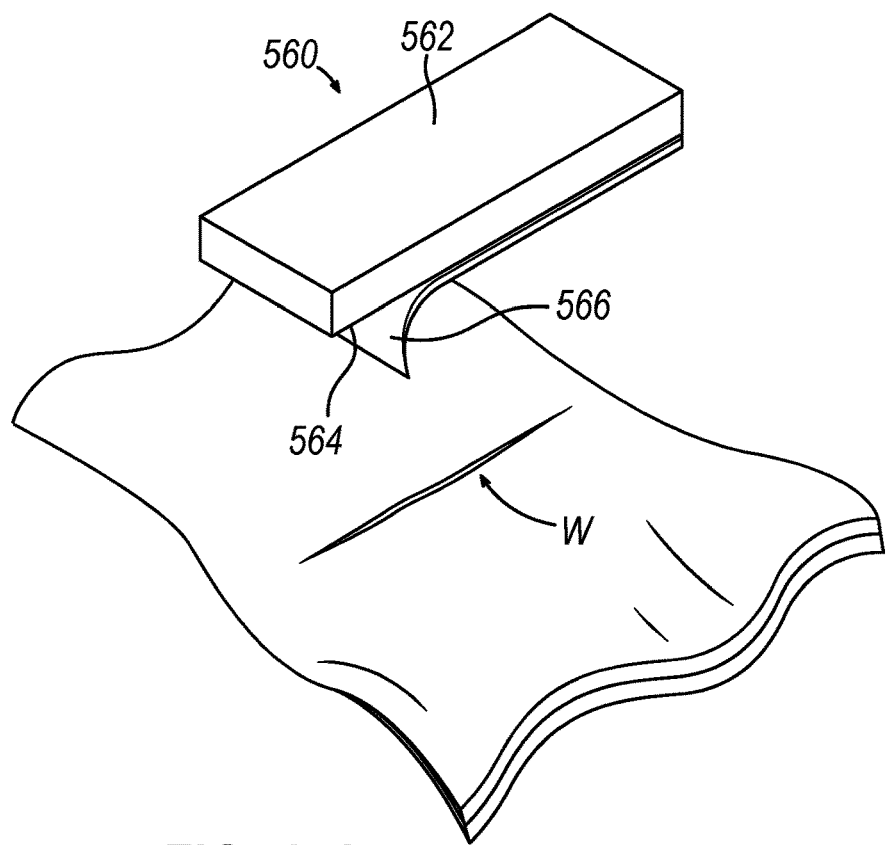
FIG. 45A depicts a perspective view of the buttress assembly of FIG. 7 placed adjacent to, yet detached from, a sutured piece of tissue.
Figure 45B:
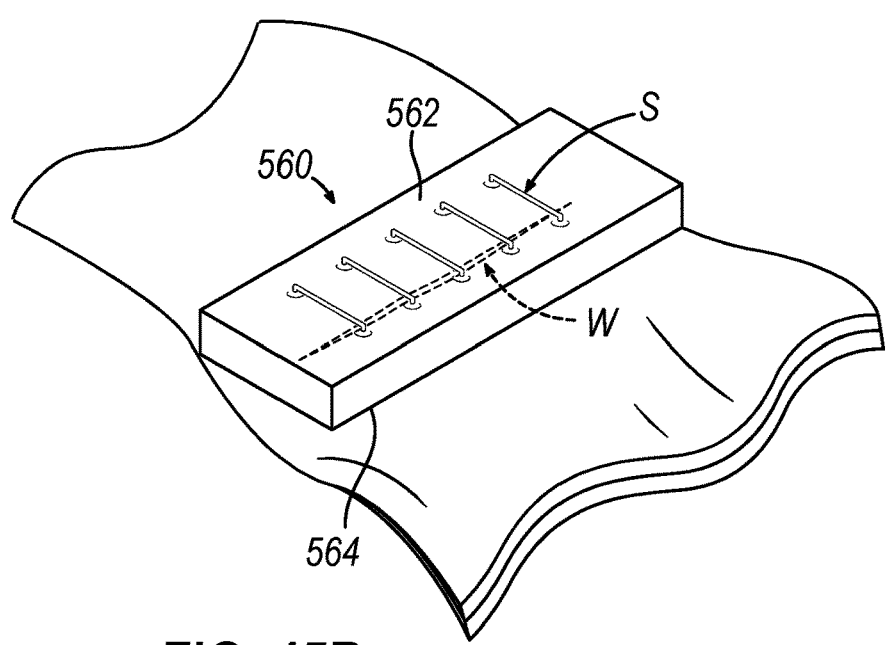
FIG. 45B depicts a perspective view of the buttress assembly of FIG. 7 attached to the sutured piece of tissue of FIG. 45A

As mentioned above, in some instances, it may be desirable to utilize an adjunct in medical procedures other than severing and stapling tissue, such as for wound care and to prevent wound dehiscence. FIGS. 45A-45B show an exemplary buttress assembly (560) used for wounded care to prevent wound dehiscence. Buttress assembly (560) is substantially similar to buttress assembly (110, 112) described above, with differences elaborated below. Therefore, buttress assembly (560) includes a buttress body (562) and an adhesive layer (564) that are substantially similar to buttress body (114, 118) and adhesive layer (116, 120) described above.

However, buttress assembly (560) is not attached to any type of replaceable cartridge, but comes as a stand-alone unit. Instead, buttress assembly (560) includes a removable adhesive cover (566). Removable adhesive cover (566) protects adhesive layer (564) such that adhesive layer (564) does not accidentally attach to items prior to its intended use. As shown between FIGS. 45A-45B, removable adhesive cover (566) may be peeled off to expose adhesive layer (564). Once adhesive layer (564) is suitably exposed, buttress assembly (560) may be applied to an open wound (W) via adhesive layer (564). Once suitably attached to open wound (W), a surgeon may apply suture(S) through buttress assembly (560) and wound (W) in order to suitably treat wound (W). With suture(S) going through buttress assembly and portions of tissue surrounding wound, buttress assembly (560) may apply more consistent compression to wound (W) via sutures(S) than without use of buttress assembly (560). Buttress assembly (560) may help seal suture wound(S) and also structurally support the wound to prevent wound dehiscence. Buttress assembly (560) may be removed after a suitable amount of time, such as when sutured wound(S) has suitably healed.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a first jaw, wherein the first jaw comprises an anvil defining a plurality of fastener forming features; (b) a second jaw, wherein the first jaw and the second jaw are configured to actuate relative to each other between an open position and a closed position to grasp tissue, wherein the second jaw comprises a fastening assembly comprising: (i) a deck defining a plurality of openings, and (ii) a plurality of fasteners, wherein each fastener of the plurality of fasteners is housed within a respective opening of the plurality of openings; (c) a firing assembly configured to actuate the plurality of fasteners out of the plurality of openings and against the plurality of fastener forming features; (d) a first buttress assembly associated with the anvil, wherein the first buttress assembly comprises a first material and a first thickness; and (e) a second buttress assembly associated with the deck, wherein the second buttress assembly comprises a second material and a second thickness, wherein the first material and the second material differ in rigidity, wherein the first thickness and the second thickness are different.

Example 2

The surgical instrument of any one or more the preceding Examples, wherein the second material comprises a plastic.

Example 3

The surgical instrument of any one or more the preceding Examples, wherein the second buttress assembly covers the plurality of staple openings.

Example 4

The surgical instrument of any one or more the preceding Examples, wherein the second buttress assembly is configured to guide the plurality of fasteners toward a respective fastener forming pocket while the firing assembly actuates the plurality of fasteners out of the plurality of openings.

Example 5

The surgical instrument of any one or more the preceding Examples, wherein the first buttress assembly comprises an adhesive layer interposed between the first material and the anvil.

Example 6

The surgical instrument of any one or more the preceding Examples, wherein the second buttress assembly comprises an adhesive layer interposed between the second material and the deck.

Example 7

The surgical instrument of any one or more the preceding Examples, wherein the fastening assembly is a replaceable staple cartridge.

Example 8

The surgical instrument of any one or more the preceding Examples, wherein the firing assembly comprises a distal cutting edge configured to sever tissue.

Example 9

The surgical instrument of any one or more the preceding Examples, wherein the first buttress assembly comprises a rigid base attached to the first material via a contoured profile, wherein the first material is configured to deform to thereby inhibit tissue flow relative to the deck in the closed configuration Example 10

The surgical instrument of any one or more the preceding Examples, wherein the first material is configured to deform to inhibit lateral tissue flow.

Example 11

The surgical instrument of any one or more the preceding Examples, wherein the first material is configured to deform to inhibit longitudinal tissue flow.

Example 12

The surgical instrument of any one or more the preceding Examples, wherein the first buttress assembly comprise a plurality of nodules each having a general cuboid shape.

Example 13

The surgical instrument of any one or more the preceding Examples, further comprising a shaft assembly extending proximally from the first jaw and the second jaw.

Example 14

The surgical instrument of any one or more the preceding Examples, further comprising a body attached to a proximal end of the shaft assembly.

Example 15

The surgical instrument of any one or more the preceding Examples, wherein the plurality of fasteners comprises a plurality of staples.

Example 16

A surgical instrument comprising: (a) a first jaw, wherein the first jaw comprises an anvil defining a plurality of fastener forming features; (b) a second jaw, wherein the first jaw and the second jaw are configured to actuate relative to each other between an open position and a closed position to grasp tissue, wherein the second jaw comprises a fastening assembly comprising: (i) a deck defining a plurality of openings, and (ii) a plurality of clips, wherein each clip of the plurality of clips is housed within a respective opening of the plurality of openings, wherein each clip comprises a crown and a leg, wherein each leg terminates at an end; (c) a firing assembly configured to actuate the plurality of clips out of the plurality of openings and against the plurality of fastener forming features to bend the legs of each clip into a fired configuration; (d) a first buttress assembly associated with the anvil, wherein the first buttress assembly comprises a reinforcing material, wherein the end of each leg, in the fired configuration, is configured to abut against an outer surface of the reinforcing material; and (e) a second buttress assembly associated with the deck, wherein the second buttress assembly comprises a cushion material configured to engage the crown of each clip in the fired configuration.

Example 17

The surgical instrument of any one or more the preceding Examples, wherein each clip in the plurality of clips forms a C shape in the fired configuration.

Example 18

The surgical instrument of any one or more the preceding Examples, wherein the reinforcing material is configured to distribute pressure onto tissue from each leg of the plurality of clips in the fired configuration.

Example 19

A surgical instrument comprising: (a) a first jaw, wherein the first jaw comprises an anvil defining a plurality of staple forming pockets; (b) a second jaw, wherein the first jaw and the second jaw are configured to actuate relative to each other between an open position and a closed position to grasp tissue, wherein the second jaw comprises a staple cartridge comprising: (i) a staple deck defining a plurality of staple openings, and (ii) a plurality of staples, wherein each staple of the plurality of staples is housed within a respective staple opening of the plurality of staple openings; (c) a firing assembly configured to actuate the plurality of staples out of the plurality of staple openings and against the plurality of staple forming pockets; (d) a first buttress assembly associated with the anvil, wherein the first buttress assembly comprises a cushion material; and (e) a second buttress assembly associated with the staple deck, wherein the second buttress assembly comprises a plastic material that is thinner than the cushion material.

Example 20

The surgical instrument of any one or more the preceding Examples, wherein the plastic material is configured to guide the plurality of staples toward a respective staple forming pocket as the firing assembly actuates the plurality of stapled out of the plurality of staple openings.

VII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/704,079, entitled "Tissue Cushion Adjunct for Surgical Stapler End Effector," filed on Mar. 25, 2022, published as U.S. Pat. Pub. No. 2023/0301674 on Sep. 28, 2023; U.S. patent application Ser. No. 17/704,082, entitled "Thermally Formed Tissue Cushion Adjunct for Surgical Stapler End Effector," filed on Mar. 25, 2022, published as U.S. Pat. Pub. No. 2023/0301657 on Sep. 28, 2023, issued as U.S. Pat. No. 12,161,331 on Dec. 10, 2024; U.S. patent application Ser. No. 17/704,083, entitled "Tissue Cushion Adjunct With Staple Leg Support Features for Surgical Stapler End Effector," filed on Mar. 25, 2022, published as U.S. Pat. Pub. No. 2023/0320742 on Oct. 12, 2023, issued as U.S. Pat. No. 12,082,834 on Sep. 10, 2024; and U.S. patent application Ser. No. 17/704,094, entitled "Surgical Stapler Features for Stapling Variable Thickness Tissue," filed on Mar. 25, 2022, published as U.S. Pat. Pub. No. 2023/0301675 on Sep. 28, 2023, issued as U.S. Pat. No. 12,114,882 on Oct. 15, 2024. The disclosure of each of these U.S. patent references is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a first jaw, wherein the first jaw comprises an anvil defining a plurality of fastener forming features;
   (b) a second jaw, wherein the first jaw and the second jaw are configured to actuate relative to each other between an open position and a closed position to grasp tissue, wherein the second jaw comprises a fastening assembly comprising:
      (i) a deck defining a plurality of openings, and
      (ii) a plurality of fasteners, wherein each fastener of the plurality of fasteners is housed within a respective opening of the plurality of openings;
   (c) a firing driver configured to actuate the plurality of fasteners out of the plurality of openings and against the plurality of fastener forming features;
   (d) a first buttress associated with the anvil, wherein the first buttress comprises:
      (i) a first material,
      (ii) a first thickness,
      (iii) a rigid base comprising an undulating surface formed by consecutive concave and convex sections of a wavelike pattern, the concave and convex sections being directly connected to each other, wherein the first material is attached to the rigid base adjacent to the undulating surface, wherein the first material is configured to deform toward the undulating surface to thereby cooperatively inhibit tissue flow relative to the deck in the closed position prior to the firing driver actuating the plurality of fasteners out of the plurality of openings; and
   (e) a second buttress associated with the deck, wherein the second buttress comprises a second material and a second thickness, wherein the first material and the second material differ in rigidity, wherein the first thickness and the second thickness are different.

2. The surgical instrument of claim 1, wherein the second material comprises a plastic.

3. The surgical instrument of claim 1, wherein the second buttress covers the plurality of staple openings.

4. The surgical instrument of claim 1, wherein the second buttress is configured to guide the plurality of fasteners toward a respective fastener forming pocket while the firing driver actuates the plurality of fasteners out of the plurality of openings.

5. The surgical instrument of claim 1, wherein the first buttress comprises an adhesive layer interposed between the first material and the anvil.

6. The surgical instrument of claim 1, wherein the second buttress comprises an adhesive layer interposed between the second material and the deck.

7. The surgical instrument of claim 1, wherein the fastening assembly is a replaceable staple cartridge.

8. The surgical instrument of claim 1, wherein the firing driver comprises a distal cutting edge configured to sever tissue.

9. The surgical instrument of claim 1, wherein the first material is configured to deform toward the concave surface to thereby cooperatively inhibit lateral tissue flow.

10. The surgical instrument of claim 1, wherein the first material is configured to deform toward the concave surface to thereby cooperatively inhibit longitudinal tissue flow.

11. The surgical instrument of claim 1, further comprising a shaft assembly extending proximally from the first jaw and the second jaw.

12. The surgical instrument of claim 11, further comprising a body attached to a proximal end of the shaft assembly.

13. The surgical instrument of claim 12, wherein the plurality of fasteners comprises a plurality of staples.

14. A surgical instrument comprising:
   (a) a first jaw, wherein the first jaw comprises an anvil defining a plurality of fastener forming pockets
   (b) a second jaw, wherein the first jaw and the second jaw are configured to actuate relative to each other between an open position and a closed position to grasp tissue, wherein the second jaw comprises a fastening cartridge comprising:
      (i) a deck defining a first plurality of openings, a second plurality of openings, wherein the deck defines a central channel that is interposed between the first plurality of openings and the second plurality of openings, and
      (ii) a plurality of fasteners, wherein each fastener of the plurality of fasteners is housed within a respective opening of either the first plurality of openings or the second plurality of openings;
   (c) a firing driver configured to actuate the plurality of fasteners out of the plurality of openings and against the plurality of fastener forming pockets;
   (d) a first buttress associated with the anvil, wherein the first buttress comprises:
      (i) a first material,
      (ii) a first thickness, and
      (iii) a rigid base comprising a contoured surface defining a central convex profile, a first lateral concave profile directly connected to the central convex profile, and a second lateral concave profile directly connected to the central convex profile, wherein the central convex profile, the first lateral concave profile, and the second lateral concave profile form a wavelike pattern, wherein the central convex profile is directly adjacent to the central channel of the deck in the closed position, wherein the first lateral concave profile is directly adjacent to the first plurality of openings of the deck in the closed position, wherein the second lateral concave profile is directly adjacent to the second plurality of openings of the deck in the closed position, wherein the first material is attached to the rigid base adjacent to the contoured surface, wherein the first material is configured to deform toward the contoured surface to thereby cooperatively inhibit lateral tissue flow toward the central channel while the first jaw and the second jaw are in the closed position prior to the firing driver actuating the plurality fasteners out of the plurality of openings; and (e) a second buttress associated with the deck, wherein the second buttress comprises a second material and a second thickness, wherein the first material and the second material differ in rigidity, wherein the first thickness and the second thickness are different.

* * * * *